US012685808B2

(12) United States Patent
Sheriff et al.

(10) Patent No.: US 12,685,808 B2
(45) Date of Patent: Jul. 21, 2026

(54) USING AN ALKALIHYDROXIDE SOLUTION FOR THE REGENERATION OF AN APHERESIS COLUMN

(71) Applicant: Pentracor GmbH, Hennigsdorf (DE)

(72) Inventors: Ahmed Sheriff, Berlin (DE); Stephan Mattecka, Berlin (DE); Birgit Vogt, Berlin (DE)

(73) Assignee: Pentracor GmbH, Hennigsdorf (DE)

( * ) Notice: Subject to any disclaimer, the term of this patent is extended or adjusted under 35 U.S.C. 154(b) by 816 days.

(21) Appl. No.: 17/797,519

(22) PCT Filed: Feb. 5, 2021

(86) PCT No.: PCT/EP2021/052874
§ 371 (c)(1),
(2) Date: Aug. 4, 2022

(87) PCT Pub. No.: WO2021/156482
PCT Pub. Date: Aug. 12, 2021

(65) Prior Publication Data

US 2023/0090960 A1 Mar. 23, 2023

(30) Foreign Application Priority Data

Feb. 5, 2020 (EP) .................................... 20155753

(51) Int. Cl.
*A61M 1/34* (2006.01)
*B01J 20/286* (2006.01)

(52) U.S. Cl.
CPC .............. *A61M 1/34* (2013.01); *B01J 20/286* (2013.01)

(58) Field of Classification Search
None
See application file for complete search history.

(56) References Cited

U.S. PATENT DOCUMENTS

2007/0225226 A1* 9/2007 Hammond ............. A61K 38/08 530/331
2009/0196938 A1* 8/2009 Vogt ....................... B01J 20/321 424/537
2013/0189225 A1* 7/2013 Voit ....................... A61K 38/00 424/85.4

(Continued)

FOREIGN PATENT DOCUMENTS

DE 10065241 A1 * 7/2001 .......... B01J 20/3212

OTHER PUBLICATIONS

International Search Report and Written Opinion for International Patent Application No. PCT/EP2021/052874 dated May 10, 2021, 3 pages.

*Primary Examiner* — Bradley R Spies
*Assistant Examiner* — Jeannie McDermott
(74) *Attorney, Agent, or Firm* — Knobbe, Martens, Olson & Bear, LLP

(57) ABSTRACT

The present invention relates to the use of alkali hydroxide for the regeneration of apheresis columns for the affinity chromatographic removal of CRP and a method for the simplified regeneration of apheresis columns for the affinity chromatographic removal of CRP with the use of an alkali hydroxide solution and apheresis devices which are designed in such a manner as to be resistant to alkali hydroxide solutions and to allow the regeneration of apheresis columns for the affinity chromatographic removal of CRP in continuous operation.

18 Claims, 6 Drawing Sheets

(56) References Cited

U.S. PATENT DOCUMENTS

| | | | | |
|---|---|---|---|---|
| 2015/0093800 | A1* | 4/2015 | Mahajan | B01D 15/203 530/416 |
| 2017/0281679 | A1 | 10/2017 | Chtourou | |
| 2017/0319982 | A1* | 11/2017 | Sheriff | B01J 20/3251 |
| 2021/0060232 | A1* | 3/2021 | Luo | B01J 20/28047 |

* cited by examiner

USING AN ALKALIHYDROXIDE SOLUTION FOR THE REGENERATION OF AN APHERESIS COLUMN

The present invention relates to the use of alkali hydroxide for the regeneration of apheresis columns, in particular apheresis columns for affinity chromatographic removal of CRP, and to a method for simplified regeneration of apheresis columns for affinity chromatographic removal of CRP with an alkali hydroxide solution, preferably a sodium hydroxide solution, and apheresis devices which configured to be resistant to alkali hydroxide solutions.

BACKGROUND OF THE INVENTION

According to the World Health Organization (WHO), approximately 17,000,000 people died from cardiovascular diseases in 2008. This makes cardiovascular diseases the most common cause of death among non-communicable diseases and is responsible for about one-third of all deaths worldwide each year. According to estimates, this number will increase to approximately 23,000,000 deaths per year by 2030.

Thus, cardiovascular diseases are and will remain not only the leading cause of death worldwide, but also cause enormous medical costs for national health systems and health insurance companies. Two of the most common and most damaging manifestations of cardiovascular diseases are the occurrence of arteriosclerosis and thrombosis, which in turn are causative factors for heart attacks and strokes, among other things.

In recent years, great progress has been made in the treatment of cardiovascular diseases. This progress has been made possible not only by growing knowledge regarding disease-causing mechanisms, but also by the early identification of patients at risk. Indeed, the identification of disease risks and their early treatment are important features of modern medical practice. Over the past 25 years, a variety of factors and clinical parameters have been identified that correlate with either the current state of disease or the future likelihood of cardiovascular disease. Such risk factors may be measurable biochemical or physiological parameters such as serum cholesterol, HDL, LDL, and fibrinogen levels but may also include behavioral patterns such as obesity and smoking. In cases where a risk factor is not merely indicative of a disease or its development, but is actually causally involved in its development, therapeutic manipulation of this risk factor can influence the course of the disease or reduce the risk of its development.

As an acute-phase protein, CRP is part of the innate immune system and is formed in the liver in the course of inflammatory reactions and released into the blood. The formation of CRP is primarily induced by cytokines that are expressed in the course of an acute or chronic inflammatory reaction. The strongest stimulus for the formation of CRP is interleukin-6 (IL-6). Therefore, levels of CRP as well as of IL-6 in the blood are indicators of a local or systemic inflammatory response. Chronic inflammation is thought to be one of the underlying and supporting pathological phenomena in cardiovascular disease. In this context, it is increasingly assumed that CRP is not only predictive of cardiovascular disease but also causally involved in its development or may influence its course.

The normal value for CRP in the blood of humans varies from person to person, but is on average about 0.8 mg CRP per liter of blood, but can rise to well over 100 mg CRP per liter of blood in case of acute or chronic inflammatory reactions (e.g., bacterial infections, atherosclerosis, after a heart attack). Since the half-life of CRP in the blood (approx. 19 hours) is constant and thus independent of the patient's state of health, the synthesis rate of CRP alone is responsible for the regulation of the CRP level in the blood (Pepys & Hirschfield, J. Clin. Invest., 2003, 111: 1805-1812). Consequently, the greatly increased synthesis of CRP in acute pathological conditions places special demands on therapeutic approaches to CRP removal from patients (high-risk or acute patients), since a substantial amount of CRP must be removed to reduce blood CRP levels to normal values. Thus, there is a need for particularly efficient devices and boundary conditions for CRP removal from patients' blood.

Extracorporeal apheresis is a procedure used to physically remove substances from blood or blood plasma by means of filtration, precipitation, or adsorption. The term therapeutic apheresis generally refers to medical procedures for the removal of pathogenic components from circulating blood. The removal of pathogenic substances from blood or blood plasma by extracorporeal apheresis using an extracorporeal circuit has become established as a therapeutic measure in routine clinical practice for numerous diseases. For example, immuno-adsorption can be used to specifically remove antibodies and circulating immune complexes from plasma of patients.

For the therapeutic extracorporeal removal of C-reactive protein (CRP) from blood or blood plasma, CRP apheresis columns are known from the state of the art that allow selective removal of CRP from blood or blood plasma, wherein these contain matrix substrate materials (such as agarose) covalently coupled with phosphocholine or a phosphocholine derivative as ligands for CRP.

The European patent application EP 3 020 726 A1 discloses a column material functionalized with ω-phosphonooxy-alkylammonium groups and/or with ω-ammoniumalkoxy-hydroxyphosphoryloxy groups for the affinity chromatographic removal of CRP by $Ca^{2+}$-dependent binding of CRP. An advantage of using such phosphocholine derivatives for CRP apheresis is that CRP can be selectively removed from other plasma components, such as other plasma proteins, by a highly specific ligand. One of the reasons for this is that the $Ca^{2+}$-dependent binding mechanism of CRP to phosphocholine or derivatives thereof is used for the adsorption of CRP. The only other substances that also bind to phosphocholine are antibodies against phosphatidylcholine. Loss of other plasma proteins such as γ-globulins is thus minimized.

For the therapeutic use of extracorporeal apheresis by means of an extracorporeal circulation system, reusable adsorbers are usually used, since the apheresis is performed in several cycles during one treatment session. Reusable adsorbers are known from the state of the art which consist of a housing filled with a carrier substance and a binding factor coupled thereto. Reusable adsorbers are usually regenerable, since after passing through a quantity of plasma which depends on the concentration of the substance to be adsorbed, the adsorber is "saturated" and binding of the substance can no longer take place. Two adsorbers are usually used for one treatment. While plasma is pumped through one adsorber, the second adsorber is regenerated at the same time. In this process, the adsorber is rinsed free of the bound substances with various regeneration solutions and thus prepared again for a new plasma charge. The permissible number of regenerations is specified by the manufacturers. The reusable adsorber may only be used for one and the same patient. To prevent germ growth in the adsorbers, they must be filled with a preservative liquid at the end of each treatment, which must be rinsed out before each new therapy session. However, significant costs could be saved by reusing them. The operation of the existing devices (combination of two or more medical devices) is very complex and highly demanding. In addition, the devices are rarely used overall.

The apheresis columns are used for one patient in several treatment sessions. For this purpose, the apheresis columns are stored in a preservation liquid after treatment. In the prior art, at the end of the apheresis treatment, the apheresis column is treated with a regeneration solution, then rinsed with a rinsing solution such as physiological saline, and finally a preservation liquid such as a 0.04% polyhexamethylene biguanide—solution (PHMB solution) or a solution of sodium azide and PBS (phosphate buffered saline) is introduced into the apheresis column. Therefore, the preservation step involves a significant time commitment for clinical staff. If the regeneration solution and the preservative were the same solution, two additional steps for the preservation of the apheresis column could be avoided.

Generally, in therapeutic apheresis, the patient's blood is first mixed with an anticoagulant (e.g., citrate or heparin) and separated into plasma and cellular components using a blood centrifuge or plasma filtration device. The plasma is then passed through the apheresis column and the pathogenic substance is removed by adsorption. The treated plasma is then recombined with the cellular components and returned to the patient. During regeneration, the apheresis column is decoupled from the extracorporeal circulation system.

In apheresis treatment for the selective removal of CRP from blood plasma, an average of 6000 mL of plasma is treated in 6 to 12 cycles in one treatment session. The processing of 6000 mL of blood plasma usually takes about 4-5 hours including the regeneration of the apheresis column. Regeneration of the apheresis column is thus a time factor that affects the total duration of a treatment session. It is therefore desirable to keep the regeneration time to a minimum, especially since the apheresis column is not available for the removal of CRP from blood or blood plasma during regeneration.

For the regeneration of the apheresis column, in particular of CRP apheresis columns, glycine/HCl or EDTA solutions are used in the prior art, which denature bound proteins by an abrupt change in the pH value to the acidic range or which dissolve the bond between the adsorbed molecule to be removed, in particular CRP, and the support material of the apheresis column by complexing the binding-mediating cations, in particular calcium. In the prior art, no compounds are known that enable the separation of bound molecules to be removed, in particular CRP, from a support material of the apheresis column via a different mechanism.

DE 4338858 C1 discloses a device for the regeneration of an apheresis column. DE 4338858 C1 teaches the use of a reservoir in which the plasma is temporarily stored during the regeneration of the apheresis column. The regeneration of the apheresis column takes place via the combination of glycine/HCl, PBS and NaCl solution known from the prior art. Furthermore, DE 4338858 C1 does not disclose a bypass line that allows the plasma flow to be diverted bypassing the apheresis column during its regeneration.

The European patent application EP 3 020 726 A1 discloses the use of a citrate solution for affinity chromatographic purification of CRP using phosphocholine and its derivatives. Binding buffer pH 8.0 (0.1 M Tris, 0.2 M NaCl, 2 mM $CaCl_2$), and elution buffer pH 8.0 (EDTA) or regeneration solution pH 2.8 (glycine-/HCl) known from the prior art are used for chromatography.

It has been found by the inventors of the present invention that a protein layer forms around the matrix particles (e.g. agarose particles) during regeneration with glycine/HCl, particularly during regeneration of apheresis columns for affinity chromatographic removal of CRP. This is probably due to acidic protein precipitation. If the patient's blood to be purified contains a high concentration of cell-free DNA/RNA, this can lead to an enhancement of the effect. The formation of the protein layer in the apheresis column masks binding sites and reduces the performance of the apheresis material. The original state cannot be restored by known measures such as further regeneration attempts with a glycine/HCl solution. This problem has not been described in the prior art so far. As the damage to the apheresis column progresses, the treatment time for the patient increases and so does the suffering time of the patient. In addition, the damaged apheresis columns are often no longer usable for further use, so that the treatment costs considerably increase.

Furthermore, the protein layer or protein-DNA as well as protein-RNA layer can lead to a clogging of the fine pores, which increases the system pressure at a constant flow rate. A further increase in the flow rate is accompanied by a further increase in pressure. This can lead to a discontinuation of the treatment. These apheresis columns are also no longer suitable for further use.

Generally, in affinity chromatography, the columns used are first adjusted with a binding buffer that positively influences and promotes the interaction between the target substance and the ligand on the matrix substrate material. After application of the sample and passage through the column, the bound target substance is flushed out or eluted. To elute the target molecule, an elution buffer that is specifically based on the binding mechanism is used to break the interaction between the target substance and the ligand, such as by a competitive ligand, by changing the pH, ionic strength or polarity. After elution is complete, the columns are washed with a washing buffer or again with binding buffer. Elution is specific to the type of affinity chromatography, as it is used to resolve the specific interaction between the target substance and the ligand.

For the selective removal of pathogenic substances from blood or blood plasma, prior art therapeutic apheresis relies on the principle of affinity chromatography, since this type of separation is based on a specific reversible interaction of a substance, such as a protein or a group of proteins, and a specific ligand coupled to the carrier matrix. The advantage of affinity chromatographic purification is based on its high selectivity, which allows targeted removal of the target substance from the blood or blood plasma during therapeutic apheresis, with no or minimal removal of other components from the blood plasma due to non-specific interactions. Affinity chromatography therefore specifically exploits the biological function of the biomolecule or its individual structure. The interaction between the ligand and the target molecule can be the result of electrostatic or hydrophobic interactions, van der Waals forces, or hydrogen bonding.

The German patent application DE 100 65 241 A1 discloses immuno-adsorbers for extracorporeal apheresis and methods for their preparation. The disclosed immuno-adsorbers are directed to the removal of immunologically active substances, such as immunoglobulins, antibodies and immune complexes, from the blood plasma or whole blood of patients suffering from immunological diseases. The disclosed immuno-adsorbers are prepared by covalent binding of the ligand protein A to different carrier materials.

It is known from the prior art that protein A shows a high affinity for the Fc region of polyclonal and monoclonal IgG antibodies. Columns consisting of protein A bound to a matrix substrate material are thus suitable for affinity chromatographic purification of antibodies, i.e. the column is specific for antibodies, but not for CRP. DE 100 65 241 A1 thus does not disclose apheresis columns for the affinity chromatographic removal of CRP.

In DE 100 65 241 A1, binding buffer pH 7.0 and elution buffer pH 2.2 are used for adsorption of hIgG (Example 1 D) to the protein A adsorber in a standard cycle (apheresis elution buffer: 0.03-0.05 M citrate, 0.15 M NaCl). The disclosed protein A adsorbent was tested for chemical stability against various regeneration media in the pH range 2-14 (Example 13D). Regeneration media used included a 0.1 M sodium hydroxide solution (pH 14). For regeneration, the respective regeneration medium was pumped over the column and then washed with binding buffer pH 7.0. Subsequently, the hIgG binding capacity was determined. The determination of the hIgG binding capacity was performed according to the standard cycle with binding buffer pH 7.0 and elution buffer pH 2.2. In addition, no human plasma was used, but a solution of hγ-globulin dissolved in apheresis binding buffer pH 7.0 (concentration 8 mg/mL). The regeneration disclosed in DE 100 65 241 A1 is carried out in a separate and additional rinsing step, whereby the protein A adsorber, after loading with hIgG, had already been treated with elution buffer pH 2.2 and wash buffer before the regeneration was carried out.

For therapeutic apheresis, additional rinsing steps for regeneration or also for washing an apheresis column represent an unfavorable extension of the regeneration time and thus of the total treatment time. The more rinsing steps and the more regeneration solutions or washing solutions a regeneration cycle includes the longer the total regeneration time for the apheresis column. In particular, if two adsorbers are used for one treatment, with plasma being pumped through one adsorber while the second adsorber is regenerated at the same time, an increase in rinsing steps and use of multiple regeneration solutions is not appropriate, as regeneration of the second adsorber should be completed before the first adsorber is saturated to ensure continuous and smooth removal of the pathogenic substance from the blood or blood plasma.

Moreover, DE 100 65 241 A1 only tests a single treatment with the respective regeneration medium. For therapeutic apheresis, however, it is necessary that the regeneration is repeatable, i.e. that the regeneration medium can be used repeatedly without having any adverse effect on the binding capacity, such as a reduction of the binding capacity to the substance to be removed from the blood or blood plasma. In therapeutic apheresis, the apheresis column is usually regenerated several times during a single treatment session.

Regarding repeated use, DE 100 65 241 A1 (Example 14D) describes the hIgG binding capacity as a function of repeated use of 0.5 N NaOH in an additional regeneration step. Here, hIgG binding was performed with human plasma (4.2 mL/mL gel; 6.5-fold excess hIgG; concentration 9.8 mg/mL), according to standard cycle with binding buffer pH 7.0 and elution buffer pH 2.2. In the repeated regeneration following a standard cycle, 0.5 N NaOH was pumped over the column for 2 h at a flow rate of 2 mL/min (corresponding to 80 times the gel volume). This was followed by washing with water, apheresis buffer pH 2.2 and apheresis buffer pH 7.0. It is disclosed that the hIgG binding capacity dropped to 50% after only 5 cycles when the 0.5 N NaOH was used. In another experiment, it is disclosed that when regenerated with 0.5 N NaOH for 7 min at 62.5 mL adsorbent, only 83% of the initial binding capacity was observed after 6 regeneration cycles. DE 100 65 241 A1 thus teaches that a sodium hydroxide solution can only be used to a limited extent as a regeneration medium, since a reduction in binding capacity occurs with repeated regeneration.

The European patent application EP 3 459 552 A1 discloses the provision of a "universal" plasma obtained from a mixture of plasmas from different donors with blood groups A, B, AB and/or 0. The "universal" plasma has a low level of anti-A and anti-B antibodies and is therefore intended to be compatible with all blood groups. The anti-A antibodies and anti-B antibodies are thereby removed from the plasma mixture by immunoaffinity chromatographic purification. The matrix has oligosaccharide groups resembling epitopes of blood groups A and/or B. For regeneration, reference is made to treatment with sodium hydroxide, e.g. 1 M NaOH, without further explanation.

The binding mechanism on which the immunoaffinity chromatographic purification with the functionalized matrix according to EP 3 459 552 A1 is based concerns specific carbohydrate-protein interactions. Thus, EP 3 459 552 A1 does not disclose apheresis columns for affinity chromatographic removal of CRP, in particular apheresis columns for extracorporeal removal of CRP from blood or blood plasma and thus apheresis columns applicable for therapeutic apheresis. Furthermore, EP 3 459 552 A1 also relates more to the field of preparative plasma apheresis, in which plasma is obtained during a donation. This is to be distinguished from therapeutic apheresis, in which the treated plasma is returned directly to the patient.

DE 100 65 241 A1 and EP 3 459 552 A1 do not disclose apheresis columns for affinity chromatographic removal of CRP. In connection with apheresis columns for affinity chromatographic removal of CRP, no other compounds and methods are known in the prior art, apart from the use of glycine/HCl or EDTA solutions for regeneration, which enable the separation of bound molecules to be removed, in particular CRP, on a support material of the apheresis column. Therefore, there is a need for uses, methods and devices that make it possible to prevent masking of binding sites and increasing the treatment time of apheresis and, in particular, to ensure the smooth flow.

Therefore, it is an object of the present invention to provide uses, methods and devices that allow to prevent the masking of the binding sites and the increase of the treatment time of the apheresis and, in particular, to ensure the smooth flow.

A further object of the present invention is to provide uses, methods and devices for the simplified regeneration of apheresis columns, in particular apheresis columns for the affinity chromatographic removal of CRP, whereby the stated drawbacks of the devices and methods known from the prior art are minimized. In other words, the object of the present invention is to provide a device for the simplified regeneration of apheresis columns, in particular for the simplified regeneration of apheresis columns for the affinity chromatographic removal of CRP, which can be operated with reduced training effort, and thus with reduced personnel effort and reduced overall costs.

This object is solved by the teachings of the independent claims. Further advantageous embodiments result from the description, the examples and the appended claims.

DESCRIPTION OF THE INVENTION

The term "CRP" as used herein is equivalent to "C-reactive protein". Herein, it preferably refers to human C-reactive protein. C-reactive protein (CRP) is a pentamer whose subunits are each associated with two $Ca^{2+}$ ions, with the aid of which binding to ligands such as phosphocholine or derivatives thereof can occur.

The term "affinity chromatographic" in reference to the removal of CRP, as used in the present application, means that the removal of CRP occurs by a specific binding between CRP and components of the apheresis column for the removal of CRP. In this context, one may also speak of "selective removal of CRP" or "selective CRP apheresis". Such specific binding between CRP and components of the apheresis column are based on the structural properties of the CRP protein and include, for example, the characteristic binding of CRP to phosphocholine as well as its derivatives or the binding of CRP to antibodies directed against an epitope of CRP. Selective or molecule-specific removal of CRP involves CRP binding with higher affinity to the matrix in the apheresis column than to other structures/molecules. Also, CRP binds with higher affinity to the matrix in the apheresis column than other substances present in the blood, i.e. the matrix has specificity for CRP or the matrix is specific for CRP. The matrix, preferably a solid phase modified with phosphocholine, preferably binds CRP selectively, i.e. almost exclusively CRP is bound and no other blood components such as LDL-cholesterol, antibodies, or uremic toxins. Thus, "removal of CRP", as disclosed herein, preferably means selective removal of CRP. However, the term "selective" with respect to the removal of CRP, as used in the present application, does not mean that exclusively CRP is removed. Here, it is obvious to the person skilled in the art that in such an affinity chromatographic removal of CRP, other substances may inevitably bind (unintentionally) to the column material to a certain extent and thus also be removed to a certain extent. An example would be antibodies directed against phosphocholine, which can therefore also bind to a column material that has been functionalized with phosphocholine. Another possibility is the never completely avoidable non-specific binding of components of the biological fluid to e.g. matrix substrate materials.

Regeneration, as used herein, refers to the process by which the matrix of the apheresis column comprising a matrix substrate material and a ligand, from which accumulated substances are to be removed, are restored to a therapeutically usable state, i.e. are regenerated.

The term "regeneration solution", as used herein, in an affinity chromatographic method for removing a substance from a sample (herein, biological fluids such as blood or blood plasma), refers to a solution that is applied following the application of the sample to the column material and following the specific binding of the substance to be removed to the column material, in order to release this specific binding again and thus to release (or elute) the substance to be removed from the column material again. In addition to regeneration solution, the term "elution buffer" (also referred to as "elution solution"), as used herein, in an affinity chromatographic method for removing a substance (here, selective removal of CRP) from a sample (here, biological fluids such as blood or blood plasma), refers to a solution which is applied following the application of the sample to the column material and following specific binding of the substance to be removed to the column material to release this specific binding again and thus to release (or elute) the substance to be removed from the column material again. In contrast to the binding buffer, the elution buffer is intended to create conditions in the column material that do not allow binding of the substance to be removed, but rather actually prevent it.

In contrast to the elution buffer, the regeneration solution also serves to remove accumulated substances in order to bring an apheresis column back into a therapeutically usable state or serves to regenerate it. In other words, the regeneration solution serves both to loosen the specific binding of the substance to be removed to the column material in order to release (or elute) the substance to be removed from the column material again and to remove accumulated substances in order to bring an apheresis column back into a therapeutically usable state or to regenerate it. The regeneration solution thus serves both elution and regeneration purposes. It is therefore preferred that the substance to be removed (in this case CRP) is also eluted when the regeneration solution is used. Therefore, the regeneration solution is used preferably to elute CRP from the apheresis column for affinity chromatographic removal of CRP, thereby returning the apheresis column to a therapeutically usable state.

The term "binding buffer" (also referred to as "binding solution"), as used herein, in an affinity chromatographic method for the removal of a substance (herein, selective removal of CRP) from a sample (herein, biological fluids such as blood or blood plasma) refers to a solution which is added to the sample and then applied together with the sample to the column material for removal of the substance. The binding buffer is intended to ensure adequate conditions for the specific binding of the substance to be removed to the column material.

The term "biological fluid", as used herein, refers to aqueous solutions that are present in mammals and preferably humans, such as cerebrospinal fluid, peritoneal fluid, pleural fluid, ascitic fluid, blood, blood plasma, liver extracts, and interstitial fluid. The present invention preferably relates to biological fluids containing CRP.

The use of glycine/HCl or EDTA solutions for the regeneration of apheresis columns, in particular CRP-apheresis columns, is known from the prior art. Bound proteins denature by an abrupt change in pH to the acidic range or the bond between the adsorbed molecule to be removed, here in particular CRP, and the support material of the apheresis column is loosened by the complexation of the binding-mediating cations, in particular calcium. Similar to the administration of EDTA, as elution buffer, citrate-containing solutions are suitable for releasing bound CRP from an apheresis column. No compounds are known from the prior art that enable the separation of bound CRP to be removed from a support material of the apheresis column via a different mechanism.

To test the resistance of the herein described CRP-selective matrix substrate materials to glycine/HCl solutions, the inventors performed 200 regeneration cycles with 7.5 matrix volumes (MV) of glycine/HCl buffer followed by 4 MV of PBS solution (pH 7.4) and 4 MV of NaCl in succession, with no plasma applied to the CRP apheresis columns between the regeneration cycles. CRP binding capacity was thereby tested once before and then once after the 200 successively performed regeneration cycles. It was found that the repeated pH change from 7.4 to 2.8 showed no effect on the CRP binding capacity of the CRP apheresis columns used. There is no reduction in CRP binding capacity due to degradation of the column material or the adsorber by using glycine/HCl pH 2.8 as regeneration solution.

The removal of CRP was investigated on a laboratory scale with columns containing a matrix substrate material selective for CRP with loading of the columns with human plasma. The columns used contained 0.5 g of matrix and 75 mL (150 matrix volumes) of human plasma containing 100, 50, or 10 mg/L CRP was passed through at a flow rate of 1.2 mL/min (corresponding to 17 mL/min in apheresis column scale). The matrix was washed with buffer (0.1 M Tris, 0.2 M NaCl, and 2 mM $CaCl_2$), and the CRP was eluted with elution buffer (EDTA, 0.2 M NaCl, and 0.1 M Tris), and the columns were regenerated with glycine/HCl pH 2.8. The matrix used was found to specifically and selectively bind CRP. When EDTA elution buffer was used, which prevents calcium-dependent binding, CRP was eluted completely. When it was regenerated with glycine/HCl, few other proteins were detected. A decrease in CRP binding capacity after multiple uses of the columns was not observed. Clinical apheresis is performed in cycles that include pre-rinsing the adsorber with 0.9% NaCl buffer, loading the adsorber with plasma, which is returned to the patient, and regenerating the adsorber to prepare it for the next cycle. Except for the plasma, no other solution used is returned to the patient. To study the removal of CRP from blood plasma under clinical conditions, 20 mL of matrix substrate was loaded into a column. This was then pre-rinsed with 200 mL of 0.9% NaCl buffer and then 2.5 L of human plasma at an initial concentration of 100 mg/L CRP was passed through in 5 cycles (1 L/cycle) at a flow rate of 30 mL/min. After each cycle, the apheresis column was regenerated with 35 mL 0.9% NaCl, 50 mL glycine/HCl buffer, 80 mL PBS, and 35 mL 0.9% NaCl. The matrix used contained a phosphocholine ligand for human CRP from plasma that is particularly suitable for therapeutic apheresis. Thus, the matrix binds CRP very selectively and only very low non-specific protein binding of other plasma proteins was observed. CRP binds to phosphocholine and derivatives thereof in a highly specific manner through electrostatic interactions between the ligand and CRP.

In apheresis treatment for the selective removal of CRP from blood plasma, an average of 6000 mL of plasma is treated in 6 to 12 cycles in one treatment session. Processing of 6000 mL of blood plasma usually takes about 4-5 hours including regeneration of the apheresis column. Regeneration was performed using the regeneration solution glycine/HCl buffer as known from prior art. Minimal loss of additional plasma proteins due to CRP apheresis compared to the initial blood concentration can be attributed to the altered loading and regeneration of the adsorber during treatment and is less compared to other extracorporeal methods. Non-specific binding of plasma proteins to the adsorbent matrix is negligible. It has been shown that patients can therefore be treated indefinitely with CRP apheresis, as blood loss is minimal and no side effects have been reported to date.

In therapeutic apheresis for the removal of CRP from blood or blood plasma, the plasma is returned to the patient after passing through the apheresis column. Reusable adsorbers may only be used on one and the same patient. However, when using the apheresis columns in therapeutic apheresis to remove CRP from circulating blood or blood plasma, it has been found by the inventors of the present invention that a protein layer forms around the matrix particles (e.g. agarose particles) during regeneration with glycine/HCl, especially when the patient's blood to be purified contains a high concentration of cell-free DNA/RNA, which can lead to an enhancement of the effect. The formation of the protein layer in the apheresis column masks binding sites and reduces the performance of the apheresis material. The original state cannot be restored with known measures such as further regeneration attempts with a glycine/HCl solution.

As the damage to the apheresis column progresses, the treatment time for the patient increases and so does the suffering of the patient. In addition, the damaged apheresis columns are often no longer usable for further use, so that the treatment costs are considerably increased. Furthermore, the protein layer or protein-DNA as well as protein-RNA layer can lead to a clogging of the fine pores, which increases the system pressure at a constant flow rate. A further increase in the flow rate is accompanied by a further increase in pressure. This can lead to a discontinuation of the treatment. These apheresis columns are also no longer suitable for further use.

In therapeutic apheresis, the substance to be removed, here CRP, is thus removed from the blood or blood plasma of an individual patient. Thus, the composition of the plasma is individual for the patient concerned. Thus, the blood plasma of different patients naturally contains different concentrations of cell-free DNA/RNA. The use of glycine/HCl buffer for regeneration of a CRP apheresis column therefore leads, depending on the patient, to varying degrees to the problems described above, which have been shown to occur with the regeneration with glycine/HCl buffer. It would therefore be particularly advantageous to use a regeneration solution for regeneration that allows complete regeneration of the apheresis column regardless of the concentration of cell-free DNA/RNA in the blood plasma. Furthermore, it would be particularly advantageous for regeneration to use a regeneration solution that improves the reusability of an apheresis column.

For regeneration, it would also be conceivable to use different regeneration solutions that are passed through the apheresis column one after the other for regeneration of the apheresis column. However, an increase in the number of rinsing steps or an increase in the number of different regeneration solutions also leads to an increase in the total duration of the regeneration. Consequently, this also affects the treatment time and increases the suffering time of the patient. While the flow rate during blood purification is limited by the patient's blood flow, in principle the flow rate could be increased during regeneration to speed up the process so that the apheresis column is available for further use. However, a higher flow rate results in a simultaneous increase in pressure on the apheresis and thus on the matrix or column material. Depending on the column material, the shape and strength of the material changes above a certain pressure, thereby reducing the separation performance of the column material, so that the flow rate for the regeneration of an apheresis column depends on the pressure resistance of the column material used. High volume flow rates can compress the matrix, which then results in a lower flow rate. Therefore, it is not possible to regenerate at an arbitrary rate. However, if the volume flow is reduced, the compression is reversible. The regeneration time therefore depends mainly on the volume of the individual rinsing steps and the flow rate, and consequently also on the number of rinsing steps.

It would therefore be particularly advantageous to use a regeneration solution for regeneration which, when used alone, already enables complete regeneration of the apheresis column. By using a single regeneration solution for the regeneration of an apheresis column, the number of rinsing steps can be reduced to the minimum required. In particular, it would be advantageous if the regeneration solution is used to elute the substance to be removed, here CRP, and at the same time is used to return the apheresis column to a therapeutically usable state.

Surprisingly, it has been found that an already used apheresis column, i.e. an apheresis column after treatment for the removal of substances from the blood, can be regenerated with the aid of an alkali hydroxide solution, preferably a sodium hydroxide solution, and the apheresis column regenerated in this way can still be used for apheresis. In particular, apheresis columns can be regenerated in this way which, as a result of their use, have protein deposits and/or protein-DNA and protein-RNA deposits which can no longer be removed by the regeneration solutions used in the prior art and these apheresis columns have thus become unusable.

Therefore, the underlying invention relates to the use of an alkali hydroxide solution, preferably a sodium hydroxide solution, for regeneration of an apheresis column. Formulated differently, the present invention is directed to the use of an alkali hydroxide solution, preferably a sodium hydroxide solution, as a regeneration solution in apheresis. Still differently formulated, the present invention is directed to the use of an alkali hydroxide solution, preferably a sodium hydroxide solution, as a regeneration solution for an apheresis column.

More particularly, the present invention relates to the use of an alkali hydroxide solution, preferably a sodium hydroxide solution, for regeneration of an apheresis column for affinity chromatographic removal of CRP. Thus, the present invention preferably relates to a use of an alkali hydroxide solution for regeneration of an apheresis column, wherein the apheresis column is an apheresis column for affinity chromatographic removal of CRP. The present invention particularly preferably relates to a use of an alkali hydroxide solution for regeneration of an apheresis column, wherein the apheresis column is an apheresis column for affinity chromatographic removal of CRP from blood or blood plasma.

Surprisingly, it has been found that basic regeneration with an alkali hydroxide solution, preferably a sodium hydroxide solution, can also regenerate an already damaged adsorbent matrix in the apheresis column. If only alkali hydroxide solution, preferably sodium hydroxide solution, is used as regeneration means, no acidic protein precipitation can take place. This is an important aspect in restoring the function of an apheresis column. In particular, it has been shown that basic regeneration using an alkali hydroxide solution, preferably a sodium hydroxide solution, can regenerate an already damaged adsorbent matrix in an apheresis column for affinity chromatographic removal of CRP.

Furthermore, the apheresis column may advantageously be stored over an alkali hydroxide solution, preferably a sodium hydroxide solution, as a preservative. In preferred embodiments, the alkali hydroxide solution, preferably the sodium hydroxide solution, can be used to preserve an apheresis column for affinity chromatographic removal of CRP. This makes it possible to make apheresis treatments, including preparation for storage of the apheresis column, as efficient as possible, since time-consuming washing steps of the apheresis column after treatment can be avoided. Alkali hydroxide solution is suitable for preservation of an apheresis column, especially sodium hydroxide solution is perfectly suitable for preservation of apheresis column as it sterilizes very well. Microbial growth is practically excluded.

Thus, a further aspect of the present invention relates to the use of an alkali hydroxide solution, preferably a sodium hydroxide solution, for regeneration and preservation of an apheresis column, preferably an apheresis column for affinity chromatographic removal of CRP. Therefore, the present invention is also directed to the use of an alkali hydroxide solution, preferably a sodium hydroxide solution, for regeneration and preservation of an apheresis column. In other words, the present invention is also directed to the use of an alkali hydroxide solution, preferably a sodium hydroxide solution, as a regeneration solution in apheresis and for preservation of the apheresis column. More preferably, the present invention is directed to the use of an alkali hydroxide solution, preferably a sodium hydroxide solution, as a regeneration solution in apheresis for affinity chromatographic removal of CRP and for preservation of the apheresis column for affinity chromatographic removal of CRP.

In contrast to the means known in the prior art for regeneration of an apheresis column, an alkali hydroxide solution, preferably a sodium hydroxide solution, is characterized by the fact that it is not a chelator for cations. It is assumed that the alkali hydroxide, preferably sodium hydroxide, on the one hand reduces the binding affinity to the support material of the substance to be released and on the other hand denatures possibly bound proteins and thus reduces the binding to the support material. Rapid regeneration allows the column to be returned to a usable state during apheresis treatment. The regeneration of the apheresis column can be performed during an apheresis treatment, but has no influence on the apheresis treatment itself and is therefore not a diagnostic or therapeutic method, but rather a purification method for the apheresis column, which does not involve the apheresis patient, even if the regeneration of the apheresis column takes place during the apheresis treatment.

In a use of an alkali hydroxide solution, preferably a sodium hydroxide solution, according to the invention for regeneration of an apheresis column, preferably an apheresis column for affinity chromatographic removal of CRP, as described herein, the regeneration of the apheresis column can take place during the apheresis treatment. Preferably, in a use of an alkali hydroxide solution, preferably a sodium hydroxide solution, for the regeneration of an apheresis column, as described herein, the regeneration of the apheresis column takes place during the removal of the target compound, particularly CRP. A preferred embodiment of the present invention is thus directed to the use of an alkali hydroxide solution, preferably a sodium hydroxide solution, for the regeneration of an apheresis column, wherein the regeneration takes place during an apheresis treatment.

The present invention therefore also relates to a use of an alkali hydroxide solution for regeneration of an apheresis column, wherein the apheresis column is an apheresis column for the affinity chromatographic removal of CRP, wherein the regeneration occurs during an apheresis treatment. The present invention therefore also relates to a use of an alkali hydroxide solution for regeneration of an apheresis column, wherein the apheresis column is an apheresis column for affinity chromatographic removal of CRP, wherein the regeneration occurs during an apheresis treatment for extracorporeal removal of CRP from blood or blood plasma. The apheresis column is decoupled from the extracorporeal circulation system during regeneration. In other words, the apheresis column is not connected to the extracorporeal circulation system during regeneration. In other words, the apheresis column is not in fluidic connection with the extracorporeal circulation system during regeneration.

Therefore, the present invention also relates to a use of an alkali hydroxide solution for regeneration of an apheresis column, wherein the apheresis column is an apheresis column for affinity chromatographic removal of CRP, wherein the regeneration occurs during an apheresis treatment for extracorporeal removal of CRP from blood or blood plasma, wherein the apheresis column is disconnected from the extracorporeal circulation system during the regeneration.

Therefore, the present invention preferably relates to a use of an alkali hydroxide for regeneration of an apheresis column, wherein the apheresis column is an apheresis column for affinity chromatographic removal of CRP, wherein the regeneration occurs during an apheresis treatment for extracorporeal removal of CRP from blood or blood plasma, wherein the apheresis column is not connected to the extracorporeal circulation system during the regeneration.

Preferably, an alkali hydroxide solution is used to regenerate an apheresis column, wherein the apheresis column is an apheresis column for the affinity chromatographic removal of CRP when blood plasma has been passed through the apheresis column for the removal of CRP prior to regeneration.

Therefore, a use of an alkali hydroxide solution for regenerating an apheresis column is preferred, wherein the apheresis column is an apheresis column for the affinity chromatographic removal of CRP, wherein the apheresis column contains CRP. Preferably, an alkali hydroxide solution is also used to regenerate an apheresis column, wherein the apheresis column is an apheresis column for the affinity chromatographic removal of CRP, wherein the apheresis column is saturated with CRP.

"During an apheresis treatment" or "during the extracorporeal removal of target compounds, in particular CRP from blood", means herein that the regeneration of the apheresis column takes place during the treatment method in the same apheresis device. Thereby, the extracorporeal removal of the target compound, in particular CRP from blood, may be interrupted and the same device may be used to regenerate the apheresis column. Alternatively, regeneration of an apheresis column can be carried out while extracorporeal removal of the target compound, in particular CRP from blood, is continued simultaneously via another apheresis column. The regeneration of the apheresis column takes place in the apheresis device. However, the term "during an apheresis treatment" does not mean that the regeneration and removal of CRP from blood takes place simultaneously on the same apheresis column.

Furthermore, as already mentioned, it was recognized by the inventors that a deposit forms in the apheresis column during regeneration with glycine/HCl (protein layer). If the patient's blood to be purified contains a high concentration of cell-free DNA/RNA, this can lead to an enhancement of the effect. The formation of the deposit in the apheresis column causes the matrix to stick together irreversibly, i.e. the condition cannot be restored with known measures such as further regeneration attempts with a glycine/HCl solution. In cases of deposition of proteins on the column material of the apheresis column up to the formation of a protein layer on the column material of the apheresis column, regeneration of the apheresis column with known measures, such as rinsing with a glycine/HCl solution, is no longer possible, since the protein deposits or the protein layer can no longer be removed with conventional regeneration solutions.

Surprisingly, it has been found that a 0.01 M to 1 M alkali hydroxide solution, preferably a 0.04 M to 0.4 M alkali hydroxide solution, allows to remove the protein deposits preferably completely again. Surprisingly, it has been found that in particular a 0.01 M to 1 M sodium hydroxide solution, preferably a 0.04 M to 0.4 M sodium hydroxide solution, allows to remove the protein deposits preferably completely again. Basic regeneration solutions, e.g. in a pH range of 12-14, are not known in the prior art in connection with the regeneration of CRP apheresis columns.

Therefore, the uses according to the invention preferably refer to a DNA/RNA-containing apheresis column (free DNA or free RNA, respectively), preferably to an apheresis column with a matrix, wherein bound DNA or RNA is present, and more preferably to apheresis columns to which DNA or RNA, respectively, is bound to the ligands of the matrix.

Thus, a preferred embodiment of the present invention relates to the use of an alkali hydroxide solution, preferably a sodium hydroxide solution, to regenerate an apheresis column, preferably an apheresis column for affinity chromatographic removal of CRP, wherein the apheresis column contains DNA and/or RNA deposits, i.e. on the adsorber or as also referred to herein on the adsorber matrix.

The present invention therefore also relates to a use of an alkali hydroxide solution for the regeneration of an apheresis column, wherein the apheresis column is an apheresis column for the affinity chromatographic removal of CRP, wherein the regeneration takes place during an apheresis treatment for the extracorporeal removal of CRP from blood or blood plasma, and wherein the apheresis column is decoupled from the extracorporeal circulation system during the regeneration, wherein the apheresis column contains DNA and/or RNA deposits, i.e. on the adsorber or as also referred to herein on the adsorber matrix.

"Free DNA" or "free RNA", as used herein, refers to deoxyribonucleic acid or ribonucleic acid, respectively, that is located outside of cells. DNA/RNA bound to ligands of the apheresis column is also referred to as free DNA/free RNA, as it is also located outside of cells.

Surprisingly, it has been found that the use of an alkali hydroxide solution to regenerate an apheresis column, preferably an apheresis column for the affinity chromatographic removal of CRP, in addition to restoring the apheresis column to a therapeutically usable state, also allows the simultaneous elution of bound CRP. Therefore, an alkali hydroxide solution is preferably used to regenerate an apheresis column, eluting bound CRP and thereby restoring the apheresis column to a therapeutically usable state. Particularly preferred is the use of an alkali hydroxide solution for the regeneration of an apheresis column, wherein the apheresis column is an apheresis column for the affinity chromatographic removal of CRP, wherein the CRP bound to the apheresis column is eluted by the alkali hydroxide solution. Particularly preferred is therefore the use of an alkali hydroxide solution for the regeneration of an apheresis column, wherein the apheresis column is an apheresis column for the affinity chromatographic removal of CRP, wherein bound CRP is eluted and the apheresis column is simultaneously brought back into a therapeutically usable state.

With the use of an alkali hydroxide solution for the regeneration of an apheresis column, preferably an apheresis column for the affinity chromatographic removal of CRP, and the simultaneous possibility of eluting bound CRP, the use of further regeneration solutions other than the alkali hydroxide solution according to the invention can thus be advantageously omitted. Thus, the use of an alkali hydroxide solution for the regeneration of an apheresis column allows that no additional regeneration with glycine/HCl or EDTA has to be performed to elute the bound CRP from the CRP apheresis column.

In preferred embodiments, no additional regeneration solution is used for regeneration in addition to the alkali hydroxide solution for regeneration of an apheresis column. In preferred embodiments, in addition to the alkali hydroxide solution for regeneration of an apheresis column, no additional elution buffer is used for elution of CRP. The use of an alkali hydroxide solution for regeneration of an apheresis column, preferably an apheresis column for affinity chromatographic removal of CRP, is thus particularly advantageous because the number of rinsing steps for regeneration of the apheresis column does not have to be increased and the overall regeneration time is not extended.

Therefore, a use of an alkali hydroxide solution for regeneration of an apheresis column is preferred, wherein the apheresis column is an apheresis column for affinity chromatographic removal of CRP, wherein no other regeneration solutions are used. Therefore, a use of an alkali hydroxide solution for regeneration of an apheresis column is preferred, wherein the apheresis column is an apheresis column for affinity chromatographic removal of CRP, wherein no glycine/HCl is used for elution or regeneration. Therefore, an alkali hydroxide solution is preferably used for regeneration of an apheresis column, wherein the apheresis column is an apheresis column for affinity chromatographic removal of CRP, wherein no elution buffer or other regeneration solution is used for elution of the bound CRP prior to use of the alkali hydroxide solution. However, this does not exclude herein the prior and subsequent use of rinsing solutions or neutralization solutions such as a NaCl solution or PBS solution.

Regeneration of the apheresis column can take place during the apheresis treatment. In such a case, plasma loss can be minimized by removing the plasma from parts of the apheresis device, in particular from the apheresis column, prior to the introduction of the alkali hydroxide solution, preferably the sodium hydroxide solution, for which purpose a rinsing solution can be used. The alkali hydroxide solution, preferably the sodium hydroxide solution, may further be removed from the apheresis column by a neutralization solution to prepare it for apheresis treatment.

Therefore, a use of an alkali hydroxide solution for the regeneration of an apheresis column is preferred, wherein the apheresis column is an apheresis column for the affinity chromatographic removal of CRP, wherein a rinsing solution is introduced prior to the introduction of the alkali hydroxide solution, and wherein a rinsing solution is introduced after the introduction of the alkali hydroxide solution, or a neutralization solution is introduced followed by a rinsing solution.

Therefore, a use of an alkali hydroxide solution for the regeneration of an apheresis column is preferred, wherein the apheresis column is an apheresis column for the affinity chromatographic removal of CRP, wherein a rinsing solution is introduced into the apheresis column prior to the introduction of the alkali hydroxide solution. The rinsing solution is preferably a sodium chloride solution, in particular a physiological sodium chloride solution or a PBS solution (phosphate buffered saline). Preferably a NaCl solution and particularly preferably a physiological NaCl solution are used as rinsing solution.

Therefore, a use of an alkali hydroxide solution for the regeneration of an apheresis column is preferred, wherein the apheresis column is an apheresis column for the affinity chromatographic removal of CRP, wherein a rinsing solution is introduced after the introduction of the alkali hydroxide solution. The rinsing solution is preferably a sodium chloride solution in particular a physiological sodium chloride solution or a PBS solution (phosphate buffered saline). A NaCl solution and particularly preferably a physiological NaCl solution is preferably used as rinsing solution.

Therefore, a use of an alkali hydroxide solution for the regeneration of an apheresis column is preferred, wherein the apheresis column is an apheresis column for the affinity chromatographic removal of CRP, wherein after the introduction of the alkali hydroxide solution, a neutralization solution and subsequently a rinsing solution are introduced. The rinsing solution is preferably a sodium chloride solution, in particular a physiological sodium chloride solution or a PBS solution (phosphate buffered saline). The rinsing solution is preferably a NaCl solution and particularly preferably a physiological NaCl solution. Neutralization solutions are preferably selected from the group comprising or consisting of a PBS solution or NaCl solution or citrate solution. Particularly preferably, the neutralization solution is a citrate solution.

Particularly preferably, the rinsing solution is not an elution buffer for removing the bound CRP. Particularly preferably, the rinsing solution is further not a regeneration solution. In other words, it is particularly preferred that the rinsing solution is not a glycine/HCl buffer. It is further preferred that no regeneration solution other than the alkali hydroxide solution is used to regenerate the apheresis column. It is therefore preferred that no further regeneration solution is introduced before the introduction of the rinsing solution and after the introduction of the alkali hydroxide solution and after the subsequent introduction of rinsing solution or neutralization solution and rinsing solution.

Therapeutic apheresis is performed in cycles, alternating between loading and regeneration of the apheresis column. It is preferred that the alkali hydroxide solution is used as the regeneration solution in each regeneration cycle. It is further preferred that the alkali hydroxide solution is thereby used as the sole regeneration solution.

Therefore, the repeated use of an alkali hydroxide solution for the regeneration of an apheresis column is preferred, wherein the apheresis column is an apheresis column for the affinity chromatographic removal of CRP. Therefore, the use of an alkali hydroxide solution for the regeneration of an apheresis column is preferred, wherein the apheresis column is an apheresis column for the affinity chromatographic removal of CRP, wherein the alkali hydroxide solution is used repeatedly to regenerate the apheresis column. Therefore, the use of an alkali hydroxide solution for the regeneration of an apheresis column is preferred, wherein the apheresis column is an apheresis column for the affinity chromatographic removal of CRP, wherein the alkali hydroxide solution is used in each regeneration cycle to regenerate the apheresis column.

An advantage of the use of an alkali hydroxide solution, preferably the use of a sodium hydroxide solution, for regeneration of an apheresis column, preferably an apheresis column for affinity chromatographic removal of CRP, is based on that with the use of the alkali hydride solution the number of rinsing steps for regeneration of the apheresis column does not have to be increased compared to the prior art use of a glycine/HCl buffer, since the alkali hydroxide solution can advantageously be used for elution of the bound CRP and simultaneously for removal of further substances. Another advantage is that with the use of an alkali hydroxide solution to regenerate an apheresis column, acidic protein folding no longer occurs and the problems that have been shown to occur when using the glycine/HCl buffer to regenerate an apheresis column do not occur. Thus, the use of the alkali hydroxide solution to regenerate the apheresis column significantly improves the reusability of the apheresis column. It has been shown that the CRP adsorbers can be regenerated in 200 cycles with sodium hydroxide solution without any degradation in performance.

Therefore, a use of an alkali hydroxide solution to regenerate an apheresis column is preferred, wherein the apheresis column is an apheresis column for affinity chromatographic removal of CRP, wherein the apheresis column can be reused at least 50 times, preferably at least 100 times, more preferably at least 150 times, and most preferably at least 200 times.

Regeneration Solution

Glycine-HCl solutions for use as regeneration solutions are known from the prior art. The glycine/HCl solution have a pH value in the range of 2-3 e.g. pH=2.8. The concentration of the glycine-HCl solution can range from 0.1 M to 1 M. To prepare a glycine-HCl solution or used synonymously a glycine-hydrochloric acid buffer, 15.01 g of glycine is dissolved in one liter of water and 25% hydrochloric acid is added. The pH can be adjusted using hydrochloric acid or sodium hydroxide. The preparation of the glycine-HCl solution is known to the skilled person.

"Sodium hydroxide solution" herein means a solution comprising sodium hydroxide in a solvent such as water or alcohol such as methanol, ethanol, propanol, etc., or in a solvent mixture of water and at least one alcohol. Preferably, it is a solution comprising or consisting of sodium hydroxide in water. Thus, an aqueous sodium hydroxide solution (also referred to as $NaOH_{aq}$) is preferred.

Sodium hydroxide is available in various degrees of purity, preferably a purity of 98%, more preferably 99%, more preferably 99.5%, more preferably 99.9% and most preferably 99.99%. A degree of purity of 98% to 100% is preferred.

In principle, the sodium hydroxide in the sodium hydroxide solution can be present in all available concentrations (based on sodium hydroxide in a solvent or solvent mixture). Usually, the solution is an aqueous sodium hydroxide solution. However, it is preferred that the concentration of sodium hydroxide in the sodium hydroxide solution is in a range from 0.005 mol/l to 1.0 mol/l, still further preferred between 0.01 mol/l to 1.0 mol/l, still further preferred between 0.02 mol/l to 0.80 mol/l, still further preferred between 0.03 mol/l to 0, 60 mol/l, still further preferred between 0.04 mol/l to 0.50 mol/l, still further preferred between 0.05 mol/l to 0.40 mol/l, still further preferred between 0.06 mol/l to 0.30 mol/l, still further preferred between 0.07 mol/l to 0.20 mol/l, still further preferred between 0.08 mol/l to 0.10 mol/1.

A preferred embodiment of the present invention relates to the use of an alkali hydroxide solution, preferably a sodium hydroxide solution, for regeneration of an apheresis column, wherein the concentration of alkali hydroxide, preferably sodium hydroxide, in the solution is in a range of 0.01 1.0 mol/1.

Another preferred embodiment of the present invention relates to the use of an alkali hydroxide solution, preferably a sodium hydroxide solution, for the regeneration of an apheresis column, wherein the concentration of alkali hydroxide, preferably sodium hydroxide in the solution is in a range of 0.05-0.20 mol/l, preferably of 0.05-0.10 mol/l, more preferably of 0.07-0.10 mol/1.

The basic pH of the alkali hydroxide solution, preferably the sodium hydroxide solution, is not limited. Preferably, the alkali hydroxide solution, preferably the sodium hydroxide solution, has a pH in a range from pH 7 to 14, more preferably from 7.5-14, more preferably from 8.0 to 14.0, more preferably from 8.5 to 14, more preferably from 9.0 to 14.0, more preferably from 9.5 to 14.0, more preferably from 10.5 to 14.0, more preferably from 11 to 14.0, more preferably from 11.5 to 14.0, more preferably from 12 to 14.0, more preferably from 12.5 to 14.0, and even more preferably from 13 to 14. Particularly preferably, a sodium hydroxide solution has a pH from 12 to 13.7.

Thus, an embodiment of the present invention is the use of an alkali hydroxide solution, preferably a sodium hydroxide solution, for regeneration of an apheresis column, wherein the alkali hydroxide solution, preferably the sodium hydroxide solution, has a pH in a range of 12 to 14.

Also preferred is a use of an alkali hydroxide solution for regeneration of an apheresis column, wherein the apheresis column is an apheresis column for affinity chromatographic removal of CRP, wherein the alkali hydroxide solution, preferably the sodium hydroxide solution, has a pH in a range of 12 to 14, more preferably a pH of 12 to 13.7.

The term "alkali hydroxide solution" or alternatively "alkali metal hydroxide solution" as used herein, means a "lithium hydroxide solution", "sodium hydroxide solution", "potassium hydroxide solution" or a mixture of two or three of the foregoing.

"Lithium hydroxide solution" herein means a solution comprising lithium hydroxide in a solvent such as water or alcohol such as methanol, ethanol, propanol, etc., or in a solvent mixture of water and at least one alcohol. Preferably, it is a solution comprising or consisting of lithium hydroxide in water.

"Potassium hydroxide solution" herein means a solution comprising potassium hydroxide in a solvent such as water or alcohol such as methanol, ethanol, propanol, etc. or in a solvent mixture of water and at least one alcohol. Preferably, it is a solution comprising or consisting of potassium hydroxide in water.

In principle, the lithium hydroxide in the lithium hydroxide solution or the potassium hydroxide in the potassium hydroxide solution can be present in all available concentrations (based on lithium hydroxide in a solvent or solvent mixture or based on potassium hydroxide in a solvent or solvent mixture). However, a concentration of the lithium hydroxide in the lithium hydroxide solution or of the potassium hydroxide in the potassium hydroxide solution is preferably in a range from 0.005 mol/l to 1.0 mol/l, still more preferably between 0.01 mol/l to 1.0 mol/l, still more preferably between 0.02 mol/l to 0.80 mol/l, still more preferably between 0.03 mol/l to 0.60 mol/l, still further preferably between 0.04 mol/l to 0.50 mol/l, still further preferably between 0.05 mol/l to 0.40 mol/l, still further preferably between 0.06 mol/l to 0.30 mol/l, still further preferably between 0.07 mol/l to 0.20 mol/l, still further preferably between 0.08 mol/l to 0.10 mol/l.

If two of the aforementioned three alkali hydroxide solutions are used, the cumulative concentration of the two alkali hydroxide solutions should be within a range of 0.005 mol/l to 1.0 mol/l, still further preferably between 0.01 mol/l to 1.0 mol/l, still further preferably between 0.02 mol/l to 0.80 mol/l, still further preferably between 0.03 mol/l to 0.60 mol/l, still further preferably between 0.04 mol/l to 0.50 mol/l, still further preferably between 0.05 mol/l to 0.40 mol/l, still further preferably between 0.06 mol/l to 0.30 mol/l, still further preferably between 0.07 mol/l to 0.20 mol/l, still further preferably between 0.08 mol/l to 0.10 mol/1. This means, for example, that the concentration of potassium hydroxide in the solution is, for example, 0.06 mol/l and of sodium hydroxide in the same solution is, for example, 0.08 mol/l, resulting in the cumulative alkali hydroxide concentration in the solution of 0.14 mol/1. The same applies if all three aforementioned alkali hydroxides are used in one solution, for example lithium hydroxide at 0.04 mol/l, potassium hydroxide at 0.02 mol/l and sodium hydroxide at 0.05 mol/l, so that the cumulative alkali hydroxide concentration in the solution is 0.11 mol/1.

Thus, an embodiment of the present invention relates to the use of an alkali hydroxide solution selected from a group comprising or consisting of sodium hydroxide solution, lithium hydroxide solution, and/or potassium hydroxide solution for regeneration of an apheresis column.

However, the use of a sodium hydroxide solution for regeneration of an apheresis column is particularly preferred.

In addition, the alkali hydroxide solutions are capable of regenerating adsorbers on which protein deposits have already formed, which can no longer be removed by conventional regeneration means.

Therefore, a use of an alkali hydroxide solution for the regeneration of an apheresis column is preferred, wherein the apheresis column is an apheresis column for the affinity chromatographic removal of CRP, wherein the regeneration occurs when protein deposits can no longer be removed by conventional regeneration means. Therefore, a use of an alkali hydroxide solution for regeneration of an apheresis column is preferred, wherein the apheresis column is an apheresis column for affinity chromatographic removal of CRP, wherein regeneration occurs when protein deposits are no longer removable by regeneration means such as glycine-HCl or EDTA.

Apheresis Column

How an apheresis column (or cartridge) can be designed or constructed in principle is part of the state of the art and can be derived from EP 0237659 B1. The exact dimensions of the column or cartridge used according to the invention (as a device for the selective removal of the target compound, in particular of CRP) depend here to a large extent on the intended use of the device according to the invention. The apheresis column generally comprises a housing, e.g. in form of a cartridge, which is in fluidic connection with an extracorporeal circulation system via at least one inlet and at least one outlet and which contains a matrix for affinity chromatographic or adsorptive removal of the target compound, in particular CRP.

"Target compound" herein refers to the substance that is to be removed from blood by means of apheresis, i.e. the substance that is supposed to bind to the matrix during apheresis. Particularly preferably, the target compound to be removed from blood or blood plasma by means of apheresis is herein CRP.

The matrix for affinity chromatographic (or adsorptive) removal of the target compound, in particular CRP, comprises a matrix substrate material (column material) to which, in turn, compounds (ligands) are bound which have the property of specifically binding the target compound, in particular CRP. According to a preferred embodiment of the present invention, the matrix is integrated into or immobilized in the apheresis column for affinity chromatographic removal of the target compound, in particular CRP, in such a way that it cannot be flushed out of the column with the flow of blood plasma. Depending on the embodiment, this can be realized, for example, in the form of filters at the inlet and outlet of the device.

The use according to the invention is utilized in particular for the regeneration of apheresis columns for affinity chromatographic removal of CRP.

In principle, all inert chromatography or column materials are suitable as matrix substrate materials (column material) for the production of the matrix, which in particular do not react with blood or blood plasma or alter or contaminate blood or blood plasma in such a way that the blood or blood plasma can no longer be returned to a patient after contacting the matrix. Suitable matrix substrate materials according to the invention therefore include, but are not limited to Eupergit®, polyvinylpyrrolidone, methacrylate, methacrylate resins, agarose, cross-linked agarose such as Sepharose® (Separation-Pharmacia-Agarose), acrylic beads, cellulose matrices, ceramic matrices, glass beads and/or solid-phase silica or mixtures and/or derivatives of these substances. Preferably, the matrix substrate material is selected from the group comprising or consisting of agarose and sepharose. Particularly preferably, the matrix substrate material is agarose. The solid-phase silica matrix may comprise virtually any form of particulate silica, including amorphous silicas such as colloidal silica, silica gels, precipitated silicas, and fumed or pyrogenic silicas; microcrystalline silicas such as diatomaceous earth; and crystalline silicas such as quartz.

While the flow rate during blood purification is limited by the patient's blood flow, the flow rate could in principle be increased during regeneration to accelerate the process so that the apheresis column is available for further use. However, a higher flow rate results in a simultaneous increase in pressure on the apheresis column and thus on the matrix or column material. Depending on the column material, the shape and strength of the material changes above a certain pressure, thereby reducing the separation performance of the column material, so that the flow rate for the regeneration of an apheresis column depends on the pressure resistance of the column material used.

Herein, it was found that the use of an alkali hydroxide solution, preferably a sodium hydroxide solution, not only allows higher pressures, but even such high pressures can be used that flow rates are possible which allow purification of the apheresis column in only a few minutes or seconds. In particular, a combination of an alkali hydroxide solution, preferably a sodium hydroxide solution, with agarose and derivatives thereof is suitable for rapid regeneration. Therefore, an embodiment of the underlying invention relates to the use of an alkali hydroxide solution, preferably a sodium hydroxide solution, for regeneration of an apheresis column, wherein the apheresis column contains agarose and its derivatives. Agarose or cross-linked agarose such as Sepharose® is particularly preferred. The fast regeneration time can ensure that the patient's treatment time and thus the suffering time is greatly reduced.

Matrix Substrate Materials

According to the invention, the compounds (ligands) bound to the matrix substrate materials, which have the property to specifically bind the target compound, in particular CRP, are selected from the group comprising or consisting of lipids, lysophospholipids, lysophosphatidylcholine, peptides, peptides with charged amino acids, peptides containing the sequence ArgProArg, phosphocholine, derivatives of phosphocholine, DNA, DNA derivatives, RNA, RNA derivatives, L-ribonucleic acid aptamers, such as Spiegelmers® (an RNA-like molecule consisting of L-ribose units), glycosides, saccharides and aptamers.

In some embodiments, the bound compounds are preferably not glycosides or saccharides. According to the invention, the bound compounds are not proteins. Therefore, the compounds (ligands) bound to the matrix substrate materials having the property of specifically binding the target compound, in particular CRP, are preferably selected from the group comprising or consisting of lipids, lysophospholipids, lysophosphatidylcholine, peptides, peptides with charged amino acids, peptides containing the sequence ArgProArg, phosphocholine, derivatives of phosphocholine, DNA, DNA derivatives, RNA, RNA derivatives, L-ribonucleic acid aptamers such as Spiegelmers® (an RNA-like molecule consisting of L-ribose units) and aptamers.

In a use of an alkali hydroxide solution, preferably a sodium hydroxide solution, for regeneration of an apheresis column according to the invention, as described herein, the apheresis column is therefore preferably a CRP apheresis column.

Thus, an embodiment of the present invention relates to the use of an alkali hydroxide solution, preferably a sodium hydroxide solution, for regeneration of an apheresis column, wherein the apheresis column is a CRP apheresis column. Moreover, a further embodiment of the present invention relates to the use of an alkali hydroxide solution, preferably a sodium hydroxide solution, for the regeneration of an apheresis column for the affinity chromatographic removal of CRP.

Moreover, a further embodiment of the present invention relates to the use of an alkali hydroxide solution, preferably a sodium hydroxide solution, for regeneration of an apheresis column, wherein the apheresis column is a CRP apheresis column and the regeneration occurs during the removal of CRP from blood.

In addition, a further embodiment of the present invention relates to the use of an alkali hydroxide solution, preferably a sodium hydroxide solution, for regeneration of an apheresis column for affinity chromatographic removal of CRP, wherein the regeneration occurs during the removal of CRP from blood.

$Ca^{2+}$-Dependent Ligands for CRP

For affinity chromatographic removal of CRP from biological fluids, e.g. blood or blood plasma, a column material containing phosphocholine and/or phosphoethanolamine or derivatives thereof may be used, allowing $Ca^{2+}$-dependent binding of CRP to said functionalized column material.

For this purpose, phosphocholine, phosphoethanolamine or derivatives thereof are immobilized on a column material. This is usually done via an organic linker group, through which the phosphocholine, phosphoethanolamine or derivatives thereof are adsorptively or even more preferably covalently linked to the column material. This results in a so-called "functionalized column material" (functionalized matrix substrate material), whereby the chemical group responsible for the $Ca^{2+}$-dependent binding of CRP is exposed to the outside, so that CRP present in a biological fluid has access to said chemical group.

In other words, the term "functionalized column material", as used herein, refers to a column material for affinity chromatography which is provided with a functional chemical group (ligand). Here, the functional chemical group may be linked to the column material via adsorptive or ionic interactions but preferably via a covalent bond. It is of course of importance that the functional chemical group (ligand) is connected to the column material in such a way that the functional group is active and exposed so that its functionality is maintained. Hereby, it is possible that the group attached to the column material (here: ω-Phosphonooxyalkylammonium group and/or ω-Ammoniumalkoxy-hydroxy-phosphoryloxy group) attached to the column material can interact with or bind a target compound (here CRP) from the sample (here: biological fluid such as blood or blood plasma).

Depending on whether the phosphocholine, phosphoethanolamine or a derivative thereof is linked to the column material via the ammonium group or via the phosphate group via an organic linker, a distinction is made between a column material functionalized with a ω-phosphonooxyalkylammonium group (linkage via the ammonium group) and a column material functionalized with an w-ammoniumalkoxy-hydroxy-phosphoryloxy group (linkage via the phosphate group).

Therefore, a preferred embodiment of the present invention is the use of an alkali hydroxide solution, preferably a sodium hydroxide solution, for regeneration of an apheresis column, wherein the apheresis column comprises a matrix substrate material functionalized with at least one ω-phosphonooxyalkylammonium group and/or with at least one ω-ammoniumalkoxy-hydroxy-phosphoryloxy group.

The linkage to the column material (optionally via an organic linker) is shown in formulas (I) and (II) below via a dashed line at either the nitrogen atom of the ammonium group or the oxygen atom of the phosphate group.

The term "ω-phosphonooxyalkyl ammonium group", as used herein, may be used synonymously with "omega-phosphonooxyalkyl ammonium" and describes compounds of the following general formula (I)

(I)

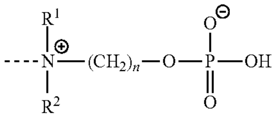

wherein n is selected from 2 and 3;

$R^1$ and $R^2$ are independently of each other selected from: —H, —$CH_3$, —$C_2H_5$, —$C_3H_7$, —$C_4H_9$, —$C_5H_{11}$, —$C_6H_{13}$, or $R^1$ and $R^2$ together with the nitrogen atom to which they are attached can form a heterocycle selected from:

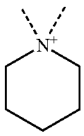, 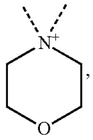, 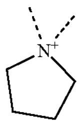, wherein one or more hydrogen atom(s) can be replaced by (a) fluorine atom(s).

Therefore, an embodiment of the present invention is directed to the use of an alkali hydroxide solution, preferably a sodium hydroxide solution, for regeneration of an apheresis column, wherein the apheresis column comprises a matrix substrate material functionalized with at least one ω-phosphonooxyalkylammonium group represented by the following general formula (I):

(I)

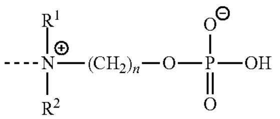

wherein n is selected from 2 and 3;

$R^1$ and $R^2$ are independently of each other selected from: —H, —$CH_3$, —$C_2H_5$, —$C_3H_7$, —$C_4H_9$, —$C_5H_{11}$, —$C_6H_{13}$, or $R^1$ and $R^2$ together with the nitrogen atom to which they are attached can form a heterocycle selected from:

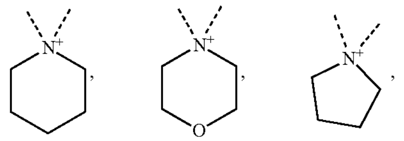

wherein one or more hydrogen atom(s) can be replaced by (a) fluorine atom(s).

Preferably, the at least one ω-phosphonooxyalkylammonium group corresponds to a group of the general formula (I)

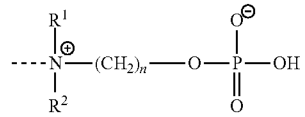
(I)

wherein n=2 or 3;

$R^1$ and $R^2$ are independently of each other selected from: —H, —$CH_3$, —$C_2H_5$, —$C_3H_7$, or $R^1$ and $R^2$ together with the nitrogen atom to which they are attached can form a heterocycle selected from:

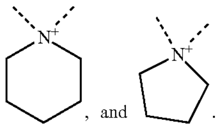

Particularly preferably, the at least one ω-phosphonooxyalkyl ammonium group corresponds to a group of the general formula (I)

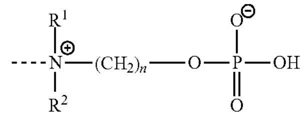
(I)

wherein n=2;

$R^1$ and $R^2$ are selected from: —H, —$CH_3$, —$C_2H_5$, and particularly preferably from —$CH_3$ and —$C_2H_5$ or $R^1$ and $R^2$ together with the nitrogen atom to which they are attached can form a heterocycle selected from:

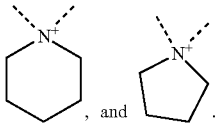

Preferred compounds containing a ω-phosphonooxyalkyl ammonium group as described above and which are suitable for the functionalization of a corresponding column material (matrix substrate material) comprise, for example: 2-[2-(2-aminoethoxy)ethyl-diethyl-ammonio]ethyl hydrogen phosphate, 2-[4-[2-(2-aminoethoxy)ethyl]morpholin-4-ium-4-yl]ethyl hydrogen phosphate, 2-[1-[2-(2-aminoethoxy)ethyl]piperidin-1-ium-1-yl]ethyl hydrogen phosphate, 2-[2-(2-aminoethoxy)ethyl-dimethyl-ammonio]ethyl hydrogen phosphate, 2-[3-aminopropyl-(dimethyl)ammonio]ethyl hydrogen phosphate, 2-[dimethyl(4-sulfanylbutyl)ammonio]ethyl hydrogen phosphate, 2-[4-azidobutyl(dimethyl)ammonio]ethyl hydrogen phosphate, 2-[dimethyl(pent-4-ynyl)ammonio]ethyl hydrogen phosphate, 2-[3-(6-aminohexanoyl-amino)propyl-diethyl-ammonio]ethyl hydrogen phosphate, 2-[1-[2-[2-(6-aminohexanoyl-amino)ethoxy]ethyl]piperidin-1-ium-1-yl]ethyl hydrogen phosphate, 2-[4-[2-[3-(6-aminohexanoylamino)propanoylamino]ethoxy]ethyl]morpholin-4-ium-4-yl]ethyl hydrogen phosphate, 2-[1-[2-[2-[6-(6-aminohexanoylamino)hexanoylamino]ethoxy]ethyl]pyrrolidin-1-ium-1-yl]ethyl hydrogen phosphate, 2-[2-allyloxyethyl(dimethyl)ammonio]ethyl hydrogen phosphate, 2-[2-allyloxyethyl(diethyl)ammonio]ethyl hydrogen phosphate, 2-[4-(2-allyloxyethyl)morpholin-4-ium-4-yl]ethyl hydrogen phosphate, 2-[1-(2-allyloxyethyl)piperidin-1-ium-1-yl]ethyl hydrogen phosphate, 2-[2-[2-(6-aminohexanoylamino)ethoxy]ethyl dimethyl-ammonio]ethyl hydrogen phosphate, 2-[2-[2-[3-(6-aminohexanoylamino)propanoylamino]ethoxy]¬ethyl-dimethyl-ammonio]ethyl hydrogen phosphate, 2-[3-azidopropyl(dimethyl)ammonio]ethyl hydrogen phosphate, 2-[dimethyl-[2-[2-(prop-2-ynoxycarbonylamino)ethoxy]ethyl]ammonio]ethyl hydrogen phosphate, 2-[2-[2-(allyloxycarbonylamino)ethoxy]ethyl dimethyl-ammonio]ethyl hydrogen phosphate, 2-[2-[2-[6-(allyloxycarbonylamino)hexanoylamino]ethoxy]ethyl dimethyl-ammonio]ethyl hydrogen phosphate, 2-[2-(6-aminohexanoylamino)ethyl-dimethyl-ammonio]ethyl hydrogen phosphate, 2-[dimethyl-[3-[6-(prop-2-ynoxycarbonylamino)hexanoylamino]propyl]ammonio]ethyl hydrogen phosphate, and 2-[3-(6-aminohexanoylamino)propyl-dimethyl-ammonio]ethyl hydrogen phosphate.

The term "ω-ammoniumalkoxy-hydroxy-phosphoryloxy groups", as used herein, can be used similarly as "omega-ammoniumalkoxy-hydroxy-phosphoryloxy groups" and describes compounds of the following general formula (II)

(II)
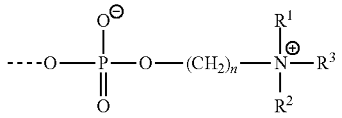

wherein n is selected from 2 and 3;

$R^1$, $R^2$ and $R^3$ are independently of each other selected from: —H, —$CH_3$, —$C_2H_5$, —$C_3H_7$, —$C_4H_9$, —$C_5H_{11}$, —$C_6H_{13}$, or $R^1$ and $R^2$ together with the nitrogen atom to which they are attached can form a heterocycle selected from:

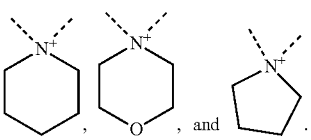

and $R^3$ is selected from: —H, —$CH_3$, —$C_2H_5$, —$C_3H_7$, —$C_4H_9$, —$C_5H_{11}$, —$C_6H_{13}$, and preferably —H;

wherein one or more hydrogen atom(s) can be replaced by (a) fluorine atom(s).

Preferred "ω-ammoniumalkoxy-hydroxy-phosphoryloxy groups" comprise compounds of the general formula (II)

(II)

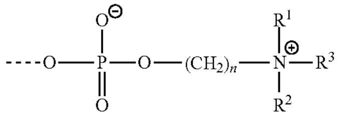

wherein n is selected from 2 and 3;

$R^1$, $R^2$ and $R^3$ are independently of each other selected from: —H, —$CH_3$, —$C_2H$, —$C_3H_7$, or $R^1$ and $R^2$ together with the nitrogen atom to which they are attached can form a heterocycle selected from:

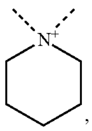,
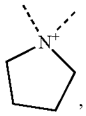, and $R^3$=—H.

Within the scope of the present invention, it is particularly preferred if the ω-ammoniumalkoxy-hydroxy-phosphoryloxy group is an ω-trialkylammoniumalkoxy-hydroxy-phosphoryloxy group.

Therefore, particularly preferred ω-ammoniumalkoxy-hydroxy-phosphoryloxy groups comprise compounds of the general formula (II)

(II)

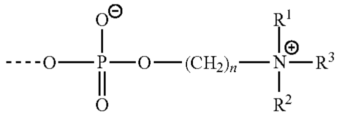

wherein n=2;

and $R^1$, $R^2$ and $R^3$ are selected from: —H, —$CH_3$, —$C_2H_5$ and particularly preferably from —$CH_3$ and —$C_2H_5$.

It is also particularly preferred if the ω-ammoniumalkoxy-hydroxy-phosphoryloxy groups are ω-trimethylammoniumethoxy-hydroxy-phosphoryloxy groups or ω-trimethylammoniumpropoxy-hydroxy-phosphoryloxy groups.

Preferred compounds containing an ω-ammoniumalkoxy-hydroxy-phosphoryloxy group as described above and which are suitable for the functionalization of a corresponding column material comprise for example: p-aminophenylphosphocholine (APPC), 4-[[hydroxy[2-(trimethylammonio)ethoxy]phosphinyl]oxy]benzenediazonium(p-diazonium phenylphosphocholine) or p-nitrophenyl 6-(O-phosphocholine)hydroxyl-hexanoate.

A preferred embodiment therefore relates to the use of an alkali hydroxide solution, preferably a sodium hydroxide solution, for the regeneration of an apheresis column, wherein the apheresis column comprises a matrix material functionalized with at least one ω-ammoniumalkoxy-hydroxy-phosphoryloxy group corresponding to a group of the following general formula (II):

(II)

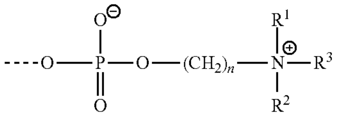

wherein n is selected from 2 and 3;

$R^1$, $R^2$ and $R^3$ are independently of each other selected from: —H, —$CH_3$, —$C_2H$, —$C_3H_7$, —$C_4H_9$, —$C_5H_{11}$, —$C_6H_{13}$, or $R^1$ and $R^2$ together with the nitrogen atom to which they are attached can form a heterocycle selected from:

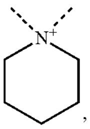,
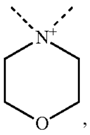, and
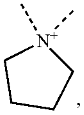, and $R^3$ is selected from: —H, —$CH_3$, —$C_2H_5$, —$C_3H_7$, —$C_4H_9$, —$C_5H_{11}$, —$C_6H_{13}$, and preferably —H;

wherein one or more hydrogen atom(s) can be replaced by (a) fluorine atom(s).

A further aspect of the present invention relates to a method for regeneration of an apheresis column for affinity chromatographic removal of CRP comprising the steps:

(I) introduction of an alkali hydroxide solution, preferably a sodium hydroxide solution, into an apheresis column for regeneration of the apheresis column.

The alkali hydroxide solution, preferably the sodium hydroxide solution, may be removed from the apheresis column by a neutralization solution for preparation of the apheresis column for apheresis treatment. Thus, the methods according to the present invention may comprise a step (II) introduction of a neutralization solution.

Therefore, an embodiment of the present invention relates to a method for regeneration of an apheresis column for affinity chromatographic removal of CRP comprising the steps:

(I) introduction of an alkali hydroxide solution, preferably a sodium hydroxide solution, into an apheresis column for regeneration of the apheresis column; and (II) introduction of a neutralization solution.

Therefore, an embodiment of the present invention relates to a method for regeneration of an apheresis column for affinity chromatographic removal of CRP comprising the steps:

(I) introduction of an alkali hydroxide solution, preferably a sodium hydroxide solution, into an apheresis column for regeneration of the apheresis column;

(II') stopping the introduction of the alkali hydroxide solution, preferably the sodium hydroxide solution, after step (I), and (II) introduction of a neutralization solution.

Regeneration of the apheresis column can take place during the apheresis treatment. In such a case, plasma loss can be minimized by removing the plasma from parts of the apheresis device, in particular from the apheresis column, prior to the introduction of the alkali hydroxide solution, preferably the sodium hydroxide solution, for which purpose a rinsing solution can be used. Thus, the methods according to the present invention may comprise a step (I') rinsing the apheresis column preferably containing blood plasma.

Thus, an embodiment of the present invention relates to a method for regeneration of an apheresis column for affinity chromatographic removal of CRP comprising the steps:

(I') introduction of a rinsing solution into an apheresis column preferably containing blood plasma;

(I) introduction of an alkali hydroxide solution, preferably a sodium hydroxide solution, into the apheresis column for regeneration of the apheresis column;

(II') stopping the introduction of the alkali hydroxide solution, preferably the sodium hydroxide solution, after step (I); and (II) introduction of a neutralization solution.

Rinsing Solution

The rinsing solution can, but does not have to, serve for regeneration of the apheresis column, but in addition to the above-mentioned function, has the task of displacing the blood plasma from the apheresis column or contributing to the neutralization of the apheresis column matrix. As rinsing solution, a sodium chloride solution, in particular a physiological sodium chloride solution or a PBS solution (phosphate buffered saline) can be applied. Preferably, a NaCl solution and particularly preferably a physiological NaCl solution is used as the rinsing solution.

The term "NaCl solution" (sodium chloride solution), as used herein, comprises aqueous solutions containing sodium chloride (i.e. NaCl, also referred to as table salt) as the main component. "Major constituent" as used herein means that the molar concentration of sodium chloride in the NaCl solution is greater than the respective molar concentration of all other compounds within the NaCl solution, but excluding water. Preferably, the NaCl solution comprises 0.1 to 5 wt % sodium chloride, particularly preferably 0.9 wt %. Preferably, the rinsing solution is such a NaCl solution. A physiological NaCl solution (PBS solution) is understood to be a sodium chloride solution comprising water and 0.9 wt % sodium chloride (NaCl).

Neutralization Solution

The term "neutralization solution", as used herein, refers to an aqueous solution which serves to adjust a pH range from 6.5 to 7.6, preferably from 7.30 to 7.50 and more preferably from 7.35 to 7.45.

In principle, all aqueous solutions can be considered as neutralization solutions that are allowed to be used in the medical field. Preferably, the aqueous solution has a pH≤7, i.e. the aqueous solution may have a neutral pH or a pH<7. Preferred neutralization solutions are selected from the group comprising or consisting of a PBS solution or a NaCl solution or a citrate solution. Particularly preferably, the neutralization solution is a citrate solution. Thus, another aspect of the present invention is directed to the use of a citrate solution for neutralizing an apheresis column comprising a column material, wherein the column material is in a basic medium. Thus, the methods according to the present invention may comprise a step (II) introduction of a neutralization solution, wherein the neutralization solution is a PBS, NaCl or citrate solution, preferably a citrate solution.

Moreover, an embodiment of the present invention is directed to a method for regeneration of an apheresis column for affinity chromatographic removal of CRP comprising the steps:

(I) introduction of an alkali hydroxide solution, preferably a sodium hydroxide solution, into the apheresis column for regeneration of the apheresis column;

(II') stopping the introduction of the alkali hydroxide solution, preferably the sodium hydroxide solution, after step (I); and (II) introduction of a PBS solution or NaCl solution or citrate solution.

The term "citrate solution" as used herein comprises aqueous solutions containing at least one citrate compound.

The term "citrate", as used herein, refers to the citrate anion, which is the salt of citric acid. Preferably, the citrate solution contains at least one of the citrate compounds selected from the group comprising or consisting of citric acid, sodium dihydrogen citrate, disodium hydrogen citrate, trisodium citrate, trisodium citrate dihydrate, potassium dihydrogen citrate, dipotassium hydrogen citrate, tricalcium citrate, lithium dihydrogen citrate, dilithium hydrogen citrate, trilithium citrate, ammonium dihydrogen citrate, diammonium hydrogen citrate, triammonium citrate, tricalcium dicitrate (calcium citrate), trimagnesium dicitrate (magnesium citrate) and/or partial citrate esters.

A citrate solution consisting of citric acid, trisodium citrate, D-glucose and water is also referred to as "acid citrate dextrose solution (ACD solution)". Preferred variants of the citrate solution used according to the invention concern ACD solutions containing between 22.9 mM and 38.0 mM citric acid, between 44.9 mM and 74.8 mM trisodium citrate, between 74.2 mM and 123.6 mM D glucose and water. A particularly preferred variant of the citrate solution used according to the invention concerns an ACD solution containing 38 mM citric acid, 74.8 mM trisodium citrate, 123.6 mM D glucose and water. This citrate solution is also referred to as "ACD-A solution."

A citrate solution consisting of citric acid, trisodium citrate, sodium hydrogen phosphate, D-glucose and water is also referred to as "citrate-phosphate-dextrose solution (CPD)". A citrate solution consisting of citric acid, trisodium citrate, sodium hydrogen phosphate, D-glucose, adenine and water is also referred to as "citrate-phosphate-dextrose solution with adenine (CPDA)".

Preferably, the citrate solution has a concentration of 2-40%, preferably 4% and has a pH in the range of 6.4-7.5. The use of a flow rate of 80 ml/min is preferred. The advantages of using a citrate solution over a PBS solution are the reduced neutralization time and the reduced rinsing volume required.

Device

A further aspect of the present invention relates to an apheresis device (1) for extracorporeal removal of CRP from blood of a patient, wherein the apheresis device (1) is configured to be resistant to an alkali hydroxide solution, such as e.g. a sodium hydroxide solution. Of course, only those parts of the apheresis device which come into contact with the alkali hydroxide solution, i.e. those parts in which the alkali hydroxide solution is stored or through which the alkali hydroxide solution flows, must be resistant to the alkali hydroxide solution used. For example, the cell separator and bypass line do not come into contact with the alkali hydroxide solution and therefore do not necessarily have to be resistant to the alkali hydroxide solution used.

The term "resistant", as used herein, means that no change in product properties occurs, e.g. with respect to biocompatibility, as well as performance.

Chemical resistance generally refers to the resistance of a material to the exposure of chemicals. A material is chemically resistant if the characteristic mechanical, physical and chemical properties of a material remain unchanged or are attacked only very slowly even over longer periods of contact with the chemical substance to be tested. A material is partially chemically resistant if the characteristic properties of the material remain unchanged for a limited period of time acceptable for the intended use or within specific limits of the conditions of use. Chemically unstable, on the other hand, are materials that lose their characteristic properties within a very short time or faster than the intended use permits. Resistant, as used herein, therefore preferably also means that the characteristic properties of the materials of the parts of the apheresis device that come into contact with the alkali hydroxide solution, preferably with sodium hydroxide solution, remain unchanged for a contact time of at least 20 h. As a rule, an acceptable time period for the intended use is between 4 h and 8 h.

Therefore, the parts that come into contact with the alkali hydroxide solution, preferably the sodium hydroxide solution, must be made of a material resistant to alkali hydroxide, preferably sodium hydroxide. Suitable materials include, but are not limited to: stainless steel, polypropylene (PP), polyvinyl chloride (PVC), polyethylene (PE), polyethylene terephthalate (PET), and polycarbonate (PC). Stainless steel, polypropylene (PP), polyvinyl chloride (PVC), polyethylene (PE), and polyethylene terephthalate (PET) are preferred. Herein, materials considered to be resistant to alkali hydroxide, preferably sodium hydroxide, include, but are not limited to stainless steel, polypropylene (PP), polyvinyl chloride (PVC), polyethylene (PE), polyethylene terephthalate (PET), and polycarbonate (PC). Preferred materials that are resistant to alkali hydroxide, preferably sodium hydroxide, are selected from stainless steel, polypropylene (PP), polyvinyl chloride (PVC), polyethylene (PE), polyethylene terephthalate (PET).

In other words, a further aspect of the present invention is directed to an apheresis device (1) for extracorporeal removal of CRP from blood of a patient, wherein the apheresis device is connectable to the blood circulation of the patient, and wherein the apheresis device (1) is configured to be resistant to an alkali hydroxide solution, preferably a sodium hydroxide solution. That is, the mechanical, physical and chemical properties of the parts of the apheresis device that come into contact with the alkali hydroxide solution do not alter within the operating time of the apheresis device for an apheresis treatment.

For regeneration of an apheresis column, an alkali hydroxide solution, preferably a sodium hydroxide solution, can be used. Alkali hydroxide solutions, preferably a sodium hydroxide solution, are known for their reactivity, which, however, depends to a considerable extent on the concentration of the alkali hydroxide in the alkali hydroxide solution, preferably the sodium hydroxide in the sodium hydroxide solution. In addition, other compounds in the alkali hydroxide solution, preferably the sodium hydroxide solution, affect the reactivity of the alkali hydroxide, preferably the sodium hydroxide (or sodium hydroxide in dissociated form).

Therefore, an alkali hydroxide solution, preferably a sodium hydroxide solution, can attack materials. For example, strong bases such as alkali hydroxide solution, preferably sodium hydroxide, react with glass, which can cause glass components to dissolve. Similarly, materials made of organic polymers exist that are not resistant in the presence of alkali hydroxide solution, preferably sodium hydroxide, at room temperature or higher temperatures.

An embodiment according to the invention relates to an apheresis device (1) for extracorporeal removal of CRP from blood of a patient, wherein the apheresis device is connectable to the blood circulation of the patient. The blood is pumped via a part of the extracorporeal circulation system (2) of the apheresis device (1) according to the invention to a cell separator (7) for separation of the blood into blood plasma and cellular components. Via a first outlet of the cell separator (7), the separated blood plasma is directed via a plasma line (8A) to an apheresis column (4) for the affinity chromatographic removal of CRP from the blood plasma. After removal of CRP from the patient's blood plasma, this now treated blood plasma is combined with the cellular components of the blood via a plasma line (8B). Furthermore, the apheresis device (1) according to the invention comprises a bypass line (12) leading from the plasma line (8A) into the plasma line (8B) bypassing the apheresis column (4). Furthermore, the apheresis device (1) according to the invention comprises at least one regeneration line (14), which runs into the plasma line (8A) in the direction of flow after of the bypass line (12) or directly into the apheresis column (4). The apheresis device (1) is configured to be resistant to an alkali hydroxide solution, preferably a sodium hydroxide solution.

That is, the parts of the apheresis device that come into contact with the alkali hydroxide solution are resistant to the alkali hydroxide solution used.

An embodiment of the present invention relates to an apheresis device (1) for extracorporeal removal of CRP from blood comprising:

- an extracorporeal circulation system (2) for blood,
- means (3) for generation and regulation of a flow of the blood in the extracorporeal circulation system (2),
- a cell separator (7) for separation of the blood into blood plasma and cellular components,
- at least one apheresis column (4) for affinity chromatographic removal of CRP from the blood,
- wherein the extracorporeal circulation system (2) comprises an arterial line (5) to the cell separator (7), a plasma line (8A) from the cell separator (7) to the apheresis column (4), a plasma line (8B) for CRP-depleted blood plasma from the apheresis column (4) to a point (P1), a cell line (9) for the separated cellular components from the cell separator (7) to the point (P1), and a venous line (6) starting from the point (P1),
- at least one connection line (11) for connection of at least one fluid container (F) to the arterial line (5) or the cell separator (7),
- characterized in that
- a bypass line (12) branches off from the plasma line (8A) and runs into the plasma line (8B) a waste line (13) goes off directly from the apheresis column (4) or from the plasma line (8B) in the direction of flow before the junction of the bypass line (12), and
- at least one regeneration line (14), which leads to the plasma line (8A) in the direction of flow at or after the junction of the bypass line (12) or runs directly into the apheresis column (4), wherein the apheresis device (1) is configured to be resistant to an alkali hydroxide solution, preferably a sodium hydroxide solution.

Preferably, the apheresis device (1) further comprises a central processing unit (10) for controlling the apheresis device (1).

An embodiment of the present invention relates to an apheresis device (1) for extracorporeal removal of CRP from blood comprising:

- an extracorporeal circulation system (2) for blood,
- means (3) for generation and regulation of a flow of the blood in the extracorporeal circulation system (2),
- a cell separator (7) for separation of the blood into blood plasma and cellular components, at least one apheresis column (4) for affinity chromatographic removal of CRP from the blood, wherein the extracorporeal circulation system (2) comprises an arterial line (5) to the cell separator (7), a plasma line (8A) from the cell separator (7) to the apheresis column (4), a plasma line (8B) for CRP-depleted blood plasma from the apheresis column (4) to a point (P1), a cell line (9) for the separated cellular components from the cell separator (7) to the point (P1), and a venous line (6) starting from the point (P1), at least one connection line (11) for connection of at least one liquid container (F1) to the arterial line (5) or the cell separator (7), characterized in that a bypass line (12) branches off from the plasma line (8A) and runs into the plasma line (8B) a waste line (13) goes off directly from the apheresis column (4) or goes off from the plasma line (8B) in the direction of flow before the junction of the bypass line (12), at least one regeneration line (14) branches off from the at least one liquid container (F1) or the at least one connection line (11) and leads in the direction of flow at or after the junction of the bypass line (12) to the plasma line (8A) or runs directly into the apheresis column (4), and at least one second regeneration line (14) branches off from at least one liquid container (F2) and wherein the second regeneration line (14) has no connection to the arterial line (5) or the cell separator (7) and leads in the direction of flow at or after the junction of the bypass line (12) to the plasma line (8A) or runs directly into the apheresis column (4), wherein the apheresis device (1) is configured to be resistant to an alkali hydroxide solution, preferably a sodium hydroxide solution.

Preferably, the apheresis device (1) further comprises a central processing unit for controlling the apheresis device (1).

Preferably, the apheresis device (1) therefore comprises at least two regeneration lines (14', 14"), which independently of each other lead in the direction of flow at or after the junction of the bypass line (12) to the plasma line (8A) or run directly into the apheresis column (4'), wherein at least one of the regeneration lines (14', 14") goes off from the at least one liquid container (F1) or the at least one connection line (11).

An embodiment of the present invention relates to an apheresis device (1) for extracorporeal removal of CRP from blood comprising:

an extracorporeal circulation system (2) for blood, means (3) for generation and regulation of a flow of the blood in the extracorporeal circulation system (2), a cell separator (7) for separation of the blood into blood plasma and cellular components, at least one apheresis column (4) for affinity chromatographic removal of CRP from the blood, wherein the extracorporeal circulation system (2) comprises an arterial line (5) to the cell separator (7), a plasma line (8A) from the cell separator (7) to the apheresis column (4), a plasma line (8B) for CRP-depleted blood plasma from the apheresis column (4) to a point (P1), a cell line (9) for the separated cellular components from the cell separator (7) to the point (P1), and a venous line (6) starting from the point (P1), at least one connection line (11) for connection of at least one liquid container (F1) to the arterial line (5) or the cell separator (7), characterized in that a bypass line (12) branches off from the plasma line (8A) and runs into the plasma line (8B), a waste line (13) goes off directly from the apheresis column (4) or from the plasma line (8B) in the direction of flow before the junction of the bypass line (12), and at least one regeneration line (14) goes off from the at least one liquid container (F1) or the at least one connection line (11) and leads to the plasma line (8A) in the direction of flow at or after the junction of the bypass line (12) or runs directly into the apheresis column (4), wherein the at least one regeneration line (14) has at least one additional connection for a liquid container (F2), wherein the apheresis device (1) is configured to be resistant to an alkali hydroxide solution, preferably to a sodium hydroxide solution.

Preferably, the apheresis device (1) further comprises a central processing unit for controlling the apheresis device (1), As already mentioned above, the use of the term "resistant" means that only those parts of the apheresis device which come into contact with the alkali hydroxide solution must be resistant or are resistant to the alkali hydroxide solution used. The remaining parts of the apheresis device can, but need not, be resistant to the alkali hydroxide solution used.

Resistant means that the biocompatibility according to the series of standards DIN EN ISO 10993-1 to -12 is not changed. The DIN EN ISO 10993-1 to -12 series of standards includes ISO 10993-1 Assessment and testing as part of a risk management procedure, ISO 10993-2 Animal welfare requirements, ISO 10993-3 Tests for genotoxicity, carcinogenicity and reproductive toxicity, ISO 10993-4 Selection of tests for interaction with blood, ISO 10993-5 Tests for in vitro cytotoxicity, ISO 10993-6 Tests for local effects after implantation, ISO 10993-7 Ethylene oxide sterilization residues, ISO 10993-8 Selection and suitability of reference materials for biological testing, ISO 10993-9 Framework for identification and quantification of potential degradation products, ISO 10993-10 Tests for irritation and skin sensitization, ISO 10993-11 Tests for systemic toxicity, ISO 10993-12 Sample preparation and reference materials. This can be done by testing extracts. For qualitative analysis of the extracts obtained, the standard suggests gas chromatography (GC) or (high-performance) liquid chromatography (LC or HPLC) in combination with mass spectrometry (MS). For further analysis, identification of typically extracted compounds by ion pair chromatography (IPC) or identification of extractable metal ions by inductively coupled plasma (ICP) is recommended. Cytotoxicity tests, tests for hemocompatibility and extractable components are a selection from the many possible test methods according to DIN EN ISO 10993. The cell compatibility test checks whether a product has a toxic/harmful effect on cells. The test is carried out in direct and/or indirect contact and allows toxic materials to be reliably identified. Blood compatibility testing in vitro identifies undesirable material properties at an early stage, before the product can harm the patient. Testing is performed with human blood in simple static or complex dynamic systems. Biomaterials and medical devices trigger non-specific foreign body reactions in the body. Local tissue reaction testing determines parameters for evaluating the suitability and value of a substitute material.

Therefore, it is preferred that the apheresis devices according to the invention, as described herein, are configured to be resistant to an alkali hydroxide solution, preferably a sodium hydroxide solution, wherein resistance to an alkali hydroxide solution, preferably a sodium hydroxide solution, is present if the biocompatibility according to the DIN EN ISO 10993-1 to -12 series of standards is not changed.

Therefore, it is preferred that the apheresis devices according to the invention, as described herein, are configured to be resistant to an alkali hydroxide solution, preferably a sodium hydroxide solution, wherein resistance to an alkali hydroxide solution, preferably a sodium hydroxide solution is present if the parts coming into contact with the alkali hydroxide solution, preferably the sodium hydroxide solution, are made of a material resistant to alkali hydroxide, preferably a sodium hydroxide, wherein the alkali hydroxide resistant materials, preferably sodium hydroxide resistant materials, are selected from a group comprising or consisting of stainless steel, polypropylene (PP), polyvinyl chloride (PVC), polyethylene (PE), polyethylene terephthalate (PET) and/or polycarbonate (PC), preferably stainless steel, polypropylene (PP), polyvinyl chloride (PVC), polyethylene (PE), and/or polyethylene terephthalate (PET).

Preferably, the plasma line is made of stainless steel or a polymer selected from the group comprising or consisting of polypropylene (PP), polyvinyl chloride (PVC), polyethylene (PE), polyethylene terephthalate (PET), and polycarbonates (PC). Particularly preferably, the plasma line is made of stainless steel or a polymer selected from the group comprising or consisting of polypropylene (PP), polyvinyl chloride (PVC), polyethylene (PE), and polyethylene terephthalate (PET).

Preferably, the liquid container for holding the regeneration solution is made of stainless steel or a polymer selected from the group comprising or consisting of polypropylene (PP), polyvinyl chloride (PVC), polyethylene (PE), polyethylene terephthalate (PET), and polycarbonates (PC). Particularly preferably, the liquid container for holding the regeneration solution is made of stainless steel or a polymer selected from the group comprising or consisting of polypropylene (PP), polyvinyl chloride (PVC), polyethylene (PE), and polyethylene terephthalate (PET).

Further preferably, the housing of the apheresis column is made of stainless steel or a polymer selected from the group comprising or consisting of polypropylene (PP), polyvinyl chloride (PVC), polyethylene (PE), polyethylene terephthalate (PET) and polycarbonates (PC). Particularly preferably, the housing of the apheresis column is made of stainless steel or a polymer selected from the group comprising or consisting of stainless steel, polypropylene (PP), polyvinyl chloride (PVC), polyethylene (PE), and polyethylene terephthalate (PET).

As mentioned above, the apheresis device (1) according to the present invention for extracorporeal removal of CRP from blood is connectable to the blood circulation of a patient. From a vascular access point on the patient (usually a venous access point), blood is pumped to a cell separator (7) via a part of the extracorporeal circulation system (2) of the present invention. The part of the extracorporeal circulation system (2) that directs the blood out of the patient and to the cell separator (7) directs the blood away from the patient and thus away from the patient's heart, and is therefore referred to as the "arterial line" (5) in reference to the vascular nomenclature in the human body.

The patient's blood is fed through an inlet of the cell separator (7) into the cell separator (7), where it is separated by the latter into blood plasma (sometimes also referred to simply as "plasma") and the cellular components of the blood. Here, it must be taken into account that the separation into blood plasma and cellular components is not complete, but only preferably 10 to 90% of the total blood plasma is separated from the cellular components. Via a first outlet of the cell separator (7), the separated blood plasma is conducted via a plasma line (8A) to the apheresis column (4) for the affinity chromatographic removal of CRP from the blood (or from the blood plasma). After removal or reduction of CRP in the patient's blood plasma, this now treated blood plasma (also referred to as "depleted blood plasma") is directed to the point (P1) via a plasma line (8B). Via a second outlet of the cell separator (7) and a connection line (the so-called cell line (9)), the cellular components of the blood are passed by the apheresis column (4) and led to the point (P1). There, the cellular components are combined with the depleted blood plasma. After the cellular components are combined with the depleted blood plasma, the now treated blood is returned to the patient via another part of the extracorporeal circulation system (2) of the present invention. The part of the extracorporeal circulation system (2) that conducts the treated blood from the point (P1) of the extracorporeal circulation system (2) back to the patient conducts the blood to the patient and thus also to the patient's heart and is therefore referred to as the "venous line" (6) in reference to the vascular nomenclature in the human body.

In an alternative embodiment of the present invention, it is possible for the cellular components to also be returned to the patient directly after separation from the plasma via the second outlet on the cell separator and a subsequent line, and only the treated plasma is delivered to the patient via the venous line.

In order to be able to prevent coagulation of the blood in the extracorporeal circulation system or to enable rinsing or pre-rinsing of the extracorporeal circulation system (e.g. with a physiological saline solution), the apheresis device according to the invention comprises at least one line (the so-called connection line (11)), which enables the connection of at least one liquid container (F) and thus the feeding of the liquid (e.g. an anticoagulant or a physiological saline solution) contained in this at least one liquid container (F) into the extracorporeal circulation system. In this context, it is also referred to that the connection line (11) for connection of at least one fluid container (F) is in fluidic connection with the extracorporeal circulation system, i.e. a fluid from a fluid container can be introduced into the extracorporeal circulation system via the connection line (11). In preferred embodiments of the present invention, the at least one connection line (11) runs into the extracorporeal circulation system (2), i.e. into the arterial line (5), before the cell separator (7), or directly into the cell separator (7).

It is obvious to the skilled person that the liquid container(s) (F) itself need not be part of the apheresis device according to the invention, since these are generally disposable articles, e.g. in the form of common infusion bags, which are connected to the connection line by the operating personnel (e.g. the attending physician or a nurse) in accordance with the specific application.

According to the invention, the presence of a single connection line (11) for connection of a liquid container is possible. However, it is also conceivable that a single connection line (11) is present to which two or three or preferably more liquid containers can be connected. Likewise, embodiments of the apheresis device according to the invention with two, preferably three or preferably several connection lines (11', 11", 11'", etc.) each for the connection of at least one liquid container are possible, wherein it is preferred that these two, preferably three or preferably several connection lines can run independently of each other into the arterial line (5) or directly into the cell separator (7). "Independent of each other" means in this context, for example, that in an embodiment of the apheresis device according to the invention with two connection lines (11', 11"), one connection line (11') can run into the arterial line (5) and the other connection line (11") can run directly into the cell separator (7), but also that both connection lines (11', 11") can run into the arterial line (5) or that both connection lines (11', 11") can run directly into the cell separator (7).

According to an embodiment of the present invention, it is particularly preferred if the apheresis device (1) according to the invention has two connection lines (11', 11") each for connection of at least one liquid container, wherein the connection lines (11', 11") run independently of each other into the arterial line (5) or directly into the cell separator (7). Consequently, both connection lines (11', 11") run into the arterial line (5) or both connection lines (11', 11") run directly into the cell separator (7) or, particularly preferably, one connection line (11') runs into the arterial line (5) and the other connection line (11") runs directly into the cell separator (7). Thereby it is possible that the two connection lines (11', 11") can be connected to different liquid containers. It is particularly preferred if one of the two connection lines (e.g. 11') is connected to a liquid container containing a physiological salt solution (e.g. NaCl solution), while the second of the two connection lines (e.g. 11") is connected to a liquid container containing e.g. a citrate solution.

Thus, it is particularly preferred if the apheresis device (1) has a connection line (11') for connection of a liquid container (F1) and a connection line (11") for connection a liquid container (F2) and the connection line (11') runs into the arterial line (5) or into the cell separator (7) and the connection line (11") runs into the arterial line (5) or into the cell separator (7) or into the connection line (11') and thus ultimately also into the arterial line (5) or into the cell separator (7).

A significant advantage of the apheresis device according to the invention is that the apheresis column, which is naturally limited in its purification capacity, can be regenerated during operation, i.e. without having to stop the blood collection and supply or the cell separator. For this purpose, there is a bypass line (12, also referred to as a "shunt") which allows the plasma flow to be diverted while bypassing the apheresis column (4). This bypass line (12) enables temporary decoupling of the apheresis column (4) from the plasma flow and thus regeneration of the apheresis column (4) without having to interrupt the flow of blood or blood plasma in the device according to the invention. The bypass line branches off from the plasma line (8A), wherein the point in the plasma line (8A) from which the bypass line branches off is referred to as point (P2), and preferably runs into the plasma line (8B), wherein the point in the plasma line (8B) into which the bypass line (12) runs is referred to as point (P6). In an equally possible embodiment, the bypass line (12) does not run into the plasma line (8B), but into the cell line (9), wherein the point in the cell line (9) into which the bypass line (12) runs is referred to as point (P3).

The regeneration solution required for the regeneration of the apheresis column is fed into the extracorporeal circulation system (2) via the regeneration line (14), wherein the regeneration line (14) either runs directly into the apheresis column (4) or runs (in the direction of flow) into the plasma line (8A) before the apheresis column (4) but (in the direction of flow) at or after the branch of the bypass line, i.e. after the point (P2).

In order to remove the regeneration solution from the system after passing through the apheresis column (4) (and not being delivered to the patient), the waste line (13) is present, which branches off from the plasma line (8B), wherein the point in the plasma line (8B) from which the waste line (13) branches off is referred to as point (P4). In embodiments in which the bypass line (12) runs into the cell line (9), the point (P4) is preferably located in a region from the apheresis column (4) to the point (P1). In embodiments in which the bypass line (12) runs into the plasma line (8B), the point (P4) is preferably located in a region from the apheresis column (4) to the point (P6). Of course, a collection container, for example, can be connected to the waste line (13). Alkali hydroxide solution, preferably sodium hydroxide solution, is particularly preferred as regeneration solution according to the invention.

In addition to the regeneration solution, a rinsing solution can also be used. The rinsing solution can, but does not have to, serve to regenerate the apheresis column (4), but has the primary task of displacing the blood plasma from the plasma line (8A) in the region from point P2 to the apheresis column (4), from the apheresis column (4), and from the plasma line (8B) from the apheresis column (4) to point P4 before the regeneration solution is used, which is discarded via the waste line (13) after passing through the apheresis column (4). Preferably, a physiological NaCl solution or PBS solution is used as the rinsing solution. Even more preferably, a physiological NaCl solution is used as the rinsing solution if an alkali hydroxide solution, preferably a sodium hydroxide solution, is used as the regeneration solution.

Preferably, the apheresis device (1) comprises at least one regeneration line (14) which leads in the direction of flow at or after the branch of the bypass line (12) to the plasma line (8A) or directly into the apheresis column (4). Preferably, the apheresis device (1) comprises at least one regeneration line (14) that runs into the extracorporeal circulation system (2) in a region from the branch of the bypass line (12) at the plasma line (8A) up to the apheresis column (4). Preferably, the apheresis device (1) comprises at least one regeneration line (14) that runs into the extracorporeal circulation system (2) in a region from point (P2) to the apheresis column (4).

According to an embodiment of the present invention, it is preferred that the apheresis device (1) according to the invention has at least two connection lines (11) each for connection of at least one liquid container to the arterial line (5) or the cell separator (7).

Furthermore, embodiments of the apheresis device (1) are preferred, wherein the apheresis device (1) has at least two connection lines (11) each for connection of at least one liquid container (F) to the arterial line (5) or the cell separator (7), and wherein there is a regeneration line (14) for each liquid container (F), which goes off from the respective liquid container (F) or its connection line (11) and which each lead into the plasma line (8A) or directly into the apheresis column (4).

It is also possible that the at least two connection lines (11) merge before their junction, i.e. converge into one line. It is also possible that the regeneration lines (14) merge before their junction, i.e. converge into one line.

If it is described in the present application that a device feature lies in a region from a first position in the device to a second position in the device or runs into this region or branches off from this region, this is to be understood in such a way that both the first position and the second position and the section lying in between are enclosed by this region. This is to be illustrated by the following example: The statement that the "regeneration line (14) runs into the extracorporeal circulation system (2) in a region from point (P2) to the apheresis column (4)" means that the regeneration line (14) runs into a region of the extracorporeal circulation system (2) that includes not only the section between point (P2) and the apheresis column (4), but also includes point (P2) itself as well as the apheresis column (4). That means that the regeneration line (14) may run into point (P2), or into the apheresis column (4), or even into the section of the plasma line (8A) that lies between point (P2) and the apheresis column (4).

Point (P1) is the nodal point in the extracorporeal circulation system (2) at which the plasma line (8B) merges with the venous line (6). Point (P2) is the nodal point in the extracorporeal circulation system (2) where the bypass line (12) branches off from the plasma line (8A). The point (P3) is the nodal point in the extracorporeal circulation system (2) where the bypass line (12) runs into the cell line (9). The point (P4) is the nodal point in the extracorporeal circulation system (2) where the waste line (13) branches off from the plasma line (8B). The point (P5) is the nodal point in the extracorporeal circulation system (2) where the regeneration line (15) runs into the connection line (11). The point (P6) is the nodal point in the extracorporeal circulation system (2) at which the bypass line (12) runs into the plasma line (8B).

According to a preferred embodiment of the present invention, the connection line (11) runs into the arterial line (5). According to a further preferred embodiment of the present invention, the connection line (11) runs directly into the cell separator (7).

As already described, the apheresis device according to the invention comprises at least one line (the so-called regeneration line (14)), which enables the feeding of a regeneration solution (e.g. an alkali hydroxide solution, preferably a sodium hydroxide solution) or a rinsing solution or a neutralization solution into the extracorporeal circulation system preferably shortly before the apheresis column (4) or directly into the apheresis column (4). In this context, it is also referred to that the regeneration line (14) for connection of at least one liquid container (F) is in fluidic connection with the extracorporeal circulation system, i.e. a liquid from a liquid container can be introduced into the extracorporeal circulation system via the regeneration line.

According to a preferred embodiment of the present invention, the regeneration line (14) runs into the plasma line (8A) after point (P2), i.e. between point (P2) and the apheresis column (4). According to a further preferred embodiment of the present invention, the regeneration line (14) runs into the plasma line (8A) at point (P2). According to a further preferred embodiment of the present invention, the regeneration line (14) runs directly into the apheresis column (4).

It is obvious to the skilled person that a liquid container (F) for connection to the regeneration line itself does not have to be part of the apheresis device according to the invention, since these are generally single use articles, e.g. in the form of common infusion bags, which are connected to the connection line by the operating personnel (e.g. the attending physician or a nurse) in accordance with the specific application.

According to the invention, the presence of a separate regeneration line (14) for connection of a liquid container (F) is possible. Here, for example, it is conceivable that a separate liquid container, e.g. an infusion bag with alkali hydroxide solution, preferably sodium hydroxide solution, can be connected to the regeneration line (14). However, it is also conceivable that the end of the regeneration line (14) which enables the connection of a liquid container is located in spatial proximity to the end of a connection line (11) which enables the connection of a liquid container, so that a liquid container (with at least two connection options or a corresponding adapter) can be connected to both the connection line (11) and the regeneration line (14), e.g. for infusion bags with NaCl solution or citrate solution.

According to the invention, the presence of a single regeneration line (14) is possible and particularly preferred are 1 or 2 regeneration lines. Also, embodiments of the apheresis device according to the invention with two, three or more regeneration lines (14', 14", 14'", etc.) are possible, in which case these two, three or more regeneration lines can run into the extracorporeal circulation system (2) independently of each another in a region from the branch of the bypass line (12) at the plasma line (8A) (i.e. from point P2) to the apheresis column (4). "Independent of each other" in this context means, for example, that in an embodiment of the apheresis device according to the invention with two regeneration lines (14', 14"), one regeneration line (14') runs into the plasma line (8A) between point (P2) and the apheresis column (4) and the other regeneration line (14") runs directly into the apheresis column (4), but also that both regeneration lines (14', 14") can run into the plasma line (8A) between point (P2) and the apheresis column (4). It is also possible that one regeneration line (14') runs into the other regeneration line (14"). However, when two or more regeneration lines (14', 14", 14'", etc.) are present, it is particularly preferred that all regeneration lines (14', 14", 14'", etc.) run into the extracorporeal circulation system (2) at the same point in the region from point (P2) to the apheresis column (4), even more preferred that all regeneration lines (14', 14", 14'", etc.) run into the extracorporeal circulation system (2) at point (P2).

According to the invention, it is particularly advantageous if a connection line (11) and a regeneration line (14) use the same liquid source, since this not only saves space, but also minimizes the effort required for operation and maintenance of the apheresis device according to the invention. In this way, existing apheresis systems can also be modified or supplemented without the need to connect a separate additional large-scale device. Therefore, in preferred embodiments of the present invention, the regeneration line (14) branches off from the connection line (11), wherein the point in the connection line (11) from which the regeneration line (14) branches off is referred to as point (P5).

According to some embodiments of the present invention, it is therefore preferred that the at least one regeneration line (14) leading into the plasma line (8A) or directly into the apheresis column (4) starts from a point (P5) in the at least one connection line (11).

In embodiments, wherein more than one connection line (11', 11", 11'" etc.) is present and a regeneration line (14) is connected to several connection lines (11', 11", 11'" etc.), the nomenclature of the branching points (P5', P5", P5'" etc.) is based on the nomenclature of the connection line (11', 11", 11'" etc.). That is, by way of example, a regeneration line (14) that runs into or connects to two existing connection lines (11', 11"), the point at which the regeneration line (14) runs into the connection line (11') is referred to as point (P5') and the point at which the regeneration line (14) runs into the connection line (11") is referred to as point (P5").

An apheresis device (1) is preferred, wherein the apheresis device (1) has two connection lines (11', 11") each for connection of one liquid container (F1, F2) to the arterial line (5) or the cell separator (7), and wherein two regeneration lines (14', 14") go off from the two liquid containers (F1, F2) or the two connection lines (11', 11") and lead into the plasma line (8A) or directly into the apheresis column (4).

Embodiments are also particularly preferred, wherein a regeneration line (14), which leads into the plasma line (8A) or directly into the apheresis column (4) and which starts from a point (P5) in the at least one connection line (11), has at least one additional connection for a liquid container (see FIG. 5). An infusion bag containing alkali hydroxide solution, preferably sodium hydroxide solution, can preferably be connected to this additional connection.

In preferred embodiments, the apheresis device (I) further comprises at least one regeneration line (14), which goes off from the at least one liquid container (F1) or the at least one connection line (11) and leads in the direction of flow at or after the branch of the bypass line (12) to the plasma line (8A) or runs directly into the apheresis column (4), wherein the at least one regeneration line (14) has at least one additional connection for a liquid container (F2). An infusion bag containing alkali hydroxide solution, preferably sodium hydroxide solution, can preferably be connected to this additional connection.

In preferred embodiments, the apheresis device (1) further comprises at least one second regeneration line (14), which goes off from at least one liquid container (F2) and wherein the second regeneration line (14) has no connection to the arterial line (5) or the cell separator (7) and leads in the direction of flow at or after the branch of the bypass line (12) to the plasma line (8A) or runs directly into the apheresis column (4). An infusion bag with alkali hydroxide solution, preferably a sodium hydroxide solution, can preferably be connected to this second regeneration line (14).

In embodiments with more connection lines than regeneration lines, wherein each regeneration line establishes a connection to at least one connection line, it is possible that each regeneration line is connected to one connection line and the excess connection line(s) are connected only to the arterial line or the cell separator, or that the more numerous connection lines converge on the regeneration lines, i.e. several connection lines are connected to one regeneration line. Mixed forms are also possible.

There are various possibilities to regulate the flow rates in the part of the connection line (11) after point (P5) and in the regeneration line (14). This could be done, for example, by separately controllable pumps in the part of the connection line (11) after the point (P5) and in the regeneration line (14). Another possibility would be a pump located in the connection line (11) before point (P5), wherein the distribution of flow rates after point (P5) is either fixed by the diameters of regeneration line (14) and connection line (11) or can be regulated by appropriate means (clamps, valves) (e.g. by varying the respective line diameter). The regulation of flow rates is of course particularly important when a solution (e.g. a citrate solution) has to be fed into the system via the connection line (11) (e.g. for anticoagulation of the blood) and at the same time has to enter the apheresis column via the regeneration line (14) (e.g. as neutralization solution). For example, by means of such mechanisms the feed of solution via the connection line (11) can be kept constant (e.g. for constant anticoagulation), even if solution is branched off in phases for neutralization of the apheresis column after regeneration with alkali hydroxide solution, preferably sodium hydroxide solution via the regeneration line (14).

In comparison to other systems, a maximum number of 8, preferably 7, further preferably 6, and most preferably 5 pumps are sufficient for the apheresis device (1).

In embodiments of the present invention with several connection lines (11', 11", 11"', etc.) and several regeneration lines (14', 14", 14"', etc.), it is possible that each connection line is in connection with one of the regeneration lines, which in turn runs into the plasma line (8A) or directly into apheresis column (4) after point (P2). Here, each regeneration line can run independently of other regeneration lines into the plasma line (8A) or directly into apheresis column (4) at a point after point (P2). However, it is preferred that all regeneration lines run into the plasma line (8A) or directly into apheresis column (4) at the same point after point (P2), even more preferably directly into apheresis column (4) and most preferably at point (P2). One such exemplary embodiment may be explained with reference to FIG. 4: Here, the apheresis device (1) has a first connection line (11'), which firstly leads into the arterial line (5) and from which, secondly, a first regeneration line (14') branches off at point (P5'). The apheresis device (1) also has a second connection line (11"), which firstly leads directly into the cell separator (7) and from which, secondly, a second regeneration line (14") branches off at point (P5"). In this embodiment, both regeneration lines (14', 14") run into the extracorporeal circulation system (2) at point (P2).

An apheresis device (1) is therefore preferred, wherein the apheresis device (1) has two connection lines (11', 11") each for connection of at least one liquid container (F) to the arterial line (5) or the cell separator (7), and wherein the at least one regeneration line (14) leading into the plasma line (8A) or directly into the apheresis column (4) connects at a point (P5') to the connection line (11') and at a point (P5") to the connection line (11").

Thus, embodiments of the apheresis device (1) are particularly preferred, wherein the apheresis device (1) has two connection lines (11', 11") each for connection of at least one liquid container (F1, F2) to the arterial line (5) or the cell separator (7), and wherein at least one regeneration line (14) leading into the plasma line (8A) or directly into the apheresis column (4), connects at a point (P5') to the connection line (11') and at a point (P5") to the connection line (11"), and wherein a regeneration line (14') leads from the liquid container (F1) or from the connection line (11') that goes off from the liquid container (F1) to the apheresis column (4) or to the plasma line (8A) and a regeneration line (14") leads from the liquid container (F2) or from the connection line (11") that goes off from the liquid container (F2) to the apheresis column (4) or to the plasma line (8A) or into the regeneration line (14').

Thus, it is particularly preferred if the apheresis device (1) has a connection line (11') for connection of a liquid container (F1) and a connection line (11") for connection of a liquid container (F2), and the connection line (11') runs into the arterial line (5) or into the cell separator (7), and the connection line (11") runs into the arterial line (5) or into the cell separator (7) or into the connection line (11') and therefore ultimately also into the arterial line (5) or into the cell separator (7), and a regeneration line (14') leads from the liquid container (F1) or from the connection line (11') to the apheresis column (4) or to the plasma line (8A), and a regeneration line (14") leads from the liquid container (F2) or from the connection line (11") to the apheresis column (4) or to the plasma line (8A) or into the regeneration line (14').

Embodiments of the apheresis device (1) are therefore particularly preferred, wherein the apheresis device (1) has a connection line (11') for connection of a liquid container (F1) to the arterial line (5) or the cell separator (7) and a connection line (11") for connection of a liquid container (F2) to the arterial line (5) or the cell separator (7), and wherein a regeneration line (14') goes off from the liquid container (F1) or the connection line (11') and runs in the direction of flow after the branch of the bypass line (12) into the plasma line (8A) or directly into the apheresis column (4), and a regeneration line (14") goes off from the liquid container (F2) or the connection line (11") and leads in the direction of flow after the branch of the bypass line (12) into the plasma line (8A) or into the regeneration line (14') or directly into the apheresis column (4).

According to an embodiment, an apheresis device (1) is preferred, wherein the apheresis device (1) has two connection lines (11', 11") each for connection of at least one liquid container to the arterial line (5) or the cell separator (7), and wherein at least one regeneration line (14) leading into the plasma line (8A) or directly into the apheresis column (4) establishes a connection at point (P5') to the connection line (11') and at point (P5") to the connection line (11"). This is to be understood in such a way that a regeneration line (14) is the connection element between the connection lines (11', 11") on one side and the plasma line (8A) or the apheresis column (4) on the other side. A liquid from one of the liquid containers (F) connected to one of the two connection lines (11', 11") could therefore flow via the regeneration line (14) to point (P2) into the plasma line (8A) or directly into the apheresis column (4).

Embodiments with two (or even more) connection lines are ideally suitable for using different regeneration solutions for regeneration of the apheresis column (4) and for successive introduction into the apheresis column (4). For example, such a device is ideally suitable for first introducing an NaCl solution to displace the plasma contained in the apheresis column, followed by an alkali hydroxide solution, preferably a sodium hydroxide solution, for efficient and rapid regeneration of the adsorber, and finally again an NaCl solution to displace the alkali hydroxide solution, preferably a sodium hydroxide solution, contained in the apheresis column, before plasma is again introduced into the apheresis column.

In embodiments of the apheresis device according to the invention, in which the bypass line (12) leads to the point (P6) in the plasma line (8B), it is preferred that the point (P6) is located before (in the flow direction) the point (P1) (see FIGS. 1-2).

According to a preferred embodiment of the present invention, the connection line runs into the arterial line. According to a further preferred embodiment of the present invention, the connection line runs directly into the cell separator.

According to a preferred embodiment of the present invention, the regeneration line (14) runs into the plasma line (8A) after point (P2), i.e. between point (P2) and the apheresis column (4). According to a further preferred embodiment of the present invention, the regeneration line (14) runs directly into the apheresis column (4).

To reduce the dead volume of the system, it is particularly preferred according to the invention that the at least one regeneration line (14) runs into the extracorporeal circulation system (2) at point (P2) in the apheresis device (1) according to the invention. In embodiments, wherein more than one regeneration line (14', 14", 14'", etc.) is present, it is particularly preferred that all of the present regeneration lines (14', 14", 14'", etc.) run into the extracorporeal circulation system (2) at point (P2), or run into the plasma line (8A) at point (P2).

Therefore, the present invention is also directed to an apheresis device (1) according to the invention, wherein the bypass line (12) leads from a point (P2) in the plasma line (8A) to a point (P6) in the plasma line (8B), and the waste line (13) leads from a point (P4) from the plasma line (8B), and the at least one regeneration line (14) runs into the plasma line (8A) at the point (P2).

To further reduce the dead volume of the system, it is even more preferred that not only the regeneration line (14) runs into the plasma line (8A) at the point (P2), where also the bypass line (12) branches off from the plasma line (8A), but also that the waste line (13) branches off from the same point in the plasma line (8B) into which also the bypass line (12) runs. In other words, it is preferred that the point (P6) at which the bypass line (12) runs into the plasma line (8B) and the point (P4) at which the waste line (13) branches off from the plasma line (8B) coincide, i.e. if P4=P6 (see also FIG. 2).

Therefore, the present invention is also directed to an apheresis device (1) according to the invention, wherein the bypass line (12) leads from a point (P2) in the plasma line (8A) to a point (P6) in the plasma line (8B), and the waste line (13) leads from a point (P4) in the plasma line (8B), and the at least one regeneration line (14) runs into the plasma line (8A) at the point (P2), and wherein the point (P6) and the point (P4) are identical.

In the device according to the invention, a cell separator is installed which separates the blood of the patient supplied to it (via the arterial line) into blood plasma and cellular components, and forwards these fractions via the corresponding lines, i.e. the plasma line and the cell line, respectively. Here, as already mentioned, it must be taken into account that the separation into blood plasma and cellular components by the cell separators used is not complete, but only preferably 10 to 90% of the total blood plasma is separated from the cellular components. When centrifugal cell separators are used, preferably 70% to 90%, more preferably 80% to 87% of the total blood plasma is separated from the cellular components. With the use of membrane cell separators preferably 10% to 30%, more preferably 13% to 25%, still more preferably 15% to 20% of the total blood plasma is separated from the cellular components.

Possible types of cell separators that may be used in connection with the present invention comprise centrifugal cell separators, membrane cell separators such as, for example, membrane cell separators with semi-permeable membranes, and membrane cell separators with rotating membranes.

Therefore, the present invention is also directed to an apheresis device for extracorporeal removal of CRP from blood, wherein the cell separator (7) is either a centrifugal cell separator or a membrane cell separator.

Where in the present application the position of one or more components of the apheresis device according to the invention in relation to another component of the apheresis device according to the invention is described by the terms “before” or “after” (or “in the direction of flow before” and “in the direction of flow after”), this refers to the general direction of flow of the blood or blood plasma in the apheresis device according to the invention. “Before” in relation to a component of the device according to the invention consequently means against the general direction of flow of the blood or blood plasma, and “after” in relation to a component of the device according to the invention consequently means in the general direction of flow of the blood or blood plasma. It is preferred that the direction of flow in the apheresis device does not reverse or is not reversed by the means for generation and regulation of a flow.

According to the present invention, the apheresis device for extracorporeal removal of CRP from blood according to the invention comprises an apheresis column (4) for affinity chromatographic removal of CRP from blood or blood plasma, the function of which is to bind CRP present in the blood or blood plasma of a patient and which is passed through the apheresis column (4).

Pumps

According to the present invention, means for generation and regulation of a flow of blood (or blood plasma) in the extracorporeal circulation system are provided in the apheresis device for extracorporeal removal of CRP from blood according to the invention. For this, one or more pumps or pump systems are generally used which enable a controllable flow of the blood (or blood plasma or also the regeneration solution or anticoagulation solution) through the extracorporeal circulation system and the components of the device according to the invention which are fluidly connected thereto.

According to the invention, the preferred direction of flow within the extracorporeal circulation system and the components of the device according to the invention that are fluidly connected to it proceeds from the access on the patient through which the blood enters the device according to the invention, via the arterial line of the extracorporeal circulation system to the venous line of the extracorporeal circulation system and to the access on the patient at which the treated blood is returned to the patient.

The means for generation and regulation of a flow according to the invention used in the extracorporeal circulation system are preferably pumps in the form of peristaltic pumps (also referred to as hose pumps), piston pumps, pneumatic pumps, hydraulic pumps or other types of pumps known to the skilled person. Consequently, the term "means for generation and regulation of a flow" and the term "pump" may be used synonymously herein.

According to the invention, it is preferred that the means for generation and regulation of a flow of blood (or blood plasma or also the regeneration solution or anticoagulation solution) used in the extracorporeal circulation system have no direct physical contact with the blood (or blood plasma or also the regeneration solution or anticoagulation solution) in the device according to the invention. This is particularly advantageous for hygienic reasons and prevents contamination of complex mechanical components such as a pump by blood as well as, of course, of the blood by the means for generation of a flow used.

In a particularly preferred embodiment of the present invention, the means for generation and regulation of a flow in the extracorporeal circulation system are therefore one or more peristaltic pump(s).

The exact location of the means for generation and regulation of a flow in the extracorporeal circulation system, i.e. the one or more pump(s), is not essential to the present invention. Embodiments of the present invention using only one pump are possible, in which the pump is located in the arterial line region of the apheresis device according to the invention for extracorporeal removal of CRP from blood, i.e. before the cell separator. According to the invention, if several means for generation and regulation of a flow in the extracorporeal circulation system are provided, i.e. several pumps, it is preferred that these can be controlled and regulated independently of each other (e.g. by the CPU; e.g. by the central processing unit). Depending on the specific application, different flow rates within the extracorporeal circulation system may be desired or required. It is also conceivable that different flow rates are desired in different components of the device according to the invention during a specific application.

According to the invention, several means for generation and regulation of a flow (i.e. pumps) can also be integrated in the apheresis device according to the invention. Thus, it is possible that means for generation and regulation of a flow are located in the arterial line (5) and/or in the plasma line (8A) and/or in the plasma line (8B) and/or in the venous line (6) and/or in the bypass line (12) and/or in the cell line (9) and/or in the connection line (11) and/or in the connection lines (11', 11", 11'", etc.) and/or in the regeneration line (14) and/or the regeneration lines (14', 14", 14'", etc.). As indicated above, according to an embodiment of the present invention in which the regeneration line (14) branches off from the connection line (11) at point (P5), it is preferred that a means for generation and regulation a flow (of inorganic salt solutions) is provided in the connection line (11) before point (P5).

According to a further embodiment of the present invention, in which the regeneration line (14) branches off from the connection line (11) at point (P5), it is preferred that a means for generation and regulation of a flow is provided in the connection line (11) after point (P5) and a means for generation and regulation of a flow is provided in the regeneration line (14).

Furthermore, the apheresis device (1) preferably has at least one particle filter which is provided after the apheresis column (4) in the plasma line (8B) or the venous line (6). Furthermore, the apheresis device (1) preferably has at least one bubble catcher provided after the apheresis column (4) in the plasma line (8B) or the venous line (6).

In the case of a centrifuge as cell separator (7), the apheresis device (1) preferably has at least one plasma reservoir provided after the centrifuge (7) and before the apheresis column (4) in the plasma line (8A).

In further embodiments, the apheresis device according to the invention for extracorporeal removal of CRP from blood or blood plasma may comprise one or more pressure sensors that serve to measure or monitor the pressure in a specific section of the device according to the invention. This not only serves to monitor and adjust the operating parameters of the apheresis device according to the invention, but is also advantageous in the event of a malfunction (e.g., a blockage of a tube or filter of the device), wherein the operation can be stopped to avoid harmful consequences for the patient. The exact mode of operation and installation position in the device according to the invention is part of the prior art and is known to the person skilled in the art. In a preferred embodiment of the present invention, at least one pressure sensor is arranged in the arterial line of the apheresis device according to the invention as wells as at least one pressure sensor is arranged in the venous line of the apheresis device according to the invention. In a further preferred embodiment of the present invention, such pressure sensors are integrated in the means for generation and regulation of a flow in the extracorporeal circulation system used of the apheresis device according to the invention.

Preferred pressures or pressure ranges for NaOH solution are −200 to 200 mbar; differential pressure; before and after adsorber: max. 300 mbar.

In order to be able to control the direction of flow in the system at the nodal points of the extracorporeal circulation system, i.e. at the points where several lines converge or diverge from each other, means are preferably provided which determine the flow of the solution (e.g. blood, plasma or regeneration solution). These may be valves, multi-way valves, clamps, or valves in the form of stop valves, check valves, pressure valves, directional valves, or other types of valves known to those skilled in the art, which allow the flow in a certain direction and block the flow in another direction. Preferably, such means for regulation of a flow (e.g. valves) are located at point (P1) and/or at point (P2) and/or at point (P3) and/or at point (P4) and/or at point (P5) and/or at point (P6). In addition, it is possible that, for example, at one point two or more valves are connected in series to enable a more complex flow regulation.

It is also particularly preferred that the means for regulation of a flow (e.g. valves) can be controlled electronically, i.e. their position can be effected by the central processing unit.

Therefore, the present invention is also directed to an apheresis device for extracorporeal removal of CRP from blood, wherein electronically controlled valves are provided at points (P1), (P2), (P4), (P5), (P6), (P7), and (P8).

It is also conceivable and in accordance with the invention that valves are not located directly at the branching points (P1, P2, P4, P5, P6, P7, and P8), but are located in the upstream and/or downstream lines, and thus control the flow of solutions in the extracorporeal circulation system. Hose clamps can also be used for this purpose. It is particularly preferred that these valves or hose clamps are electronically controlled.

A further advantage of the present invention, which is related to the fact that the apheresis and the regeneration of the apheresis column are implemented in a single device, is that the entire device can be controlled via a single central processing unit (CPU). Thus, the different programs during an apheresis session, for example, normal operation, in which the blood plasma is passed through the apheresis column, and regeneration operation, in which the blood plasma is bypassing the apheresis column through the bypass line and the apheresis column is rinsed with a regeneration solution, can be controlled by a single processing unit or software located on it. This facilitates the automation of many processes and thus reduces the scope for operator error by the personnel. In prior art devices, on the other hand, different complex systems (primary system for blood separation into plasma and cellular components; and secondary system for apheresis and regeneration) must be combined, wherein each system has to be controlled separately.

Therefore, the present invention is also directed to an apheresis device for extracorporeal removal of CRP from blood, wherein the entire device is controlled only by means of the one central processing unit.

A further aspect of the present invention is directed to an apheresis device (II) for extracorporeal removal of CRP from blood of a patient, wherein the apheresis device contains at least two apheresis columns, and wherein the apheresis device (II) is configured to be resistant to an alkali hydroxide solution, preferably a sodium hydroxide solution.

In other words, a further aspect of the present invention is directed to an apheresis device (II) for extracorporeal removal of CRP from blood of a patient, wherein the apheresis device contains at least two apheresis columns, wherein the apheresis device is connectable to the blood circulation of the patient, and wherein apheresis device (II) is configured to be resistant to an alkali hydroxide solution, preferably a sodium hydroxide solution.

A further aspect of the present invention relates to an apheresis device, wherein a second apheresis column (4") is connected to the bypass line or the bypass line comprises a second apheresis column. Preferably, the second apheresis column (4") is included in the bypass line. Thus, the apheresis devices according to the invention for extracorporeal removal of CRP from blood, as described herein, may contain a second apheresis column (4"), wherein the second apheresis column (4") is included in the bypass line. An apheresis column (4") is included in the bypass line when a section of the bypass line (12') of the bypass line (12) runs into the second apheresis column (4") and another section of the bypass line (12") of the bypass line (12) leads away from the outlet of the apheresis column (4").

Therefore, a further aspect of the present invention is an apheresis device (II) for extracorporeal removal of CRP from blood comprising:

an extracorporeal circulation system (2) for blood, a means (3) for generation and regulation of a flow of the blood in the extracorporeal circulation system (2), a cell separator (7) for separation of the blood into blood plasma and cellular components, two apheresis columns (4', 4") for affinity chromatographic removal of CRP from the blood plasma, wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1), and a venous line (6) starting from the point (P1), at least one connection line (11) for connection of at least one fluid container (F) to the arterial line (5) or the cell separator (7), characterized in that a bypass line (12) branches off from the plasma line (8A) and runs into the plasma line (8B), and the bypass line (12) comprises the second apheresis column (4"), a waste line (13) goes off directly from the apheresis column (4') or from the plasma line (8B) in the direction of flow before the junction of the bypass line (12), and at least one regeneration line (14) leads to the plasma line (8A) in the direction of flow after the branch of the bypass line (12) or runs directly into the apheresis column (4'), and wherein a second apheresis column (4") is connected in parallel with the first apheresis column (4') and both apheresis columns (4', 4") can only be operated alternately, i.e. cannot be used simultaneously for removal of CRP, wherein the apheresis device (II) is configured to be resistant to an alkali hydroxide solution, preferably a sodium hydroxide solution.

Preferably, the apheresis device (II) further comprises a central processing unit for controlling the apheresis device (II).

Therefore, a further aspect of the present invention is an apheresis device (II) for extracorporeal removal of CRP from blood comprising:

an extracorporeal circulation system (2) for blood, a means (3) for generation and regulation of a flow of the blood in the extracorporeal circulation system (2), a cell separator (7) for separation of the blood into blood plasma and cellular components, two apheresis columns (4', 4") for affinity chromatographic removal of CRP from the blood plasma, wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1), and a venous line (6) starting from the point (P1), at least one connection line (11) for connection of at least one liquid container (F1) to the arterial line (5) or the cell separator (7), characterized in that a bypass line (12) branches off from the plasma line (8A) and runs into the plasma line (8B), and the bypass line (12) comprises the second apheresis column (4"), a waste line (13) goes off directly from the apheresis column (4') or from the plasma line (8B) in the direction of flow before the junction of the bypass line (12), and at least one regeneration line (14) goes off from the at least one liquid container (F1) or the at least one connection line (11) and leads to the plasma line (8A) in the direction of flow at or after the junction of the bypass line (12) or runs directly into the apheresis column (4'), and at least a second regeneration line (14) goes off from at least one liquid container (F2), and wherein the second regeneration line (14) has no connection to the arterial line (5) or the cell separator (7) and leads in the direction of flow at or after the branch of the bypass line (12) to the plasma line (8A) or runs directly into the apheresis column (4'), wherein a second apheresis column (4") is connected in parallel with the first apheresis column (4') and both apheresis columns (4', 4") can only be operated alternately, i.e. cannot be used simultaneously for removal of CRP, wherein the apheresis device (II) is configured to be resistant to an alkali hydroxide solution, preferably a sodium hydroxide solution.

Preferably, the apheresis device (II) further comprises a central processing unit for controlling the apheresis device (II).

Preferably, the apheresis device (II) therefore comprises at least two regeneration lines (14', 14"), which lead independently of each other in the direction of flow at or after the branch of the bypass line (12) to the plasma line (8A) or run directly into the apheresis column (4'), wherein at least one of the regeneration lines (14', 14") goes off from the at least one liquid container (F1) or the at least one connection line (11).

Therefore, a further aspect of the present invention is an apheresis device (II) for extracorporeal removal of CRP from blood comprising:

an extracorporeal circulation system (2) for blood, a means (3) for generation and regulation of a flow of the blood in the extracorporeal circulation system (2), a cell separator (7) for separating the blood into blood plasma and cellular components, two apheresis columns (4', 4") for affinity chromatographic removal of CRP from the blood plasma, wherein the extracorporeal circulation system (2) comprises an arterial line (5) to the cell separator (7), a plasma line (8A) from the cell separator (7) to the apheresis column (4'), a plasma line (8B) for CRP-depleted blood plasma from the apheresis column (4') to a point (P1), a cell line (9) for the separated cellular components from the cell separator (7) to the point (P1), and a venous line (6) starting from the point (P1), at least one connection line (11) for connection of at least one liquid container (F1) to the arterial line (5) or the cell separator (7), characterized in that a bypass line (12) branches off from the plasma line (8A) and runs into the plasma line (8B), and the bypass line (12) comprises the second apheresis column (4"), a waste line (13) goes off directly from the apheresis column (4') or from the plasma line (8B) in the direction of flow before the junction of the bypass line (12), and at least one regeneration line (14) goes off from the at least one liquid container (F1) or the at least one connection line (11) and leads in the direction of flow at or after the branch of the bypass line (12) to the plasma line (8A) or runs directly into the apheresis column (4'), wherein the at least one regeneration line (14) has at least one additional connection for a liquid container (F2), wherein a second apheresis column (4") is connected in parallel with the first apheresis column (4') and both apheresis columns (4', 4") can only be operated alternately, i.e. cannot be used simultaneously for removal of CRP, wherein the apheresis device (II) is configured to be resistant to an alkali hydroxide solution, preferably a sodium hydroxide solution.

Preferably, the apheresis device (II) further comprises a central computing unit (10) for controlling the apheresis device (II).

The above-mentioned embodiments of the apheresis device (1) according to the invention are to be transferred to the apheresis device (II) according to the invention. The bypass line (12) of the apheresis device (1) is used as a plasma line in the apheresis device (II).

With the aid of this apheresis device (II) according to the invention, it is possible to remove CRP from blood more efficiently than with prior art devices for the same treatment time. By using two apheresis columns connected in parallel, which can only be used alternately for removal of CRP, one apheresis column can be used by means of the apheresis device according to the invention for the removal of CRP from the blood, while the second apheresis column can either be replaced by another apheresis column or the second apheresis column can be regenerated during the ongoing apheresis session. Thus, a high clinic throughput can also be achieved using an apheresis device. Furthermore, the use of the apheresis device according to the invention is not limited by the dead volume. Typically, oversized apheresis columns but also apheresis columns connected in series are severely limited in their use for apheresis by their large dead volume. In addition, the volume of an apheresis device and thus the volume or number of apheresis columns connected in series is limited by the flow rate of the human blood. Also, apheresis devices with apheresis columns connected in parallel and used simultaneously cannot be used efficiently for the removal of CRP from blood without risk to the patient due to the large dead volume.

An apheresis device (II) according to the invention, as described herein, is characterized in that a second apheresis column is connected in parallel with a first apheresis column (4'). "Parallel" in this context means that various circulations are present side by side within the extracorporeal circulation system (2), i.e. that, for example, a first apheresis column (4') with the plasma line (8A) for the separated plasma and with the plasma line (8B) for the CRP-depleted plasma represents a first circulation system of the extracorporeal circulation system (2), and a second apheresis column (4")

with the bypass line section (12') of the bypass line (12) and the bypass line section (12") of the bypass line (12) represents a second circulation system of the extracorporeal circulation system (2). “Parallel” also means that the two apheresis columns are not connected in series, i.e. not one after the other, so that the outflow of the first apheresis column is introduced into the second apheresis column. Due to the parallel arrangement of the apheresis columns their capacities also do not add up.

To be distinguished from this is the serial connection of the apheresis columns, which is not according to the invention. “Serial” means that several apheresis columns are only in one circulation of the extracorporeal circulation system (2), i.e. that, for example, the first apheresis column (4') and the second apheresis column (4") together with the plasma line (8A) and the plasma line (8B) form only one circulation of the extracorporeal circulation system (2), i.e. would be connected or arranged in series.

According to the invention, the two apheresis columns (4', 4") connected in parallel to each other or arranged in parallel can only be operated alternately. “Alternately” means that the separated blood plasma is passed either through the apheresis column (4') or through the apheresis column (4") but not simultaneously through both apheresis columns (4', 4"). “Alternately” operated in this context means therapeutic removal of CRP. Both apheresis columns (4' and 4") are not usable simultaneously for removal of CRP. Of course, one of the two apheresis columns can be regenerated while the other is used for CRP removal at the same time. Only the simultaneous therapeutic operation for removal of CRP of both apheresis columns is excluded.

The following states are therefore possible. Blood plasma is passed through one apheresis column to remove CRP. At the same time, the second apheresis column is ready for use and the plasma flow can be redirected to this second apheresis column as soon as the capacity of the first apheresis column is exhausted or other problems occur with the first apheresis column, or the second apheresis column has already been used for CRP removal and must be replaced or regenerated, or the second apheresis column is regenerated while the first one removes CRP.

In embodiments of the present invention, the apheresis device (II) with two apheresis columns is therefore configured such that the apheresis columns are only operable alternately.

Thus, according to an embodiment of the apheresis device (II) according to the invention, the blood plasma can be passed through either only the first apheresis column (4') or only through the second apheresis column (4") at the same time. In further embodiments of the device according to the invention, the apheresis device is thus designed in such a way that the blood plasma is passable either only through the first apheresis column (4') or only through the second apheresis column (4") at the same time.

During alternate operation of the two apheresis columns (4', 4"), no blood plasma is passed through either the apheresis column (4') or through the apheresis column (4"). This results in the possibility of replacing one of the two apheresis columns from the apheresis device during operation of the apheresis device. “Replacing” in this context means replacing one of the two apheresis columns with a new apheresis column or regenerating one of the two apheresis columns. Regeneration of one of the two apheresis columns can be done, for example, by rinsing with an alkali hydroxide solution, preferably a sodium hydroxide solution. The use of an alkali hydroxide solution, preferably a sodium hydroxide solution, is preferred for the regeneration of the apheresis columns. “During operation” in this context means that the removal of CRP from the blood still proceeds.

An embodiment of the apheresis devices (II) according to the invention, as described herein, therefore relates to an apheresis device in which a first apheresis column (4') is replaceable during operation of a second apheresis column (4") and the second apheresis column (4") is replaceable during operation of the first apheresis column (4').

Embodiments are also conceivable wherein a first apheresis column (4') is regenerable during operation of a second apheresis column (4") and the second apheresis column (4") is regenerable during operation of the first apheresis column (4').

Thus, in an embodiment of the present invention, the apheresis device (II) is designed such that a first apheresis column (4') is replaceable or regenerable during operation of a second apheresis column (4") and the second apheresis column (4") is replaceable or regenerable during operation of the first apheresis column (4').

Preferred is also an embodiment of the apheresis device (II) for extracorporeal removal of CRP from blood, wherein a second apheresis column (4") is connected in parallel with the first apheresis column (4') and both apheresis columns (4', 4") can be operated only alternately at the same time and wherein the first apheresis column (4') is replaceable or regenerable during operation of the second apheresis column (4") and the second apheresis column (4") is replaceable or regenerable during operation of the first apheresis column (4'), wherein the apheresis device (II) is configured to be resistant to an alkali hydroxide solution, preferably a sodium hydroxide solution.

Preferred is also an embodiment of the apheresis device (II) for extracorporeal removal of CRP from blood, wherein a second apheresis column (4") is connected in parallel with the first apheresis column (4') and both apheresis columns (4', 4") are not simultaneously usable for removal of CRP, and wherein one of the apheresis columns (4', 4") can be regenerated simultaneously with CRP removal by the other apheresis column, wherein the apheresis device (II) is configured to be resistant to an alkali hydroxide solution, preferably a sodium hydroxide solution.

Therefore, according to one embodiment of the present invention, the apheresis device (II) is configured such that the first apheresis column (4') is replaceable during operation of the second apheresis column (4") and the apheresis column is configured such that it is regenerable and the second apheresis column (4") is replaceable during operation of the first apheresis column (4') and is configured such that the apheresis column (4") is regenerable.

The second apheresis column (4") connected in parallel with the first apheresis column (4') can be integrated into the bypass line, i.e. the bypass line (12) is composed of a bypass line section (12') and a bypass line section (12"), wherein the second apheresis column (4") is located between said bypass line sections. Preferred is therefore an apheresis device (II) characterized in that a bypass line section (12') of the bypass line (12) branches off from the plasma line (8A) and runs into the second apheresis column (4') and the bypass line section (12") of the bypass line (12") runs into the plasma line (8B) starting from the apheresis column (4").

Preferred is also an embodiment of the apheresis device (II) for extracorporeal removal of CRP from blood, wherein a second apheresis column (4") is connected in parallel with the first apheresis column (4') and both apheresis columns (4', 4") cannot be used simultaneously for removal of CRP (i.e. can only be operated alternately), wherein the apheresis device (1) is configured to be resistant to an alkali hydroxide solution, preferably a sodium hydroxide solution.

According to an embodiment of the present invention, it is particularly preferred that the apheresis device (II) according to the invention has two connection lines (11', 11") each for the connection of at least one liquid container (F), wherein the connection lines (11', 11") run independently of each other into the arterial line (5) or directly into the cell separator (7). Consequently, both connection lines (11', 11") run into the arterial line (5) or both connection lines (11', 11") run directly into the cell separator (7) or, particularly preferably, one connection line (11') runs into the arterial line (5) and the other connection line (11") runs directly into the cell separator (7). This allows the two connection lines (11', 11") to be connected to different fluid containers.

According to a further embodiment of the present invention, the apheresis device (II) contains a waste line (13'), which goes off directly from apheresis column (4') or goes off from the plasma line (8B) in the direction of flow before the junction with the bypass line section (12") of the bypass into the plasma line (8B), and a waste line (13"), which goes off directly from the apheresis column (4") or from the bypass line section (12") in the direction of flow before the junction with the plasma line (8B).

Thus, the present invention also relates to an apheresis device (II) for extracorporeal removal of CRP from blood comprising:

an extracorporeal circulation system (2) for blood, a means (3) for generation and regulation of a flow of the blood in the extracorporeal circulation system (2)

a cell separator (7) for separation of the blood into blood plasma and cellular components, two apheresis columns (4', 4") for affinity chromatographic removal of CRP from blood plasma, wherein the extracorporeal circulation system (2) comprises an arterial line (5) to the cell separator (7), a plasma line (8A) from the cell separator (7) to the apheresis column (4'), a plasma line (8B) for CRP depleted blood plasma from the apheresis column (4') to a point (P1), a cell line (9) for the separated cellular components from the cell separator (7) to the point (P1), and a venous line (6) starting from the point (P1), at least one connection line (11) for connection of at least one fluid container (F) to the arterial line (5) or the cell separator (7), characterized in that a bypass line section (12') of the bypass line (12) branches off from the plasma line (8A) and runs into the second apheresis column (4'), and the bypass line section (12") of the bypass line (12") runs into the plasma line (8B) starting from the apheresis column (4"), a waste line (13') goes off directly from the apheresis column (4') or from the plasma line (8B) in the direction of flow before the junction of the bypass line section (12") of the bypass line (12), a waste line (13") goes off directly from the apheresis column (4") or from the plasma line (8B) in the direction of flow before the junction of the bypass line section (12") of the bypass line with the plasma line (8B), and a waste line (13") goes off directly from the apheresis column (4") or from the bypass line section (12") in the direction of flow before the junction with the plasma line (8B), and at least one regeneration line (14) runs into the plasma line (8A) or into the bypass line section (12') in the direction of flow after the branch of the bypass line section (12') of the bypass line (12) or runs directly into the apheresis column (4') or apheresis column (4"), and wherein a second apheresis column (4") is connected in parallel with the first apheresis column (4') and both apheresis columns (4', 4") cannot be used simultaneously for removal of, i.e. can only be operated alternately, wherein the apheresis device (II) is configured to be resistant to an alkali hydroxide solution, preferably a sodium hydroxide solution.

According to a further embodiment of the present invention, the apheresis device (II) further contains at least one regeneration line (14) that goes off from the at least one liquid container (F) or the at least one connection line (11) and leads into the plasma line (8A) or into the bypass line section (12') of the bypass line (12) or runs directly into the apheresis column (4') or directly into the apheresis column (4"). According to a further embodiment of the present invention, the apheresis device (II) further contains at least one regeneration line (14) that runs into the bypass line section (12') in a region from the point (P2) and the apheresis column (4') or runs into the plasma line (8A) in a region from the point (P2) and the apheresis column (4") or runs directly into the apheresis column (4') or leads directly into the apheresis column (4").

In a particularly preferred embodiment of the present invention, the apheresis device (II) comprises a waste line (13') which goes off directly from the apheresis column (4') or from the plasma line (8B) in the direction of flow before the junction of the bypass line section (12") of the bypass line (12) and at least one regeneration line (14), which goes off from the at least one liquid container (F) or the at least one connection line (11) and leads into the bypass line section (12') or into the plasma line (8A) or runs directly into the apheresis column (4') or directly into the apheresis column (4").

In a particularly preferred embodiment of the present invention, the apheresis device (II) comprises a waste line (13'), which goes off directly from the apheresis column (4') or from the plasma line (8B) in the direction of flow before the junction of the bypass line section (12") of the bypass line, a waste line (13") which goes off directly from the apheresis column (4") or from the bypass line section (12") of the bypass line (12) in the direction of flow before the junction of the bypass line section (12') of the bypass line, and at least one regeneration line (14) which goes off from the at least one liquid container (F) or the at least one connection line (11) and leads into the plasma line (8A) or into the bypass line section (12') of the bypass line (12) or runs directly into the apheresis column (4') or directly into the apheresis column (4").

Furthermore, embodiments of the apheresis device (II) according to the invention are possible, wherein the at least one regeneration line (14) runs to a point (P7) and from the point (P7) a line (15') leads to the point (P2) or runs into the plasma line (8A) and from the point (P7) a line (15") leads into plasma line (8A) (see FIG. 7).

In the case that the at least one regeneration line (14) for the rinsing solution runs into the plasma line (8A) between the point (P2) and the apheresis column (4') or in the case, that the at least one regeneration line (14) runs into the bypass line section (12') of the bypass line (12) between the point (P2) and the apheresis column (4"), the rinsing solution can be used either for the apheresis column (4') only or for the apheresis column (4"). The regeneration line (14) is thus either selective to the apheresis column (4') or selective to the apheresis column (4").

Likewise, embodiments of the apheresis device (II) according to the invention with two, three or more regeneration lines (14'. 14", 14'", etc.) are possible, wherein these two, three or more regeneration lines can run independently of each other into the plasma line (8A) [i.e. from the point (P2) to the apheresis column (4')] or into the bypass line section (12') [i.e. from the point (P2) to the apheresis column (4")] or into the apheresis column (4') or into the apheresis column (4"). “Independent of each other” means in this context, firstly, that in an embodiment of the apheresis devices according to the invention with two regeneration lines (14', 14"), one regeneration line (14') runs into the plasma line (8A) between the point (P2) and the apheresis column (4') and the other regeneration line (14") runs directly into the apheresis column (4"), but also that both regeneration lines (14', 14") can run into the plasma line (8A) between the point (P2) and the apheresis column (4'). Another possibility is that one regeneration line (14') runs into the extracorporeal circulation system (2) at the point (P2) and the other regeneration line (14") runs into the bypass line section (12') of the bypass line (12) between the point (P2) and the apheresis column (4"). It is also conceivable that one regeneration line (14') runs into the extracorporeal circulation system at the point (P2) and the other regeneration line (14") runs into the apheresis column (4"). It is also possible that one regeneration line (14') runs into the other regeneration line (14"). However, when two or more regeneration lines (14', 14", 14'", etc.) are present, it is preferred that all regeneration lines (14', 14", 14'", etc.) run into the extracorporeal circulation system (2) at the point (P2), wherein the apheresis device (II) is configured to be resistant to an alkali hydroxide solution, preferably a sodium hydroxide solution.

It is further preferred if one regeneration line (14') runs into the bypass line section (12') of the bypass line (12) between the point (P2) and the apheresis column (4') and the other regeneration line (14") runs into the bypass line section (12') of the bypass line (12) between the point P2 and the apheresis column (4"). It is further preferred if the regeneration line (14') runs into the apheresis column (4') and the other regeneration line (14") runs into the apheresis column (4"). Here, the regeneration line (14') is selective to the first apheresis column (4') and the regeneration line is selective to the second apheresis column (4").

According to a particularly preferred embodiment of the present invention, the apheresis device (II) therefore further comprises a regeneration line (14') for a rinsing solution selectively to the first apheresis column (4') and/or further comprises a regeneration line (14") for a rinsing solution selectively to the second apheresis column (4").

As mentioned above, the regeneration solution required for the regeneration of the apheresis columns can be fed into the extracorporeal circulation system (2) via the regeneration line (14), and thus a regeneration solution (e.g. alkali hydroxide solution, preferably sodium hydroxide solution) can also be used in addition to the rinsing solution. The rinsing solution can, but does not have to, serve to regenerate the first apheresis column (4') and/or apheresis column (4"), but in addition to the above-mentioned function, it has the task to displace the blood plasma from the plasma line (8A) in the region from point (P2) to the apheresis column (4') as well as from the plasma line (8B) from the apheresis column (4') to point (P8) or from the bypass line section (12') of the bypass line (12) in the region from point (P2) to the apheresis column (4") as well as from the bypass line section (12") of the bypass line (12) from the apheresis column (4") to the point (P8), before the regeneration solution is used, which after passing through one of the two apheresis columns (4', 4") is then discarded via the waste line (13', 13").

Thus, it is conceivable that the apheresis columns (4', 4") connected in parallel can not only be operated alternately, but also regenerated alternately.

In the apheresis devices (II) according to the invention, as described herein, the first apheresis column (4') may be replaceable or regenerable during operation of the second apheresis column (4") and the second apheresis column (4") may be replaceable or regenerable during operation of the first apheresis column (4').

In other words, apheresis devices (II) are preferred, wherein a second apheresis column (4") is connected in parallel with the first apheresis column (4') and both apheresis columns (4', 4") are only operable alternately, and wherein the first apheresis column (4') is replaceable or regenerable during operation of the second apheresis column (4") and the second apheresis column (4") is replaceable or regenerable during operation of the first apheresis column (4'), wherein the apheresis device (II) is configured to be resistant to an alkali hydroxide solution, preferably a sodium hydroxide solution.

Furthermore, embodiments of the present invention are conceivable in which the apheresis device has a regeneration line (14) for each liquid container (F), which goes off from the respective liquid container (F) or its connection line (11) and which leads in each case into the plasma line (8A) or into the bypass line section (12') of the bypass line (12) or directly into the apheresis column (4') or directly into the apheresis column (4").

A particularly preferred embodiment of the underlying invention relates to an apheresis device (II) for extracorporeal removal of CRP from blood comprising:

an extracorporeal circulation system (2) for blood, a means (3) for generation and regulation of a flow of the blood in the extracorporeal circulation system (2)

a cell separator (7) for separating the blood into blood plasma and cellular components, two apheresis columns (4', 4") for affinity chromatographic removal of CRP from blood plasma, wherein the extracorporeal circulation system (2) comprises an arterial line (5) to the cell separator (7), a plasma line (8A) from the cell separator (7) to the apheresis column (4'), a plasma line (8B) for CRP depleted blood plasma from the apheresis column (4') to a point (P1), a cell line (9) for separated cellular components from the cell separator (7) to the point (P1), and a venous line (6) starting from the point (P1), at least one connection line (11) for connection of at least one liquid container (F) to the arterial line (5) or the cell separator (7), characterized in that a bypass line section (12') of the bypass line (12) branches off from the plasma line (8A) and runs into the second apheresis column (4'), and the bypass line section (12") of the bypass line (12") runs into the plasma line (8B) starting from the apheresis column (4"), a waste line (13') goes off directly from the apheresis column (4') or from the plasma line (8B) in the direction of flow before the junction of the bypass line section (12') of the bypass line (12), a waste line (13") goes off directly from the apheresis column (4") or from the bypass line section (12") of the bypass line (12) in the direction of flow before the junction of the bypass line section (12') of the bypass line (12) and a regeneration line (14) is included for each liquid container (F) which goes off from the respective liquid container (F) or its connection line (11) and leads in the direction of flow after the branch of the bypass line section (12') of the bypass line (12) to the plasma line (8A) or to the bypass line section (12') of the bypass line (12) or runs directly into the apheresis column (4') or directly into the apheresis column (4"), and wherein a second apheresis column (4") is connected in parallel with the first apheresis column (4') and both apheresis columns (4', 4") cannot be used simultaneously for removal of CRP, wherein the apheresis device (II) is configured to be resistant to an alkali hydroxide solution, preferably a sodium hydroxide solution.

Furthermore, embodiments of the apheresis device (II) are preferred in which the apheresis device (II) has at least two connection lines (11) each for connection of at least one liquid container (F) to the arterial line (5) or the cell separator (7), and wherein there is a regeneration line (14) for each liquid container (F), which goes off from the respective liquid container (F) or its connection line (11) and which respectively lead into the plasma line (8A) or into the bypass line section (12') of the bypass line (12) or directly into the apheresis column (4') or directly into the apheresis column (4").

According to some embodiments of the present invention, it is preferred that at least one regeneration line (14) leading into the plasma line (8A) or into the bypass line section (12') of the bypass line (12) or running directly into the apheresis column (4') or directly into the apheresis column (4") starts from a point (P5) in the at least one connection line (11).

An apheresis device (II) is preferred, wherein the apheresis device (II) has two connection lines (11', 11') each for connection of one liquid container (F1, F2) to the arterial line (5) or the cell separator (7), and two regeneration lines (14', 14") go off from two liquid containers (F1, F2) or the two connection lines (11', 11") and lead into the plasma line (8A) or into the bypass line section (12') of the bypass line (12) or directly into apheresis column (4') or directly the apheresis column (4").

Particularly preferred are embodiments in which a regeneration line (14), which leads into the plasma line (8A) or into the bypass line section (12') of the bypass line (12) or directly into the apheresis column (4') or directly into the apheresis column (4") and which starts from a point (P5) in the at least one connection line (11), has at least one additional connection for a liquid container (FIG. 10). For example, an infusion bag containing alkali hydroxide solution, preferably sodium hydroxide solution, can be connected to this additional connection.

In embodiments of the present invention with a plurality of connection lines (11', 11", 11'", etc.) and a plurality of regeneration lines (14', 14", 14'", etc.), it is possible that each connection line is in communication with a respective regeneration line, which in turn run after the point (P2) into the plasma line (8A) or into the bypass line section (12') of the bypass line (12) or directly into apheresis column (4') or directly into the apheresis column (4"). Here, each regeneration line can run independently of the other regeneration lines into the plasma line (8A) or into the bypass line section (12') of the bypass line (12) or directly into apheresis column (4') or directly into apheresis column (4"). However, it is preferred that all regeneration lines run directly into apheresis columns (4'; 4"), preferably at point (P2) in the extracorporeal circulation system (2). Such an exemplary embodiment may be explained with reference to FIG. 10. Herein, the apheresis device (II) has a first connection line (11'), which firstly leads into the arterial line (5) and from which secondly a first regeneration line (14') branches off at point (P5'). The apheresis device (II) also has a second connection line (11"), which firstly leads directly into the cell separator (7) and from which secondly a second regeneration line (14") branches off at point (P5"). In this embodiment, both regeneration lines run into the extracorporeal circulation system (2) at point (P2).

Accordingly, an apheresis device (II) is preferred, wherein the apheresis device (II) has two connection lines (11', 11") each for the connection of at least one liquid container (F) to the arterial line (5) or the cell separator (7), and wherein the at least one regeneration line (14), which leads into the plasma line (8A) or into the bypass line section (12') of the bypass line (12) or directly into the apheresis column (4') or directly into the apheresis column (4"), connects at a point (P5') to the connection line (11') and at a point (P5") to the connection line (11").

Thus, embodiments of the apheresis device are particularly preferred, wherein the apheresis device (II) has two connection lines (11', 11") each for connection of a liquid container (F1, F2) to the arterial line (5) or the cell separator (7), and wherein at least one regeneration line (14) leading into the plasma line (8A) or into the bypass line section (12') of the bypass line (12) or directly the apheresis column (4') or directly into the apheresis column (4") connects at a point (P5') to the connection line (11') and at a point (P5") to the connection line (11"), and wherein a regeneration line (14') leads from the liquid container (F1) or from the connection line (11') going off from the liquid container (F1) to the apheresis column (4') or to the apheresis column (4") or to the plasma line (8A') or to the plasma line (8A") and a regeneration line (14") leads from the liquid container (F2) or the connection line (11") going off from the liquid container (F2) to the apheresis column (4') or to the apheresis column (4") or to the plasma line (8A) or to the bypass line section (12') of the bypass line (12) or to the regeneration line (14').

Thus, it is particularly preferred that the apheresis device (II) has a connection line (11') for the connection of a liquid container (F1) and a connection line (11") for the connection of a liquid container (F2), and the connection line (11') runs into the arterial line (5) or into the cell separator (7), and the connection line (11") runs into the arterial line (5) or into the cell separator (7) or into the connection line (11') and thus ultimately also into the arterial line (5) or into the cell separator (7), and a regeneration line (14') leads from the liquid container (F1) or from the connection line (11') to the apheresis column (4') or to the apheresis column (4") or to the plasma line (8A) or to the plasma line (8A). (8A") and a regeneration line (14") leads from the liquid container (F2) or from the connection line (11") to the apheresis column (4') or to the apheresis column (4") or to the plasma line (8A') or to the bypass line section (12') of the bypass line section (12') of the bypass line (12) or to the regeneration line (14').

Embodiments of the apheresis device (II) are therefore particularly preferred, wherein the apheresis device (II) has a connection line (11') for connection of a liquid container (F1) to the arterial line (5) or the cell separator (7) and a connection line (11") for connection of a liquid container (F2) to the arterial line (5) or the cell separator (7), and wherein a regeneration line (14') goes off from the liquid container (F1) or the connection line (11') and runs into the plasma line (8A) or the bypass line section (12') of the bypass line (12) or directly into the apheresis column (4') or directly into the apheresis column (4") and a regeneration line (14") goes off from a liquid container (F2) or the connection line (11") and runs into the plasma line (8A) or into the bypass line section (12') of the bypass line (12) or into the regeneration line (14') or directly into the apheresis column (4') or directly into the apheresis column (4").

Therefore, the present invention is also directed to an apheresis apparatus (II) according to the present invention, wherein the plasma line (8A) and the bypass line section (12') of the bypass line (12) diverge from a point (P2), and the plasma line (8B) and the bypass line section (12") of the bypass line (12) plasma line (8B) converge at the point (P6) and the waste line (13') goes off from a point (P4) from the plasma line (8B) and the waste line (13") goes off from a point (P8) from the bypass line section (12") of the bypass line (12), and the at least one regeneration line (14) runs into the extracorporeal circulation system (2) at the point (P2).

A preferred embodiment of the underlying invention relates to an apheresis device (II) for extracorporeal removal of CRP from blood comprising:

an extracorporeal circulation system (2) for blood, a means (3) for generation and regulation of a flow of the blood in the extracorporeal circulation system (2)

a cell separator (7) for separation of the blood into blood plasma and cellular components, two apheresis columns (4', 4") for affinity chromatographic removal of CRP from blood plasma, wherein the extracorporeal circulation system (2) comprises an arterial line (5) to the cell separator (7), a plasma line (8A) from the cell separator (7) to the apheresis column (4'), a plasma line (8B) for CRP depleted blood plasma from the apheresis column (4') to a point (P1), a cell line (9) for separated cellular components from the cell separator (7) to the point (P1), and a venous line (6) starting from the point (P1), at least one connection line (11) for connection of at least one liquid container (F) to the arterial line (5) or the cell separator (7), characterized in that a bypass line section (12') of the bypass line (12) branches off from the plasma line (8A) and runs into the second apheresis column (4'), and the bypass line section (12") of the bypass line (12") runs into the plasma line (8B) starting from the apheresis column (4"), a waste line (13') goes off directly from the apheresis column (4') or from the plasma line (8B) in the direction of flow before the junction of the bypass line section (12') of the bypass line (12), a waste line (13") goes off directly from the apheresis column (14") or from the bypass line section (12") of the bypass line (12) in the direction of flow before the junction of the bypass line section (12') of the bypass line (12), wherein the plasma line (8A) and the bypass line section (12') of the bypass line (12) diverge from a point (P2), and the plasma line (8B) and the bypass line section (12") of the bypass line (12) converge at a point (P6), and at least one regeneration line (14) leads in the direction of flow after the bypass line section (12') of the bypass line (12) to the plasma line (8A) or to the bypass line section (12') of the bypass line (12) or runs directly into the apheresis column (4') or directly into the apheresis column (4"), and the waste line (13') goes off from a point (P4) from the plasma line (8B) and the waste line (13") goes off from a point (P8) from the bypass line section (12") of the bypass line (12), and the at least one regeneration line (14) runs into the extracorporeal circulation system (2) at the point (P2), and wherein a second apheresis column (4") is connected in parallel with the first apheresis column (4') and both apheresis columns (4', 4") cannot be used simultaneously for removal of CRP, i.e. can only be used alternately, wherein the apheresis device (II) is configured to be resistant to an alkali hydroxide solution, preferably a sodium hydroxide solution.

To further reduce the dead volume of the system, it is even further preferred if not only the regeneration line (14) runs into the extracorporeal circulation system at the point (P2) where the plasma line (8A) and the bypass line section (12') of the bypass line (12) diverge, but also that the waste lines (13', 13") branch off from the same point (P6) where the plasma line (8B) and the bypass line section (12") of the bypass line (12) converge. In other words, it is preferred when the point (P6) where the plasma line (8B) and the bypass line section (12") of the bypass line (12) converge, and the point (P8) where the waste line (13") branches off and the point (P4) where waste line (13') branches off coincide, i.e., when P8=P4=P6 (see FIG. 8).

Therefore, the present invention is also directed to an apheresis apparatus (II) according to the present invention, wherein the plasma line (8B) and the bypass line section (12") of the bypass line (12) converge at a point (P6), and the waste line (13") goes off from a point (P8) from the bypass line section (12") of the bypass line (12), and the waste line (13') goes off from a point (P4) from the plasma line (8B), and the at least one regeneration line (14) runs into the extracorporeal circulation system (2) at the point (P2), and wherein the point (P6), the point (P4) and the point (P8) are identical.

In accordance with the present invention, an embodiment of the apheresis device (II) for extracorporeal removal of CRP from blood according to the invention comprises two apheresis columns (4', 4") for affinity chromatographic removal of CRP from blood or blood plasma, the function of which is to bind CRP present in the blood or blood plasma of a patient and which is passed through the apheresis column (4') or (4").

Method

A further aspect of the present invention also relates to a method for regeneration of an apheresis column (4) for affinity chromatographic removal of CRP in an apheresis device (1), the method enabling regeneration during operation and being characterized by the following steps:

(A) starting the redirection of separated plasma from the plasma line (8A) to the bypass line (12), thereby stopping the introduction of separated plasma from the plasma line (8A) into the apheresis column (4), (B) starting the introduction of regeneration solution via the at least one regeneration line (14) into the plasma line (8A) or directly into the apheresis column (4), wherein the regeneration solution is an alkali hydroxide solution, preferably a sodium hydroxide solution, (C) starting the redirection of the liquid flow exiting the apheresis column (4) from the plasma line (8B) to the waste line (13), (D) stopping the introduction of regeneration solution, (E) starting the introduction of neutralization solution, (F) stopping the introduction of neutralization solution and stopping the redirection of the separated plasma from the plasma line (8A) into the bypass line (12), thereby introduction of the separated plasma from the plasma line (8A) into the apheresis column (4), (G) closing the waste line (13) and forwarding the liquid flow exiting the apheresis column (4) into the venous line (6).

A further aspect of the present invention also relates to a method for regeneration of an apheresis column (4) for affinity chromatographic removal of CRP in an apheresis device (1), the method enabling regeneration during operation and comprises the following steps:

(A) starting the redirection of the separated plasma from the plasma line (8A) into the bypass line (12), thereby stopping the introduction of the separated plasma from the plasma line (8A) into the apheresis column (4), (B) starting the introduction of regeneration solution via the at least one regeneration line (14) into the plasma line (8A) or directly into the apheresis column (4), wherein the regeneration solution is an alkali hydroxide solution, preferably a sodium hydroxide solution, (C) starting the redirection of the liquid flow exiting the apheresis column (4) from the plasma line (8B) to the waste line (13), (D) stopping the introduction of regeneration solution, (E) starting the introduction of neutralization solution, (F) stopping the introduction of neutralization solution.

A further aspect of the present invention also relates to a method for regeneration of an apheresis column (4) for affinity chromatographic removal of CRP in an apheresis device (1), the method enabling regeneration during operation and comprises the following steps:

(A) starting the redirection of the separated plasma from the plasma line (8A) into the bypass line (12), thereby stopping the introduction of separated plasma from the plasma line (8A) into the apheresis column (4), (B) starting the introduction of regeneration solution via the at least one regeneration line (14) into the plasma line (8A) or directly into the apheresis column (4), wherein the regeneration solution is an alkali hydroxide solution, preferably a sodium hydroxide solution, (C) starting the redirection of the liquid flow exiting the apheresis column (4) from the plasma line (8B) into the waste line (13), (D) stopping the introduction of regeneration solution, (E) starting the introduction of neutralization solution, (F) stopping the introduction of neutralization solution and stopping the redirection of the separated plasma from the plasma line (8A) into the bypass line (12), thereby introduction of the separated plasma from the plasma line (8A) into the apheresis column (4), (G) closing the waste line (13).

A further aspect of the present invention also relates to a method for regeneration of an apheresis column (4) for affinity chromatographic removal of CRP in an apheresis device (1), the method enabling regeneration during operation and comprises the following steps:

(A) starting the redirection of the separated plasma from the plasma line (8A) into the bypass line (12), thereby stopping the introduction of the separated plasma from the plasma line (8A) into the apheresis column (4), (B) starting the introduction of regeneration solution via the at least one regeneration line (14) into the plasma line (8A) or directly into the apheresis column (4), wherein the regeneration solution is an alkali hydroxide solution, preferably a sodium hydroxide solution, (C) starting the redirection of the liquid flow exiting the apheresis column (4) from the plasma line (8B) to the waste line (13), (D) stopping the introduction of regeneration solution, (E) starting the introduction of neutralization solution, (F) stopping the introduction of neutralization solution and stopping the redirection of the separated plasma from the plasma line (8A) into the bypass line (12), thereby introduction of the separated plasma from the plasma line (8A) into the apheresis column (4).

The term "stopping the introduction of the separated plasma" according to step (A) may be understood to mean, depending on the embodiment of the present invention, the use of hose clamps, control elements, valves and/or hose pumps for preventing the further flow of blood plasma into the plasma line (8A) or into the bypass line section (12') of the bypass line (12) or into the apheresis column (4') or (4").

The term "stopping the introduction of regeneration solution" according to step (D) may be understood to mean, depending on the embodiment of the present invention, the use of hose clamps, control elements, valves and/or peristaltic pumps to prevent further flow of regeneration solution into the plasma line (8A) or into the apheresis column (4). Here, it is to be understood that in embodiments where only one regeneration solution is used, the introduction of the same is stopped. In embodiments in which several regeneration solutions are successively introduced, this means that the introduction of the last regeneration solution used is stopped and thus also the introduction of any regeneration solution is stopped.

The term "closing the waste line (13)" according to step (E) may be understood to mean, depending on the embodiment of the present invention, the use of hose clamps, control elements, valves and/or hose pumps to prevent further flow of the liquid flow exiting the apheresis column (4). Here, it is to be understood that in embodiments in which only one regeneration solution is used, the introduction of the same is stopped. In embodiments in which several regeneration solutions are successively introduced, it is to be understood that the introduction of the last regeneration solution used is stopped, and thus also the introduction of any regeneration solution is stopped.

By "forwarding the liquid flow exiting the apheresis column (4)" according to step (E), the separated plasma henceforth flows back into the plasma line (8B) after passing through the apheresis column (4) and from there on through the venous line (6). Depending on the embodiment of the present invention, hose clamps, control elements, valves and/or hose pumps may be used to change the direction of flow of the liquid flow exiting the apheresis column (4).

Further, the present invention relates to a method for regeneration of an apheresis column (4) for affinity chromatographic removal of CRP in an apheresis device (1), as described herein, wherein the method enables regeneration during operation by switching from an apheresis mode to a regeneration mode, wherein in the apheresis mode plasma that is separated from blood by means of the cell separator (7) is directed into the apheresis column (4) via the plasma line (8A), and the liquid flow exiting the apheresis column (4) is directed into the venous line (6) via the plasma line (8B)

and wherein the regeneration mode is characterized by the following steps:

(A) starting the redirection of the separated plasma from the plasma line (8A) into the bypass line (12), thereby stopping the introduction of the separated plasma from the plasma line (8A) into the apheresis column (4), (B) starting the introduction of regeneration solution via the at least one regeneration line (14) into the plasma line (8A) or directly into the apheresis column (4), wherein the regeneration solution is an alkali hydroxide solution, preferably a sodium hydroxide solution, (C) starting the redirection of the liquid flow exiting the apheresis column (4) from the plasma line (8B) to the waste line (13), (D) stopping the introduction of regeneration solution, (E) starting the introduction of neutralization solution, (F) stopping the introduction of neutralization solution and stopping the redirection of the separated plasma from the plasma line (8A) into the bypass line (12), thereby direction of the separated plasma from the plasma line (8A) into the apheresis column (4), (E) closing the waste line (13).

A step (E) closing the waste line (13) and switching to apheresis mode is preferred. A step (E) closing the waste line (13) and forwarding the liquid flow exiting the apheresis column (4) into the venous line (6), and thus again a switching to apheresis mode is further preferred.

With respect to the two aforementioned methods, the regeneration solution is preferably an alkali hydroxide solution, preferably a sodium hydroxide solution.

Furthermore, methods are preferred in which step (C) is initiated after a total volume X of regeneration solution(s) has been introduced into the plasma line (8A) or directly into the apheresis column (4), wherein X corresponds to at least 75% of the volume of the device between the point where the regeneration line (14) runs into the extracorporeal circulation system (2) in the direction of flow after the branch of the bypass line (12) and the point where the waste line (13) starts from the extracorporeal circulation system (2). Here, the regeneration solution is, for example, an alkali hydroxide solution, preferably a sodium hydroxide solution.

In addition, methods are preferred in which step (E) is initiated after a volume Y of plasma has been introduced into the plasma line (8A) or directly into the apheresis column (4), wherein Y is at least 90% of the volume of the device between the point, at which the regeneration line (14) runs into the extracorporeal circulation system (2) in the direction of flow after the branch of the bypass line (12) and the point at which the waste line (13) starts from the extracorporeal circulation system (2).

"During operation", as used herein, means that in order to carry out the method for regeneration of an apheresis column (4) according to the invention, the blood collection and supply as well as the operation of the cell separator do not have to be stopped. In other words, during the method for regeneration of an apheresis column (4) according to the invention, the continuously collected plasma is combined with the cell components via the bypass line (12), bypassing the apheresis column (4), and is supplied to the patient. During regeneration, the apheresis column is thus decoupled from the blood collection and supply or blood circulation. During the time in which the plasma is redirected via the bypass line (12), the apheresis column (4), which is usually reduced in capacity, is regenerated. Thus, the patient's circulation is not stressed because the continuously withdrawn blood is returned to the patient without delay.

"During operation", as used herein, accordingly does not mean that continuous plasma collection must be interrupted in order to carry out the method of the invention for regeneration of an apheresis column (4). Furthermore, it also does not mean that CRP depletion takes place during the regeneration of the apheresis column.

Thus, in both of the foregoing methods and the methods generally disclosed herein, it is preferred that the introduction of regeneration solution comprise the introduction of a single regeneration solution or the successive introduction of several regeneration solutions.

For the skilled person it is absolutely clear that an initial rinsing step of the adsorber or of the entire system must have taken place before the execution of the method according to the invention. This is associated with a pre-filling of the entire tube system. For this purpose, further connections may be present on the system under certain circumstances, which enable the entire system to be flushed. After the patient has been separated from the tube system, there is the possibility of preservation of the adsorber so that it can be used again for further treatment on the same patient.

In other words, the present invention also relates to a method according to the invention for regeneration of an apheresis column (4) for affinity chromatographic removal of CRP in the apheresis device (1), wherein the method enables regeneration during operation and is characterized by the following steps:

(A) redirecting the separated plasma from the plasma line (8A) to the bypass line (12), (B) introducing at least one regeneration solution from a liquid container via the regeneration line (14) into the plasma line (8A) or directly into the apheresis column (4), wherein the regeneration solution is an alkali hydroxide solution, preferably a sodium hydroxide solution, (C) redirecting the liquid flow exiting the apheresis column (4) from the plasma line (8B) to the waste line (13), (D) stopping the introduction of the regeneration solution, (E) starting the introduction of neutralization solution, (F) redirecting the separated plasma from the plasma line (8A) into the apheresis column (4) and stopping the introduction of neutralization solution, (G) closing the waste line (13).

A step (G) closing the waste line (13) and forwarding the liquid flow exiting the apheresis column (4) into the venous line (6) is preferred.

The term "redirection", as used herein, refers to a change in the direction of flow of the liquid in question. During the treatment mode, the separated plasma flows through the plasma line (8A) into the apheresis column (4). After leaving the apheresis column (4), the depleted plasma flows through the plasma line (8B) into the venous line (6).

By the "redirection" of the direction of flow of the separated plasma according to step (A), the separated plasma henceforth no longer flows through the apheresis column (4), but bypasses it by being redirected into the bypass line (12).

The term "introduction", as used herein, according to step (B) may be understood to mean, depending on the embodiment of the present invention, the feeding of at least one regeneration solution (using or actuating hose clamps, control elements, valves and/or hose pumps) into the plasma line (8A) or into the apheresis column (4).

By "redirection" of the direction of flow of the liquid flow exiting the apheresis column (4) according to step (C), the exiting liquid henceforth no longer flows into the plasma line (8B) but directly into the waste line (13). According to the invention, it is preferred that the waste line (13) branches off directly or immediately from or after the apheresis column (4), in order to minimize the volume of regeneration solution required to regenerate the apheresis column (4). In the spirit of the invention, the waste line (13) can also branch off from the plasma line (8B) and thus does not have to branch off directly from the apheresis column.

By the "redirection" of the direction of flow of the separated plasma according to step (D), the separated plasma henceforth flows again through the apheresis column (4) and no longer into the bypass line (12). In certain embodiments, a pump is provided in the bypass line (12), whereby the plasma present in the bypass line (12) is pumped into the plasma line (8B) and via the venous line (6) after redirection according to step (D). Here, preferably, the plasma present in the bypass line is displaced by a NaCl solution from the regeneration line (14). Preferably, this is a 0.9% NaCl solution. It would also be conceivable that a separate liquid container can be connected to the bypass line (12), through which said NaCl solution is provided for displacement.

Therefore, a method for regeneration of an apheresis column (4) for affinity chromatographic removal of CRP in an apheresis device (1) is particularly preferred, wherein the method is characterized by the following steps:

(A) starting the redirection of the separated plasma from the plasma line (8A) into the bypass line (12), thereby stopping the introduction of the separated plasma from the plasma line (8A) into the apheresis column (4), (B) starting the introduction of a rinsing solution via the at least one regeneration line (14) into the plasma line (8A) or directly into the apheresis column (4), (C) starting the redirection of the liquid flow exiting the apheresis column (4) from the plasma line (8B) to the waste line (13), (D) stopping the introduction of the rinsing solution and transition to the introduction of a regeneration solution via the at least one regeneration line (14) into the plasma line (8A) or directly into the apheresis column (4), wherein the regeneration solution is an alkali hydroxide solution, preferably a sodium hydroxide solution, (E) stopping the introduction of the regeneration solution and transition to the introduction of the rinsing solution via the at least one regeneration line (14) into the plasma line (8A) or directly into the apheresis column (4), (F) stopping the introduction of rinsing solution and stopping the redirection of the separated plasma from the plasma line (8A) into the bypass line (12) and thereby direction of the separated plasma from the plasma line (8A) into the apheresis column (4);

(G) closing the waste line (13).

A step (G) closing the waste line (13) and forwarding the fluid flow exiting the apheresis column (4) into the venous line (6) is preferred.

Alternatively, a method for regeneration of an apheresis column (4) for affinity chromatographic removal of CRP in an apheresis device (1) is particularly preferred, wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a rinsing solution via the at least one regeneration line (14) into the plasma line (8A) or directly into the apheresis column (4), (C) stopping the introduction of the rinsing solution and transition to the introduction of a regeneration solution via the at least one regeneration line (14) into the plasma line (8A) or directly into the apheresis column (4), wherein the regeneration solution is an alkali hydroxide solution, preferably a sodium hydroxide solution, (D) starting the redirection of the liquid flow exiting the apheresis column (4) from the plasma line (8B) to the waste line (13), (E) stopping the introduction of the regeneration solution and transition to the introduction of the rinsing solution via the at least one regeneration line (14) into the plasma line (8A) or directly into the apheresis column (4), (F) closing the waste line (13);

(G) stopping the introduction of rinsing solution and stopping the redirection of the separated plasma from the plasma line (8A) into the bypass line (12) and thereby direction of the separated plasma from the plasma line (8A) into the apheresis column (4).

A step (F) closing the waste line (13) and forwarding the liquid flow exiting the apheresis column (4) into the venous line (6) is preferred.

In both of the above methods, a rinsing solution is used in addition to the regeneration solution. The rinsing solution is preferably physiologically compatible and serves primarily to displace the blood plasma from the plasma line (8A) from point P2, from the apheresis column (4) and from the plasma line (8B) to point P4. The rinsing solution serves less or not at all for the regeneration of the apheresis column (4). Only when the blood plasma has been largely to completely displaced from the section of the apheresis device (1) to be flushed with regeneration solution the regeneration solution is introduced to regenerate the apheresis column (4). After regeneration has taken place, rinsing solution is then first fed again into the section of the apheresis device (1) that has been flushed with regeneration solution (i.e. in the direction of flow from point P2 through the apheresis column (4) to point P4) until the regeneration solution has been completely discarded through the waste line (13). Only then is the bypass line (12) closed and blood plasma is again passed through the apheresis column (4). In the two aforementioned methods, steps (C) and (D) can be interchanged, i.e. can be performed in any order and also simultaneously, and can also be combined in one step. However, execution of step (D) before step (C) is preferred.

In this method, the rinsing solution is preferably a physiological NaCl solution or PBS solution and the regeneration solution is an alkali hydroxide solution, preferably a sodium hydroxide solution.

Therefore, a method for regeneration of an apheresis column (4) for affinity chromatographic removal of CRP in an apheresis device (1) is particularly preferred, wherein the method is characterized by the following steps:

(A) starting to the redirection of the separated plasma from the plasma line (8A) into the bypass line (12), thereby stopping the direction of the separated plasma from the plasma line (8A) into the apheresis column (4), (B) starting the introduction of a rinsing solution via the at least one regeneration line (14) into the plasma line (8A) or directly into the apheresis column (4), (C) starting the redirection of the liquid flow exiting the apheresis column (4) from the plasma line (8B) to the waste line (13), (D) stopping the introduction of the rinsing solution and transition to the introduction of a regeneration solution via the at least one regeneration line (14) into the plasma line (8A) or directly into the apheresis column (4), wherein the regeneration solution is an alkali hydroxide solution, preferably a sodium hydroxide solution, (E) stopping the introduction of the regeneration solution and transition to the introduction of the neutralization solution via the at least one regeneration line (14) into the plasma line (8A) or directly into the apheresis column (4), (F) stopping the introduction of the neutralization solution and transition to the introduction of the rinsing solution via the at least one regeneration line (14) into the plasma line (8A) or directly into the apheresis column (4), (G) stopping the introduction of the rinsing solution and stopping the redirection of the separated plasma from the plasma line (8A) into the bypass line (12) and thereby direction of the separated plasma from the plasma line (8A) into the apheresis column (4);

(H) closing the waste line (13).

A step (H) closing the waste line (13) and forwarding the liquid flow exiting the apheresis column (4) into the venous line (6) is preferred.

Alternatively, a method for regeneration of an apheresis column (4) for affinity chromatographic removal of CRP in an apheresis device (1) is particularly preferred, wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a rinsing solution via the at least one regeneration line (14) into the plasma line (8A) or directly into the apheresis column (4), (C) stopping the introduction of the rinsing solution and transition to the introduction of a regeneration solution via the at least one regeneration line (14) into the plasma line (8A) or directly into the apheresis column (4), wherein the regeneration solution is an alkali hydroxide solution, preferably a sodium hydroxide solution, (D) starting the redirection of the liquid flow exiting the apheresis column (4) from the plasma line (8B) to the waste line (13), (E) stopping the introduction of the regeneration solution and transition to the introduction of the neutralization solution via the at least one regeneration line (14) into the plasma line (8A) or directly into the apheresis column (4), (F) stopping the introduction of the neutralization solution and transition to the introduction of the rinsing solution via the at least one regeneration line (14) into the plasma line (8A) or directly into the apheresis column (4), (G) closing the waste line (13);

(H) stopping the introduction of the rinsing solution and stopping the redirection of the separated plasma from the plasma line (8A) into the bypass line (12) and thereby direction of the separated plasma from the plasma line (8A) into the apheresis column (4).

A step (G) closing the waste line (13) and forwarding the liquid flow exiting the apheresis column (4) into the venous line (6) is preferred.

In both aforementioned methods, steps (C) and (D) are interchangeable, i.e. can be performed in any order and also simultaneously, and can also be combined in one step. However, execution of step (D) before step (C) is preferred.

The preferred embodiment of the method according to the invention serves for more efficiently execution of the method without loss of blood plasma. Due to the simultaneous redirection of the separated plasma and the parallel introduction of the rinsing solution into the apheresis column (4), there is no loss or no significant loss of blood plasma. Furthermore, an advantage of the preferred embodiment is that mixing of the regeneration solution and blood plasma is completely avoided. This ensures that no regeneration solution enters the patient and, on the other hand, no loss of blood plasma occurs for the patient.

This is ensured by the sequential order of steps (B) to (E). Dilution of the blood plasma takes place only through rinsing solution, if at all. On the other hand, mixing of blood plasma with regeneration solution is completely avoided.

The volume of rinsing solution according to step (B) preferably corresponds to 3 to 4 times the volume of the matrix of the apheresis column (4).

Minimally, the volume of rinsing solution according to step (B) corresponds to the volume of the plasma line (8A) from point P2 to the apheresis column (4) plus the volume of the matrix of the apheresis column (4) and plus the volume of the plasma line (8B) from the apheresis column (4) to point P4.

The volume of regeneration solution according to step (C) is preferably 2 to 100 times the volume of the matrix of the apheresis column (4).

The volume of rinsing solution according to step (E) preferably corresponds to 2 to 4 times the volume of the matrix of the apheresis column (4).

At least the volume of rinsing solution according to step (E) corresponds to the volume of the plasma line (8A) from point P2 to the apheresis column (4) plus the volume of the matrix of the apheresis column (4) and plus the volume of the plasma line (8B) from the apheresis column (4) to point P4.

According to this even more preferred embodiment, dilution of the plasma is largely avoided and mixing with regeneration solution is completely prevented. The user is not confronted with too much complexity regarding the use of the apheresis device (1). In an alternative embodiment, the method steps can thus also be operated manually without appearing or being too complex for the user.

The "volume of the matrix of the apheresis column", as used herein, means the volume of the solid phase within the column, which in turn comprises a matrix substrate material and compounds bound thereto that have the property of specifically binding CRP. To be distinguished from this is the "dead volume of the apheresis column," i.e. the space within the column available to the mobile phase (e.g. plasma). The "dead volume of the apheresis column" is the difference between the volume enclosed by the apheresis column housing and the volume occupied by the swollen matrix (i.e. the "volume of the matrix of the apheresis column").

A further aspect of the present invention is directed to a method for regeneration of an apheresis column (4') for affinity chromatographic removal of CRP during operation of a second apheresis column (4") in an apheresis device (II) comprising the following steps:

(A) beginning from the flow of blood plasma through the apheresis column (4"), starting the introduction of the separated blood plasma into the apheresis column (4') via the plasma line (8A), and stopping the introduction of the separated plasma into the apheresis column (4") via the bypass line section (12') of the bypass line (12), (B) starting the introduction of regeneration solution via the at least one regeneration line (14) into the bypass line section (12') of the bypass line (12) or directly into the apheresis column (4"), wherein at least one regeneration solution is an alkali hydroxide solution, preferably a sodium hydroxide solution, (C) starting redirection of the liquid flow exiting the apheresis column (4") from the bypass line section (12") of the bypass line (12) to the waste line (13"), (D) starting the introduction of a neutralization solution via the at least one regeneration line (14) into the bypass line section (12') of the bypass line (12) or directly into the apheresis column (4"), (E) stopping the introduction of the neutralization solution, (F) starting the introduction of the separated blood plasma via the bypass line section (12') of the bypass line (12) into the apheresis column (4") and stopping the introduction of the separated blood plasma via the plasma line (8A) into apheresis column (4'), (G) closing the waste line (13") and starting the redirection of the liquid flow exiting the apheresis column (4') from the plasma line (8B) into the waste line (13').

A step (A) beginning from the flow of blood plasma through the apheresis column (4"), starting the introduction of the separated blood plasma into the apheresis column (4') via the plasma line (8A) and direction of the CRP-depleted blood plasma into the venous line (6), thereby stopping the introduction of the separated plasma into the apheresis column (4") via the bypass section (12') of the bypass line (12) is preferred.

A step (F) starting the introduction of the separated blood plasma via the bypass line section (12') of the bypass line (12) into the apheresis column (4") and direction of the CRP-depleted plasma into the venous line (6), thereby stopping the introduction of the separated blood plasma via the plasma line (8A) into apheresis column (4') is preferred.

"During operation", as used in this context, means that in order to carry out the method of the invention for regeneration of an apheresis column (4') or regeneration of an apheresis column (4"), it is not necessary to stop the blood collection and supply and the operation of the cell separator. Thus, the patient's circulation is not stressed because the continuously drawn blood is returned to the patient without delay.

In other words, in one embodiment, the present invention relates to a method for regeneration of an apheresis column (4') for affinity chromatographic removal of CRP during ongoing operation of a second apheresis column (4") in an apheresis device (II), comprising the following steps:

(A) beginning from the flow of blood plasma through the apheresis column (4"), introduction of the separated plasma via the plasma line (8A) into the apheresis column (4') and stopping the introduction of the separated plasma via the bypass line section (12') of the bypass line (12) into the apheresis column (4"), (B) introducing at least one regeneration solution via the at least one regeneration line (14) into the bypass line section (12') of the bypass line (12) or directly into the apheresis column (4"), wherein at least one regeneration solution is an alkali hydroxide solution, preferably a sodium hydroxide solution, (C) redirecting the liquid flow exiting the apheresis column (4") from the bypass line section (12") of the bypass line (12) to the waste line (13"), (D) starting the introduction of a neutralization solution via the at least one regeneration line (14) into the bypass line section (12') of the bypass line (12) or directly into the apheresis column (4"), (E) stopping the introduction of the neutralization solution, (F) introducing the separated plasma into the apheresis column (4") via the bypass line section (12') of the bypass line (12) and stopping the introduction of the separated plasma into the apheresis column (4') via the plasma line (8A)

(G) closing the waste line (13") and redirecting the liquid flow exiting the apheresis column (4') from the plasma line (8B) to the waste line (13').

A step (A) beginning from the flow of blood plasma through the apheresis column (4"), introduction of the separated plasma into the apheresis column (4') via the plasma line (8A) and directing of the CRP-depleted plasma into the venous line (6), thereby stopping the introduction of the separated plasma into the apheresis column (4") via the bypass line section (12') of the bypass line (12) is preferred.

A step (F) introduction of the separated plasma via the bypass line section (12') of the bypass line (12) into the apheresis column (4") and directing the CRP-depleted plasma into the venous line (6), thereby stopping the introduction of the separated plasma via the plasma line (8A) into apheresis column (4') is preferred.

Further, the present invention relates to a method for regeneration of two apheresis columns (4',4") for affinity chromatographic removal of CRP in an apheresis device (II), wherein the method enables regeneration during operation and is characterized by the following steps:

(A) beginning from the flow of blood plasma through the apheresis column (4"), starting the introduction of the separated plasma via the plasma line (8A) into the apheresis column (4') and stopping the introduction of the separated plasma via the bypass line section (12') of the bypass line (12) into the apheresis column (4"), (B) starting the introduction of a rinsing solution via the at least one regeneration line (14) into the bypass line section (12') of the bypass line (12) or directly into the apheresis column (4"), (C) starting the introduction of the liquid flow exiting the apheresis column (4") from the bypass line section (12") of the bypass line (12) into the waste line (13"), (D) stopping the introduction of the rinsing solution and transition to the introduction of the regeneration solution via the at least one regeneration line (14) into the bypass line section (12') of the bypass line (12) or directly into the apheresis column (4"), wherein the regeneration solution is an alkali hydroxide solution, preferably a sodium hydroxide solution, (E) stopping the introduction of the regeneration solution and transition to the introduction of the rinsing solution via the at least one regeneration line (14) into the bypass line section (12') of the bypass line (12) or directly into apheresis column (4"), (F) starting the introduction of the rinsing solution into the plasma line (8A) via the apheresis column (4') and thereby introduction of the separated plasma into apheresis column (4") via the bypass line section (12') of the bypass line (12), (G) closing the waste line (13"), (H) starting redirection of the liquid flow exiting apheresis column (4') from plasma line (8B) into waste line (13'), (I) stopping the introduction of the rinsing solution and transition to the introduction of a regeneration solution via the at least one regeneration line (14) into the plasma line (8A) or directly into the apheresis column (4').

(J) stopping the introduction of the regeneration solution and transition to the introduction of the rinsing solution via the at least one regeneration line (14) into the plasma line (8A) or directly into the apheresis column (4').

A step (A) beginning from the flow of blood plasma through the apheresis column (4"), starting the introduction of the separated plasma into the apheresis column (4') via the plasma line (8A) and directing the CRP-depleted plasma into the venous line (6), thereby stopping the introduction of the separated plasma into the apheresis column (4") via the bypass line section (12') of the bypass line (12) is preferred.

A step (G) closing the waste line (13") and forwarding the liquid flow exiting the apheresis column (4") into the venous line (6).

In the two aforementioned methods, a rinsing solution is used in addition to the regeneration solution. The rinsing solution is preferably physiologically acceptable and serves primarily to displace the blood plasma from the plasma line (8A) or the bypass line section (12') of the bypass line (12) from the point P2, from the apheresis column (4') or apheresis column (4") as well as from the bypass line section (12") of the bypass line (12) up to point P3 and the plasma line (8B) up to point P4. The rinsing solution serves less or not to regenerate the apheresis column (4') or the apheresis column (4"). With the rinsing solution plasma loss is therefore minimized or even completely prevented. Only when the blood plasma has been largely to completely displaced from the section of the apheresis device (II) to be flushed with regeneration solution, the regeneration solution is introduced to regenerate the apheresis column (4') or the apheresis column (4"). After regeneration has taken place, rinsing solution is then first fed again into the section of the apheresis device (II) that has been flushed with regeneration solution (i.e. in the direction of flow from point P2 through the apheresis column (4") to point P8) or through the apheresis column (4') to point P4) until the regeneration solution has been completely disposed through the waste lines (13', 13").

In this method, the rinsing solution is preferably a saline solution or a physiological saline solution or a PBS solution (phosphate buffered saline) or a combination of saline and PBS solution successively or simultaneously, and the regeneration solution is an alkali hydroxide solution, preferably a sodium hydroxide solution.

Further, the present invention relates to a method for regeneration of two apheresis columns (4',4") for affinity chromatographic removal of CRP in an apheresis device (II), wherein the method enables regeneration during operation and is characterized by the following steps:

(A) beginning from the flow of blood plasma through the apheresis column (4"), starting the introduction of the separated plasma into the apheresis column (4') via the plasma line (8A), and stopping the introduction of the separated plasma into the apheresis column (4") via the bypass line section (12') of the bypass line (12), (B) starting the introduction of a rinsing solution via the at least one regeneration line (14) into the bypass line section (12') of the bypass line (12) or directly into the apheresis column (4"), (C) starting the introduction of the liquid flow exiting the apheresis column (4") from the bypass line section (12") of the bypass line (12) into the waste line (13"), (D) stopping the introduction of the rinsing solution and transition to the introduction of the regeneration solution via the at least one regeneration line (14) into the bypass line section (12') of the bypass line (12) or directly into the apheresis column (4"), wherein the regeneration solution is an alkali hydroxide solution, preferably a sodium hydroxide solution, (E) stopping the introduction of the regeneration solution and transition to the introduction of the neutralization solution via the at least one regeneration line (14) into the bypass line section (12') of the bypass line (12) or directly into apheresis column (4"), (F) stopping the introduction of the neutralization solution and transition to the introduction of the neutralization solution via the at least one regeneration line (14) into the bypass line section (12') of the bypass line (12) or directly into apheresis column (4"), (G) starting the introduction of the rinsing solution into the plasma line (8A) via the apheresis column (4') and thus introduction of the separated plasma via the bypass line section (12') of the bypass line (12) into apheresis column (4"), (H) closing the waste line (13"), (I) starting the redirection of the liquid flow exiting from the apheresis column (4') from the plasma line (8B) into the waste line (13'), (I) stopping the introduction of the rinsing solution and transition to the introduction of a regeneration solution via the at least one regeneration line (14) into the plasma line (8A) or directly into the apheresis column (4').

(J) stopping the introduction of the regeneration solution and transition to the introduction of the rinsing solution via the at least one regeneration line (14) into the plasma line (8A) or directly into the apheresis column (4').

A step (A) beginning from the flow of blood plasma through the apheresis column (4"), starting the introduction of the separated plasma into the apheresis column (4') via the plasma line (8A) and directing the CRP-depleted plasma into the venous line (6), thereby stopping the introduction of the separated plasma into the apheresis column (4") via the bypass line section (12') of the bypass line (12) is preferred.

A step (H) closing the waste line (13") and forwarding the liquid flow exiting the apheresis column (4") into the venous line (6) is preferred.

In both of the aforementioned methods, steps (C) and (D) can be interchanged, i.e., can be performed in any order and also simultaneously, and can also be combined in one step. However, execution of step (D) before step (C) is preferred.

The preferred embodiment of the method according to the invention serves for efficient execution of the method without loss of blood plasma. Due to the simultaneous redirection of the separated plasma and the parallel introduction of the rinsing solution into the apheresis column (4"), there is no loss or no significant loss of blood plasma. Furthermore, an advantage of the preferred embodiment is that mixing of regeneration solution and blood plasma is completely avoided. This ensures that no regeneration solution enters the patient and, on the other hand, no loss of blood plasma occurs for the patient.

This is ensured by the sequential order of steps (B) to (E). Dilution of the blood plasma takes place, if at all, only through rinsing solution. On the other hand, mixing of blood plasma with regeneration solution is completely avoided.

The volume of rinsing solution according to step (B) preferably corresponds to 3 to 4 times the volume of the matrix of the apheresis column (4"). Minimally, the volume of rinsing solution according to step (B) corresponds to the volume of the bypass line section (12') of the bypass line (12) from point P2 to the apheresis column (4") plus the volume of the matrix of the apheresis column (4") and plus the volume of the bypass line section (12') of the bypass line (12) from the apheresis column (4") to point (P3).

The volume of rinsing solution according to step (F) preferably corresponds to 3 to 4 times the volume of the matrix of the apheresis column (4'). Minimally, the volume of rinsing solution according to step (B) corresponds to the volume of the plasma line (8A') from point (P2) to the apheresis column (4') plus the volume of the matrix of the apheresis column (4') and plus the volume of the plasma line (8B) from the apheresis column to point (P4).

The volume of regeneration solution according to step (D) is preferably 2 to 100 times the volume of the matrix of the apheresis column (4").

The volume of regeneration solution according to step (I) preferably corresponds to 2 to 100 times the volume of the matrix of the apheresis column (4').

The volume of rinsing solution according to step (E) preferably corresponds to 2 to 4 times the volume of the matrix of the apheresis column (4").

At least the volume of rinsing solution according to step (E) corresponds to the volume of the bypass line section (12') of the bypass line (12) from point P2 to the apheresis column (4") plus the volume of the matrix of the apheresis column (4") and plus the volume of the bypass line section (12') of the bypass line (12) from the apheresis column (4') to point P3.

The volume of rinsing solution according to step (J) preferably corresponds to 2 to 4 times the volume of the matrix of the apheresis column (4').

At least the volume of rinsing solution according to step (E) corresponds to the volume of the plasma line (8A) from point P2 to the apheresis column (4') plus the volume of the matrix of the apheresis column (4') and plus the volume of the plasma line (8B) from the apheresis column (4') to point P4.

In a preferred specific embodiment, the rinsing solution is a saline solution or a physiological saline solution or a PBS solution (phosphate buffered saline) or a combination of saline solution and PBS solution successively or simultaneously and the regeneration solution is an alkali hydroxide solution, preferably a sodium hydroxide solution.

Further, a preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) starting the redirection of the liquid flow exiting the apheresis column (4) from the plasma line (8B) to the waste line (13), (D) stopping the introduction of the saline solution and transition to the introduction of an alkali hydroxide solution, preferably a sodium hydroxide solution, via the at least one regeneration line (14) into the plasma line (8A) or directly into the apheresis column (4), (E) stopping the introduction of the alkali hydroxide solution, preferably the sodium hydroxide solution, and transition to the introduction of the saline solution via the at least one regeneration line (14) into the plasma line (8A) or directly into the apheresis column (4), (F) stopping the introduction of the saline solution and stopping the redirection of the separated plasma from the plasma line (8A) into the bypass line (12) and thereby direction of the separated plasma from the plasma line (8A) into the apheresis column (4);

(G) closing the waste line (13).

A step (G) closing the waste line (13) and forwarding the liquid flow exiting the apheresis column (4) into the venous line (6) is preferred.

Alternatively, the preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) stopping the introduction of the saline solution and transition to the introduction of an alkali hydroxide solution, preferably a sodium hydroxide solution, via the at least one regeneration line (14) into the plasma line (8A) or directly into the apheresis column (4), (D) starting the redirection of the liquid flow exiting the apheresis column (4) from the plasma line (8B) into the waste line (13), (E) stopping the introduction of the alkali hydroxide solution, preferably the sodium hydroxide solution, and transition to the introduction of the saline solution via the at least one regeneration line (14) into the plasma line (8A) or directly into the apheresis column (4), (F) closing the waste line (13);

(G) stopping the introduction of the saline solution and stopping the redirection of the separated plasma from the plasma line (8A) into the bypass line (12), thereby direction of the separated plasma from the plasma line (8A) into the apheresis column (4).

A step (F) closing the waste line (13) and forwarding the liquid flow exiting the apheresis column (4) into the venous line (6) is preferred.

Further, a preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) starting the redirection of the liquid flow exiting the apheresis column (4) from the plasma line (8B) to the waste line (13), (D) stopping the introduction of the saline solution and transition to the introduction of an alkali hydroxide solution preferably a sodium hydroxide solution via the at least one regeneration line (14) into the plasma line (8A) or directly into the apheresis column (4), (E) stopping the introduction of the alkali hydroxide solution, preferably the sodium hydroxide solution, and transition to the introduction of the citrate solution via the at least one regeneration line (14) into the plasma line (8A) or directly into the apheresis column (4), (F) stopping the introduction of the citrate solution and transition to the introduction of the saline solution via the at least one regeneration line (14) into the plasma line (8A) or directly into the apheresis column (4), (G) stopping the introduction of the saline solution and stopping the redirection of the separated plasma from the plasma line (8A) into the bypass line (12), and thereby direction of the separated plasma from the plasma line (8A) into the apheresis column (4);

(H) closing the waste line (13).

A step (H) closing the waste line (13) and forwarding the liquid flow exiting the apheresis column (4) into the venous line (6) is preferred.

Alternatively, the preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) stopping the introduction of the saline solution and transition to the introduction of an alkali hydroxide solution, preferably a sodium hydroxide solution, via the at least one regeneration line (14) into the plasma line (8A) or directly into the apheresis column (4), (D) starting the redirection of the liquid flow exiting the apheresis column (4) from the plasma line (8B) to the waste line (13), (E) stopping the introduction of the alkali hydroxide solution, preferably the sodium hydroxide solution, and transition to the introduction of the citrate solution via the at least one regeneration line (14) into the plasma line (8A) or directly into the apheresis column (4), (F) stopping the introduction of the citrate solution and transition to the introduction of the saline solution via the at least one regeneration line (14) into the plasma line (8A) or directly into the apheresis column (4), (G) closing the waste line (13);

(H) stopping the introduction of the saline and stopping the redirection of the separated plasma from the plasma line (8A) into the bypass line (12), and thereby direction of the separated plasma from the plasma line (8A) into the apheresis column (4).

A step (G) closing the waste line (13) and directing the liquid flow exiting the apheresis column (4) into the venous line (6) is preferred.

In the four aforementioned methods, steps (C) and (D) can be interchanged, i.e., can be performed in any order and also simultaneously, and can also be combined in one step.

Preferably, the regeneration methods according to the invention are carried out in such a way that first the plasma is displaced from the apheresis column (4) with a rinsing solution, such as a saline solution or physiological saline solution, and fed back into the patient to the point that almost only saline solution is fed back. Only then is the saline introduced into the waste line (13) and regeneration solution, such as an alkali hydroxide solution, preferably a sodium hydroxide solution, is introduced into the plasma line (8A) in the direction of flow after the bypass line (12), which displaces the saline, regenerates the apheresis column (4), is completely introduced into the waste line (13) and discarded. After the apheresis column (4) has been regenerated with several apheresis column volumes of regeneration solution, a rinsing solution, such as a saline solution or physiological saline solution, is again introduced until the regeneration solution is completely displaced from the apheresis device (1) and discarded. Only then is the waste line (13) closed, the rinsing solution returned to the patient, the bypass line (12) closed, and plasma reintroduced through the plasma line (8A) into the apheresis column (4) simultaneously or directly one after the other, wherein the order of the steps can be interchanged.

A further preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) starting the redirection of the liquid flow exiting the apheresis column (4) from the plasma line (8B) to the waste line (13), (D) stopping the introduction of the saline solution and transition to the introduction of an alkali hydroxide solution, preferably a sodium hydroxide solution, via the at least one regeneration line (14) into the plasma line (8A) or directly into the apheresis column (4), (E1) stopping the introduction of the alkali hydroxide solution, preferably the sodium hydroxide solution, and transition to the introduction of the saline solution via the at least one regeneration line (14) into the plasma line (8A) or directly into the apheresis column (4), (E2) stopping the introduction of the saline solution and transition to the introduction of a PBS solution via the at least one regeneration line (14) into the plasma line (8A) or directly into the apheresis column (4), (E3) stopping the introduction of the PBS solution and transition to the introduction of a saline solution via the at least one regeneration line (14) into the plasma line (8A) or directly into the apheresis column (4), (F) stopping the introduction of the saline solution and stopping the redirection of the separated plasma from the plasma line (8A) into the bypass line (12), and thereby direction of the separated plasma from the plasma line (8A) into the apheresis column (4);

(G) closing the waste line (13).

A step (G) closing the waste line (13) and forwarding the liquid flow exiting the apheresis column (4) into the venous line (6) is preferred.

An alternative preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) stopping the introduction of the saline solution and transition to the introduction of an alkali hydroxide solution, preferably a sodium hydroxide solution, via the at least one regeneration line (14) into the plasma line (8A) or directly into the apheresis column (4), (D) starting the redirection of the liquid flow exiting the apheresis column (4) from the plasma line (8B) to the waste line (13), (E1) stopping the introduction of the alkali hydroxide solution, preferably the sodium hydroxide solution, and transition to the introduction of the saline solution via the at least one regeneration line (14) into the plasma line (8A) or directly into the apheresis column (4), (E2) stopping the introduction of the saline solution and transition to the introduction of a PBS solution via the at least one regeneration line (14) into the plasma line (8A) or directly into the apheresis column (4), (E3) stopping the introduction of the PBS solution and transition to the introduction of a saline solution via the at least one regeneration line (14) into the plasma line (8A) or directly into the apheresis column (4), (F) closing the waste line (13);

(G) stopping the introduction of the saline solution and stopping the redirection of the separated plasma from the plasma line (8A) into the bypass line (12), and thereby direction of the separated plasma from the plasma line (8A) into the apheresis column (4).

A step (F) closing the waste line (13) and forwarding the liquid flow exiting the apheresis column (4) into the venous line (6) is preferred.

Another preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) starting the redirection of the liquid flow exiting the apheresis column (4) from the plasma line (8B) to the waste line (13), (D) stopping the introduction of the saline solution and transition to the introduction of an alkali hydroxide solution, preferably a sodium hydroxide solution, via the at least one regeneration line (14) into the plasma line (8A) or directly into the apheresis column (4), (E1) stopping the introduction of the alkali hydroxide solution, preferably the sodium hydroxide solution, and transition to the introduction of a citrate solution via the at least one regeneration line (14) into the plasma line (8A) or directly into the apheresis column (4), (E2) stopping the introduction of the citrate solution and transition to the introduction of a saline solution via the at least one regeneration line (14) into the plasma line (8A) or directly into the apheresis column (4), (E3) stopping the introduction of the saline solution and transition to the introduction of a PBS solution via the at least one regeneration line (14) into the plasma line (8A) or directly into the apheresis column (4), (E4) stopping the introduction of the PBS solution and transition to the introduction of a saline solution via the at least one regeneration line (14) into the plasma line (8A) or directly into the apheresis column (4), (F) stopping the introduction of saline and stopping the redirection of the separated plasma from the plasma line (8A) into the bypass line (12), and thereby direction of the separated plasma from the plasma line (8A) into the apheresis column (4);

(G) closing the waste line (13).

A step (G) closing the waste line (13) and forwarding the liquid flow exiting the apheresis column (4) into the venous line (6) is preferred.

An alternative preferred specific embodiment relates to a method for regeneration of an apheresis column (4) for affinity chromatographic removal of CRP in an apheresis device (1), wherein the method is characterized by the following steps:

(A) starting the redirection of the separated plasma from the plasma line (8A) into the bypass line (12), thereby stopping the direction of the separated plasma from the plasma line (8A) into the apheresis column (4), (B) starting the introduction of a saline solution via the at least one regeneration line (14) into the plasma line (8A) or directly into the apheresis column (4), (C) stopping the introduction of the saline solution and transition to the introduction of an alkali hydroxide solution, preferably a sodium hydroxide solution, via the at least one regeneration line (14) into the plasma line (8A) or directly into the apheresis column (4), (D) starting the redirection of the liquid flow exiting the apheresis column (4) from the plasma line (8B) to the waste line (13), (E1) stopping the introduction of the alkali hydroxide solution, preferably the sodium hydroxide solution and transition to the introduction of a citrate solution via the at least one regeneration line (14) into the plasma line (8A) or directly into the apheresis column (4), (E2) stopping the introduction of the citrate solution and transition to the introduction of a saline solution via the at least one regeneration line (14) into the plasma line (8A) or directly into the apheresis column (4), (E3) stopping the introduction of the saline solution and transition to the introduction of a PBS solution via the at least one regeneration line (14) into the plasma line (8A) or directly into the apheresis column (4), (E4) stopping the introduction of the PBS solution and transition to the introduction of a saline solution via the at least one regeneration line (14) into the plasma line (8A) or directly into the apheresis column (4), (F) closing the waste line (13);

(G) stopping the introduction of saline solution and stopping the redirection of the separated plasma from the plasma line (8A) into the bypass line (12), and thereby direction of the separated plasma from the plasma line (8A) into the apheresis column (4).

A step (F) closing the waste line (13) and forwarding the liquid flow exiting the apheresis column (4) into the venous line (6) is preferred.

In the four aforementioned methods, steps (C) and (D) are interchangeable, i.e., they can be performed in any order and also simultaneously, and they can also be combined in one step.

Thus, the present invention relates to a method for regeneration of two apheresis columns (4',4") for affinity chromatographic removal of CRP in an apheresis device (II), wherein the method enables regeneration during operation and is characterized by the following steps:

(A) beginning from the flow of blood plasma through the apheresis column (4"), starting the introduction of the separated plasma into the apheresis column (4') via the plasma line (8A), and stopping the introduction of the separated plasma into the apheresis column (4") via the bypass line section (12') of the bypass line (12), (B) starting the introduction of a saline solution via the at least one regeneration line (14) into the bypass line section (12') of the bypass line (12) or directly into the apheresis column (4"), (C) starting the introduction of the liquid flow exiting the apheresis column (4") from the bypass line section (12") of the bypass line (12) into the waste line (13"), (D) stopping the introduction of the saline solution and transition to the introduction of the alkali hydroxide solution, preferably the sodium hydroxide solution, via the at least one regeneration line (14) into the bypass line section (12') of the bypass line (12) or directly into the apheresis column (4"), (E) stopping the introduction of the alkali hydroxide solution, preferably the sodium hydroxide solution, and transition to the introduction of the saline solution via the at least one regeneration line (14) into the bypass line section (12') of the bypass line (12) or directly into apheresis column (4"), (F) starting the introduction of the saline solution into the plasma line (8A) via the apheresis column (4') and thereby introduction of the separated plasma into the apheresis column (4") via the bypass line section (12') of the bypass line (12), (G) closing the waste line (13"), (H) starting the redirection of the liquid flow exiting the apheresis column (4') from the plasma line (8B) into the waste line (13'), (I) stopping the introduction of the rinsing solution and transition to the introduction of an alkali hydroxide solution, preferably a sodium hydroxide solution, via the at least one regeneration line (14) into the plasma line (8A) or directly into the apheresis column (4'), (J) stopping the introduction of the alkali hydroxide solution, preferably the sodium hydroxide solution, and transition to the introduction of the saline solution via the at least one regeneration line (14) into the plasma line (8A) or directly into the apheresis column (4').

A step (A) beginning from the flow of blood plasma through the apheresis column (4"), starting the introduction of the separated plasma into the apheresis column (4') via the plasma line (8A) and directing the CRP-depleted plasma into venous line (6), thereby stopping the introduction of the separated plasma into the apheresis column (4") via the bypass line section (12') of the bypass line (12) is preferred.

A step (G) closing the waste line (13") and forwarding the liquid flow exiting the apheresis column (4") into the venous line (6) is preferred.

Thus, the present invention relates to a method for regeneration of two apheresis columns (4',4") for affinity chromatographic removal of CRP in an apheresis device (II), wherein the method enables regeneration during operation and is characterized by the following steps:

(A) beginning from the flow of blood plasma through the apheresis column (4"), starting the introduction of the separated plasma into the apheresis column (4') via the plasma line (8A), and stopping the introduction of the separated plasma into the apheresis column (4") via the bypass line section (12') of the bypass line (12), (B) starting the introduction of a saline solution via the at least one regeneration line (14) into the bypass line section (12') of the bypass line (12) or directly into the apheresis column (4"), (C) starting the introduction of the liquid flow exiting the apheresis column (4") from the bypass line section (12") of the bypass line (12) into the waste line (13"), (D) stopping the introduction of the saline solution and transition to the introduction of the alkali hydroxide solution, preferably the sodium hydroxide solution, via the at least one regeneration line (14) into the bypass line section (12') of the bypass line (12) or directly into the apheresis column (4"), (E) stopping the introduction of the alkali hydroxide solution, preferably the sodium hydroxide solution, and transition to the introduction of the saline solution via the at least one regeneration line (14) into the bypass line section (12') of the bypass line (12) or directly into apheresis column (4"), (F) starting the introduction of the saline solution into the plasma line (8A) via the apheresis column (4') and thereby introduction of the separated plasma into the apheresis column (4") via the bypass line section (12') of the bypass line (12), (G) closing the waste line (13"), (H) starting the redirection of the liquid flow exiting the apheresis column (4') from the plasma line (8B) into the waste line (13'), (I) stopping the introduction of the rinsing solution and transition to the introduction of an alkali hydroxide solution, preferably a sodium hydroxide solution, via the at least one regeneration line (13) into the plasma line (8A) or directly into the apheresis column (4'), (J) stopping the introduction of the alkali hydroxide solution, preferably the sodium hydroxide solution, and transition to the introduction of a citrate solution via the at least one regeneration line (14) into the plasma line (8A) or directly into the apheresis column (4'), (K) stopping the introduction of the citrate solution and transition to the introduction of the saline solution via the at least one regeneration line (14) into the plasma line (8A) or directly into the apheresis column (4').

A step (A) beginning from the flow of blood plasma through the apheresis column (4"), starting the introduction of the separated plasma into the apheresis column (4') via the plasma line (8A) and directing the CRP-depleted plasma into the venous line (6), thereby stopping the introduction of the separated plasma into the apheresis column (4") via the bypass line section (12') of the bypass line (12) is preferred.

A step (G) closing the waste line (13") and forwarding the liquid flow exiting the apheresis column (4") into the venous line (6) is preferred.

Preferably, the regeneration methods according to the invention are carried out in such a way that first the plasma is displaced from the apheresis column (4") with a rinsing solution, such as a saline solution or physiological saline solution, up to the point that almost only saline solution is passed through. Only then is preferably the saline solution directed into the waste line (13") and regeneration solution, such as an alkali hydroxide solution, preferably a sodium hydroxide solution, is introduced into the bypass line section (12') of the bypass line (12) in the direction of flow at the point P2, which displaces the saline solution, regenerates the apheresis column (4"), is completely introduced into the waste line (13") and discarded. After the apheresis column (4") has been regenerated with several apheresis column volumes of regeneration solution, a rinsing solution, such as a saline solution or physiological saline solution, is again introduced until the regeneration solution is completely displaced from the apheresis device (II) and discarded. Only then is the plasma line (8A) closed, the rinsing solution returned to the patient, and plasma reintroduced through the bypass line section (12') of the bypass line (12) into the apheresis column (4") simultaneously or directly one after the other.

A further preferred specific embodiment relates to a method for regeneration of two apheresis columns (4',4") for affinity chromatographic removal of CRP in an apheresis device (II), wherein the method enables regeneration during operation and is characterized by the following steps:

(A) beginning from the flow of blood plasma through the apheresis column (4"), starting the introduction of the separated plasma into the apheresis column (4') via the plasma line (8A), and stopping the introduction of the separated plasma into the apheresis column (4") via the bypass line section (12') of the bypass line (12), (B) starting the introduction of a saline solution via the at least one regeneration line (14) into the bypass line section (12') of the bypass line (12) or directly into the apheresis column (4"), (C) starting the introduction of the liquid flow exiting the apheresis column (4") from the bypass line section (12') of the bypass line (12) into the waste line (13"), (D) stopping the introduction of the saline solution and transition to the introduction of the alkali hydroxide solution, preferably the sodium hydroxide solution, via the at least one regeneration line (14) into the bypass line section (12') of the bypass line (12) or directly into the apheresis column (4"), (E1) stopping the introduction of the alkali hydroxide solution, preferably the sodium hydroxide solution, and transition to the introduction of the saline solution via the at least one regeneration line (14) into the bypass line section (12') of the bypass line (12) or directly into apheresis column (4"), (E2) stopping the introduction of the saline solution and transition to the introduction of a PBS solution via the at least one regeneration line (14) into the bypass line section (12') of the bypass line (12) or directly into the apheresis column (4"), (E3) stopping the introduction of the PBS solution and transition to the introduction of a saline solution via the at least one regeneration line (14) into the bypass line section (12') of the bypass line (12) or directly into the apheresis column (4"), (F) starting the introduction of the saline solution into the plasma line (8A) via the apheresis column (4') and thereby introduction of the separated plasma into the apheresis column (4") via the bypass line section (12') of the bypass line (12), (G) closing the waste line (13"), (H) starting the redirection of the liquid flow exiting the apheresis column (4') from the plasma line (8B) to the waste line (13'), (I) stopping the introduction of the rinsing solution and transition to the introduction of an alkali hydroxide solution, preferably a sodium hydroxide solution, via the at least one regeneration line (14) into the plasma line (8A) or directly into the apheresis column (4'), (J) stopping the introduction of the alkali hydroxide solution, preferably the sodium hydroxide solution, and transition to the introduction of the saline solution via the at least one regeneration line (14) into the plasma line (8A) or directly into the apheresis column (4').

A step (A) beginning from the flow of blood plasma through the apheresis column (4"), starting the introduction of the separated plasma into the apheresis column (4') via the plasma line (8A) and directing the CRP-depleted plasma into the venous line (6), thereby stopping the introduction of the separated plasma into the apheresis column (4") via the bypass line section (12') of the bypass line (12) is preferred.

A step (G) closing the waste line (13") and forwarding the liquid flow exiting the apheresis column (4") into the venous line (6) is preferred.

A further preferred specific embodiment relates to a method for regeneration of two apheresis columns (4',4") for affinity chromatographic removal of CRP in an apheresis device (II), wherein the method enables regeneration during operation and is characterized by the following steps:

(A) beginning from the flow of blood plasma through the apheresis column (4"), starting the introduction of the separated plasma into the apheresis column (4') via the plasma line (8A), and stopping the introduction of the separated plasma into the apheresis column (4") via the bypass line section (12') of the bypass line (12), (B) starting the introduction of a saline solution via the at least one regeneration line (14) into the bypass line section (12') of the bypass line (12) or directly into the apheresis column (4"), (C) starting the introduction of the liquid flow exiting the apheresis column (4") from the bypass line section (12') of the bypass line (12) into the waste line (13"), (D) stopping the introduction of the saline solution and transition to the introduction of the alkali hydroxide solution, preferably the sodium hydroxide solution, via the at least one regeneration line (14) into the bypass line section (12') of the bypass line (12) or directly into the apheresis column (4"), (E1) stopping the introduction of the alkali hydroxide solution, preferably the sodium hydroxide solution, and transition to the introduction of the saline solution via the at least one regeneration line (14) into the bypass line section (12') of the bypass line (12) or directly into apheresis column (4"), (E2) stopping the introduction of the saline solution and transition to the introduction of a PBS solution via the at least one regeneration line (14) into the bypass line section (12') of the bypass line (12) or directly into the apheresis column (4"), (E3) stopping the introduction of the PBS solution and transition to the introduction of a saline solution via the at least one regeneration line (14) into the bypass line section (12') of the bypass line (12) or directly into the apheresis column (4"), (F) starting the introduction of the saline solution into the plasma line (8A) via the apheresis column (4') and thereby introduction of the separated plasma into the apheresis column (4") via the bypass line section (12') of the bypass line (12), (G) closing the waste line (13"), (H) starting the redirection of the liquid flow exiting the apheresis column (4') from the plasma line (8B) into the waste line (13'), (I) stopping the introduction of the rinsing solution and transition to the introduction of an alkali hydroxide solution, preferably a sodium hydroxide solution, via the at least one regeneration line (14) into the plasma line (8A) or directly into the apheresis column (4'), (J) stopping the introduction of the alkali hydroxide solution, preferably the sodium hydroxide solution, and transition to the introduction of a citrate solution via the at least one regeneration line (14) into the plasma line (8A) or directly into the apheresis column (4'), (K) stopping the introduction of the citrate solution and transition to the introduction of the saline solution via the at least one regeneration line (14) into the plasma line (8A) or directly into the apheresis column (4').

A step (A) beginning from the flow of blood plasma through the apheresis column (4"), starting the introduction of the separated plasma into the apheresis column (4') via the plasma line (8A) and directing the CRP-depleted plasma into the venous line (6), thereby stopping the introduction of the separated plasma into the apheresis column (4") via the bypass line section (12') of the bypass line (12) is preferred.

A step (G) closing the waste line (13") and forwarding the liquid flow exiting the apheresis column (4") into the venous line (6) is preferred.

In all the above methods, the parts of the apheresis device into which the alkali hydroxide solution is introduced are resistant to the alkali hydroxide solution used, in particular the sodium hydroxide solution used.

EXAMPLES

Example of Use

The term "matrix volume" (also abbreviated as MV), as used herein, refers to the volume of the matrix contained within the adsorber.

The term "adsorber volume" (also abbreviated as AV), as used herein, refers to the volume of the adsorber housing.

Example 1: Apheresis with a Bypass Line and an Apheresis Column

Preparation:

A suitable tubing system is inserted into the apheresis device (1) for extracorporeal removal of CRP from blood of a patient according to FIG. 7, with a plasma centrifuge as cell separator (7). A 5 L bag of 0.9% NaCl solution and a 500 ml bag of ACD-A solution (Acid-Citrate-Dextrose solution) and/or a 2000 ml bag of 0.08 M sodium hydroxide solution and/or a 2000 ml bag of glycine/HCl and/or a 2000 ml bag of PBS solution are connected to the connection line or regeneration line. Two 3 L waste bags are connected to the waste line (13) (e.g., via a 3-way valve).

The arterial (5) and venous (6) lines are connected with an adapter. Likewise, the plasma lines (8A and 8B) before and after the adsorber are connected with an adapter (without adsorber in between) to form a closed system.

The entire system is filled with NaCl solution by pre-rinsing with 1 L 0.9% NaCl solution (200 ml/min); the air present is displaced into the first waste bag. A shaken CRP adsorber (MV 20 ml, AV 30 ml) is then inserted into the plasma line (8A and 8B) instead of the adapter. The adsorber is pre-rinsed with 1 L NaCl solution (100 ml/min). The NaCl is also directed into the first waste bag.

As the last step of the preparation, the plasma centrifuge is pre-filled with 0.9% NaCl solution and 1:15 diluted ACD-A solution. The required volume is composed of the volume of the tubing system in the plasma centrifuge (7), the connection line (11) up to the plasma centrifuge and the plasma line between the plasma centrifuge and P2. The displaced NaCl is directed into the first waste bag via P4/P6.

Apheresis:

1. After completed preparation, it is switched to the second waste bag. The patient is connected to the arterial (5) and venous (6) lines. At the start of apheresis, the blood is directed into the centrifuge (60-80 ml/min). Throughout the treatment, ACD-A is mixed into the blood at a ratio of 1:15 (1 ml ACD-A to 15 ml blood) via the connection line (11).

The NaCl thereby displaced is directed to the second waste bag via P2, the bypass line (12) and P4/P6. When plasma separation begins, after a volume corresponding to the tubing from the plasma centrifuge to point P4/6, the system switches so that the plasma flows into the venous line (6), and thus back to the patient. After a constant plasma flow of approximately 30 ml/min has been achieved for 3 minutes, the first cycle can begin.

2. The bypass line (12) is closed and the plasma is passed over the adsorber (loading). Thereby, the NaCl present in the plasma line (8A and 8B) and the adsorber is passed via P4/P6 into the second waste bag up to a volume consisting of the volume of the plasma line (8A and 8B) plus the AV. The adsorber is then loaded with 50-100 MV (1000 to 2000 ml) of plasma. Afterwards, regeneration begins.

3. Regeneration

Variant A—Glycine/HCl and PBS Solution

For this, the plasma is returned to the patient via the bypass line (12).

The adsorber is now rinsed with 0.9% NaCl (30 ml/min) via the regeneration line (14) and the plasma line (8A and 8B). The volume required for this is calculated from the AV and the volume of the plasma line (8A and 8B). The plasma in the plasma line (8A and 8B) and the adsorber is also returned to the patient up to a volume consisting of the AV and 75% of the volume of the plasma line (8A and 8B). Subsequently, P4/P6 is switched to direct the solutions into the second waste bag.

In the next step, it is regenerated with 3 MV (60 ml) 0.9% NaCl followed by 4 MV (80 ml) glycine/HCl (100 ml/min). This is followed by neutralization with 4 MV (80 ml) of PBS. Afterwards, it is rinsed with 0.9% NaCl (100 ml/min). The volume required for this is calculated from the AV, the volume of the regeneration line (14) and the plasma line (8A and 8B).

Then, step 2 (loading) can be performed again, followed by step 3.

Variant B—Sodium Hydroxide Solution and PBS Solution.

For this, the plasma is returned to the patient via the bypass line (12).

The adsorber is now rinsed with 0.9% NaCl (30 ml/min-40 ml/min) via the regeneration line (14) and the plasma line (8A and 8B). The volume required for this is calculated from the AV and the volume of the plasma line (8A and 8B). The plasma in the plasma line (8A and 8B) and the adsorber is also returned to the patient up to a volume consisting of the AV and 75% of the volume of the plasma line (8A and 8B). Subsequently, P4/P6 is switched to direct the solutions into the second waste bag.

In the next step, it is pre-rinsed with 3 MV (60 ml) 0.9% NaCl followed by regeneration with 5 MV 0.08 M NaOH (pH 12.6; flow rate of 80 ml/min). This is followed by neutralization with 6 MV of PBS solution. The PBS is then displaced with 4 MV 0.9% NaCl (flow rate of 80 ml/min).

Then, step 2 (loading) can be performed again, followed by step 3. If necessary, the bag with sodium hydroxide solution or PBS solution must be replaced, respectively.

Variant C—Sodium Hydroxide Solution and Citrate Solution.

For this, the plasma is returned to the patient via the bypass line (12).

The adsorber is now rinsed with 0.9% NaCl (30 ml/min-40 ml/min) via the regeneration line (14) and the plasma line (8A and 8B). The volume required for this is calculated from the AV and the volume of the plasma line (8A and 8B). The plasma in the plasma line (8A and 8B) and the adsorber is also returned to the patient up to a volume consisting of the AV and 75% of the volume of the plasma line (8A and 8B). Subsequently, P4/P6 is switched to direct the solutions into the second waste bag.

In the next step, it is pre-rinsed with 3 MV (60 ml) 0.9% NaCl and then regenerated with 5 MV 0.1 M NaOH (pH 12.9; flow rate of 80 ml/min). This is followed by neutralization with 4 MV 4% citrate solution (pH 7; flow rate of 80 ml/min). The citrate is then displaced with 3 MV 0.9% NaCl (flow rate of 80 ml/min).

Then, step 2 (loading) can be performed again, followed by step 3. If necessary, the bag with sodium hydroxide solution or citrate solution must be replaced, respectively.

Variant D—Sodium Hydroxide Solution and Sodium Chloride Solution.

For this, the plasma is returned to the patient via the bypass line (12).

The adsorber is now rinsed with 0.9% NaCl (30 ml/min-40 ml/min) via the regeneration line (14) and the plasma line (8A and 8B). The volume required for this is calculated from the AV and the volume of the plasma line (8A and 8B). The plasma in the plasma line (8A and 8B) and the adsorber is also returned to the patient up to a volume consisting of the AV and 75% of the volume of the plasma line (8A and 8B). Subsequently, P4/P6 is switched to direct the solutions into the second waste bag.

In the next step, it is pre-rinsed with 2 MV (60 ml) 0.9% NaCl and then regenerated with 5 MV 0.1 M NaOH (pH 12.9; flow rate of 80 ml/min). The sodium hydroxide is then displaced with 6 MV 0.9% NaCl (flow rate of 80 ml/min).

Then, step 2 (loading) can be performed again, followed by step 3. If necessary, the bag with sodium hydroxide solution must be replaced.

4. After the last loading, a final regeneration is performed. At the same time, the arterial line (5) is closed. Using 0.9% NaCl (30 ml/min), the blood from the plasma centrifuge (7) is displaced via the cell line (9) as well as the remaining plasma from the plasma line to P2 and the bypass line (12) and returned to the patient. The volume required for this is composed of the volume of the plasma centrifuge (7), the volume of the plasma line up to P2, bypass line (12), the cell line (9) and the arterial line (6). The patient can then be separated from the apheresis device.

Variant E—Potassium Hydroxide Solution and PBS Solution

Experimental procedure as for variant B. After rinsing with NaCl solution, it is regenerated with 5 MV 0.08 M KOH (pH 13.2; flow rate of 80 ml/min).

Variant F—Potassium Hydroxide Solution and Citrate Solution

Experimental procedure as for variant C. After rinsing with NaCl solution, it is regenerated with 5 MV 0.1 M KOH (pH 13.4; flow rate of 80 ml/min).

Variant G—Potassium Hydroxide Solution and Sodium Chloride Solution

Experimental procedure as for variant D. After rinsing with NaCl solution, it is regenerated with 5 MV 0.1 M KOH (pH 13.3; flow rate of 80 ml/min).

Variant H—Lithium Hydroxide Solution and PBS Solution

Experimental procedure as for variant B. After rinsing with NaCl solution, it is regenerated with 5 MV 0.08 M LiOH (pH 13.3; flow rate of 80 ml/min).

Variant I—Lithium Hydroxide Solution and Citrate Solution

Experimental procedure as for variant C. After rinsing with NaCl solution, it is regenerated with 5 MV 0.1 M LiOH (pH 13.5; flow rate of 80 ml/min).

Variant J—Lithium Hydroxide Solution and Sodium Chloride Solution

Experimental procedure as for variant D. After rinsing with NaCl solution, it is regenerated with 5 MV 0.1 M LiOH (pH 13.5; flow rate of 80 ml/min).

5. Preservation

Variant A

If desired, the NaCl bag can now be replaced with a bag with preservation solution (e.g. PBS with Na-azide). The adsorber is rinsed with 10 MV preservation solution via the regeneration line (into the second waste bag). The adsorber is then removed, sealed and stored. The tubing system is removed from the apheresis device and is disposed.

Variant B

The adsorber is rinsed with 10 MV sodium hydroxide solution as the preservation solution via the regeneration line (into the second waste bag). The adsorber is then removed, sealed and stored. The tubing system is removed from the apheresis device and is disposed.

Results:

For the regeneration according to variant A with glycine/HCl solution, the formation of a protein layer around the matrix particles (agarose particles) was observed. This is probably due to acidic protein precipitation because of the very low pH of pH 2-3. If the patient's blood to be purified contained a high concentration of cell-free DNA/RNA, this led to an enhancement of the effect. It has been shown that the formation of the protein layer in the apheresis column masks binding sites and reduces the performance of the apheresis material. The original state could not be restored by known measures such as further regeneration attempts with a glycine/HCl solution. As the damage to the apheresis column progresses, the treatment time for the patient increases, and so does the suffering time of the patient. In addition, the damaged apheresis columns were often no longer usable for further use, so that the treatment costs increased considerably. Furthermore, the protein layer or protein-DNA as well as protein-RNA layer can cause clogging of the fine pores, which increases the system pressure while the flow rate remains constant. A further increase in the flow rate is accompanied by a further increase in pressure. This may lead to discontinuation of the treatment. These apheresis columns were also no longer suitable for further use.

For the regeneration according to variants B, C, D, E, F, G, H, I, and J with sodium hydroxide solution, potassium hydroxide solution and lithium hydroxide solution, respectively, it has been found that, on the one hand, a basic regeneration with the alkali hydroxide solution can also regenerate an already damaged adsorber matrix. Surprisingly, it could been shown that when only an alkali hydroxide solution is used for regeneration and preferably only a sodium hydroxide solution is used as regeneration agent, no acidic protein precipitation occurs and thus the disadvantages of regeneration with glycine/HCl solution described above do not occur. PBS solution (variant B), citrate solution (variant C) or sodium chloride solution (variant D) were used as neutralization solution. The advantages of using a citrate solution over a PBS solution are the reduced neutralization time and the reduced rinsing volume required.

Example 2: Alternating Use of the Apheresis Column Connected in Parallel

Preparation:

A suitable tubing system is inserted into the apheresis device (II) for extracorporeal removal of CRP from blood of a patient as shown in FIG. 13, with a plasma centrifuge as cell separator (7). A 5 L bag of 0.9% NaCl solution and a 500 ml bag of ACD-A solution are connected to the connection line. Two 3 L waste bags are connected to the waste line (13) (e.g. via a 3-way valve).

The arterial (5) and venous (6) lines are connected with an adapter. Similarly, the plasma lines (8A and 8B) before and after the adsorber are connected with an adapter (without adsorber in between), and the bypass line sections (12' and 12") of the bypass line (12) before and after the adsorber are connected with an adapter (without adsorber in between) to form a closed system.

The entire system is filled with NaCl solution by prerinsing with 1 L 0.9% NaCl solution (200 ml/min); the air present is displaced into the first waste bag. A shaken CRP adsorber (MV 20 ml, AV 30 ml) is then inserted into the bypass line sections (12' and 12") and into the plasma line (8A and 8B) instead of the adapter. The adsorber is prerinsed with 1 L NaCl solution (100 ml/min). The NaCl is also directed into the first waste bag.

As the last step of the preparation, the plasma centrifuge is pre-filled with 0.9% NaCl solution and 1:15 diluted ACD-A solution. The required volume is composed of the volume of the tubing system in the plasma centrifuge (7), the connection line (11) up to the plasma centrifuge and the plasma line between the plasma centrifuge and P2. The displaced sodium chloride is fed into the first waste bag via P8/P4/P6.

Apheresis:

1. After completed preparation, it is switched over to the second waste bag. The patient is connected to the arterial (5) and venous (6) lines. At the start of apheresis, the blood is directed into the centrifuge (60-80 ml/min). Throughout the treatment, ACD-A is mixed into the blood at a ratio of 1:15 (1 ml ACD-A to 15 ml blood) via the connection line (11). The NaCl thereby displaced is directed to the second waste bag via P2, the bypass line section 12' and P8/P4/P6. When plasma separation begins, after a volume corresponding to the tubing from the plasma centrifuge to the P8/P4/P6 point, the system switches so that the plasma flows back into the venous line (6), and thus to the patient. After a constant plasma flow of approx. 30 ml/min has been achieved for 3 minutes, the first cycle can begin.

2. The plasma line (8A) in the region between the nodal point (P2) and the adsorber (4') is closed and the plasma is passed through the adsorber (4") (loading). Thereby, the NaCl present in the bypass line sections (12' and 12") and the adsorber (4") is directed into the second waste bag via P3/P4/P6 up to a volume consisting of the volume of the bypass line sections (12' and 12") plus the AV. The adsorber (4") is then loaded with 50-100 MV (1000 to 2000 ml) of plasma. The blood plasma is then displaced from the adsorber (4") with the sodium chloride solution.

3. It is switched over to the second adsorber and the bypass line section (12') is closed in the region between the nodal point (P2) and the adsorber (4"). The plasma is directed over the adsorber (4') (loading). Thereby, the sodium chloride solution present in the bypass line sections (12' and 12") and the adsorber (4') is directed into the second waste bag via P8/P4/P6 up to a volume consisting of the volume of the plasma line (8A and 8B) plus the AV. The adsorber (4') is then loaded with 50-100 MV (1000 to 2000 ml) of plasma. The blood plasma is then displaced from the adsorber (4') with the sodium chloride solution and fed to the patient.

4. While adsorber (4') is loaded with plasma, adsorber (4") is simultaneously regenerated according to a method according to example 1 (variant A, B, C, D). If adsorber (4") is loaded, adsorber (4') can be regenerated.

5. After the last loading, a final regeneration is performed. At the same time, the arterial line (5) is closed. Via the connection line (11), the blood is displaced from the plasma centrifuge (7) via the cell line (9) using 0.9% NaCl (30 ml/min) and returned to the patient. The volume required for this is composed of the volume of the plasma centrifuge (7) and the volume of the cell line (9) and the arterial line (6). The patient can then be separated from the apheresis device.

For the regeneration according to variant A with glycine/HCl solution, protein deposits were observed on the adsorber matrix, which could not be dissolved or removed from the adsorber matrix even after a longer regeneration phase with glycine/HCl solution.

Such protein deposits were not observed for the regenerations according to variants B, C and D, and the regenerated adsorbers according to variants B, C and D showed a higher CRP loading capacity after regeneration than the adsorbers according to variant A.

Regeneration of an Adsorber Regenerated with Glycine/HCl Solution Using NaOH Solution The adsorber regenerated according to variant A with glycine/HCl solution, which had noticeable protein deposits on the adsorber, was regenerated according to variant B using a sodium hydroxide solution. Surprisingly, it was found that the protein deposits present could be removed again by rinsing with sodium hydroxide solution of a concentration of 0.1 mol/l.

Thus, an alkali hydroxide solution can also be used to regenerate adsorbers in which protein deposits are already present.

6. Preservation

Variant A

If desired, the sodium chloride solution bag can now be replaced with a bag with preservation solution (e.g. PBS with Na-azide). The adsorber is rinsed with 10 MV preservation solution via the regeneration line (into the second waste bag). The adsorber is then removed, sealed and stored. The tubing system is removed from the apheresis device and is disposed.

Variant B

The adsorber is rinsed with 10 MV sodium hydroxide solution as preservation solution via the regeneration line (into the second waste bag). The adsorber is then removed, sealed and stored. The tubing system is removed from the apheresis device and is disposed.

Example 3: Alternating Use of Apheresis Columns Connected in Parallel (4', 4") and Regeneration During Operation Preparation:

A suitable tubing system is inserted into the apheresis device (II) for extracorporeal removal of CRP from blood of a patient as shown in FIG. 16, with a plasma centrifuge as cell separator (7). A 5 L bag of 0.9% NaCl solution and a 500 ml bag of ACD-A solution (Acid-Citrate-Dextrose solution)

and/or a 2000 ml bag of 0.08 M sodium hydroxide solution and/or a 2000 ml bag of glycine/HCl and/or a 2000 ml bag of PBS solution are connected to the connection line or regeneration line. Two 3 L waste bags are connected to the waste line (13) (e.g., via a 3-way valve).

The arterial (5) and venous (6) lines are connected with an adapter. Similarly, the bypass line sections (12' and 12") before and after the adsorber are connected with an adapter (without adsorber in between) and the plasma lines (8A and 8B) before and after the adsorber are connected with an adapter (without adsorber in between) to form a closed system.

The entire system is filled with NaCl solution by pre-rinsing with 1 L of 0.9% NaCl solution (200 ml/min); the air present is displaced into the first waste bag. A shaken CRP adsorber (MV 20 ml, AV 30 ml) is then inserted into the bypass line sections (12' and 12") and into the plasma line (8A and 8B) instead of the adapter. The adsorber is pre-rinsed with 1 L NaCl solution (100 ml/min). The NaCl is also directed into the first waste bag.

As the last step of the preparation, the plasma centrifuge is pre-filled with 0.9% NaCl solution and 1:15 diluted ACD-A solution. The required volume is composed of the volume of the tubing system in the plasma centrifuge (7), the connection line (11) up to the plasma centrifuge and the plasma line between the plasma centrifuge and P2. The displaced sodium chloride is directed into the first waste bag via P8/P4/P6.

Apheresis:

1. After completed preparation, it is switched to the second waste bag. The patient is connected to the arterial (5) and venous (6) lines. At the start of apheresis, the blood is directed into the centrifuge (60-80 ml/min). Throughout the treatment, ACD-A is mixed into the blood at a ratio of 1:15 (1 ml ACD-A to 15 ml blood) via the connection line (11).

The NaCl thus displaced is directed to the second waste bag via P2, the bypass line section (12') and P8/P4/P6. When plasma separation begins, after a volume corresponding to the tubing from the plasma centrifuge to the P8/P4/6 point, it is switched so that plasma flows into the venous line (6), and thus back to the patient. After a constant plasma flow of approx. 30 ml/min has been achieved for 3 minutes, the first cycle can begin.

2. The plasma line (8A) is closed and the plasma is directed over the adsorber (4") (loading). In this process, the NaCl present in the bypass line sections (12' and 12") and the adsorber (4") is directed into the second waste bag via P8/P4/P6 up to a volume consisting of the volume of the bypass line sections (12' and 12") plus the AV. The adsorber is then loaded with 50-100 MV (1000 to 2000 ml) of plasma. The blood plasma is then displaced from the adsorber (4") with the sodium chloride solution.

3. It is switched to the second adsorber and the bypass line section (12') is closed into the region between the nodal point (P2) and the adsorber (4"). The plasma is directed over the adsorber (4') (loading). In this process, the sodium chloride solution present in the bypass line sections (12' and 12") and the adsorber (4") is directed into the second waste bag via P8/P4/P6 up to a volume consisting of the volume of the plasma line (8A and 8B) plus the AV. The adsorber (4') is then loaded with 50-100 MV (1000 to 2000 ml) of plasma. The blood plasma is then displaced from the adsorber (4') with the sodium chloride solution and fed to the patient.

Regeneration

Variant A—Glycine/HCl and PBS Solution

At the same time, the adsorber (4") is now rinsed (30 ml/min) with 0.9% NaCl via the regeneration line (14) and the bypass line sections (12' and 12"). The volume required for this is calculated from the AV and the volume of the bypass line sections (12' and 12"). The plasma present in the bypass line sections (12' and 12") and the adsorber (4") is also returned to the patient up to a volume consisting of the AV and 75% of the volume of the plasma line (8A and 8B). Subsequently, P4/P6 is switched to direct the solutions into the second waste bag.

In the next step, it is to regenerated with 3 MV (60 ml) 0.9% NaCl followed by 4 MV (80 ml) glycine/HCl (100 ml/min). Subsequently, it is neutralized with 5 MV PBS. Afterwards, it is rinsed with 0.9% NaCl (100 ml/min). The volume required for this is calculated from the AV, the volume of the regeneration line (14) and the plasma line (8A and 8B).

Step 2 (loading) can then be carried out again, followed by step 3.

Variant B—Sodium Hydroxide Solution and PBS Solution

At the same time, the adsorber (4") is now rinsed with 0.9% NaCl (30 ml/min-40 ml/min) via the regeneration line (14) and the bypass line sections (12' and 12"). The volume required for this is calculated from the AV and the volume of the bypass line sections (12' and 12"). The plasma contained in the bypass line sections (12' and 12") and the adsorber is also returned to the patient up to a volume consisting of the AV and 75% of the volume of the plasma line (8A and 8B). Subsequently, P4/P6 is switched to direct the solutions into the second waste bag.

In the next step, it is pre-rinsed with 3 MV (60 ml) 0.9% NaCl and then regenerated with 5 MV 0.08M NaOH (pH 12.6; flow rate of 80 ml/min). This is followed by neutralization with 6 MV PBS solution (pH 12.6; flow rate of 80 ml/min). The PBS is then displaced with 4 MV 0.9% NaCl (flow rate of 80 ml/min).

Step 2 (loading) can then be carried out again, followed by step 3. If necessary, the bag with sodium hydroxide solution or PBS solution must be replaced, respectively.

Variant C—Sodium Hydroxide Solution and Citrate Solution

At the same time, the adsorber (4") is now rinsed with 0.9% NaCl (30 ml/min-40 ml/min) via the regeneration line (14) and the bypass line sections (12' and 12"). The volume required for this is calculated from the AV and the volume of the bypass line sections (12' and 12"). The plasma contained in the bypass line sections (12' and 12") and the adsorber is also returned to the patient up to a volume consisting of the AV and 75% of the volume of the plasma line (8A and 8B). Subsequently, P4/P6 is switched to direct the solutions into the second waste bag.

In the next step, it is pre-rinsed with 3 MV (60 ml) 0.9% NaCl and then regenerated with 5 MV 0.1 M NaOH (pH 12.9; flow rate of 80 ml/min). This is followed by neutralization with 4 MV 4% citrate solution (pH 7; flow rate of 80 ml/min). The citrate is then displaced with 3 MV 0.9% NaCl (flow rate of 80 ml/min).

Step 2 (loading) can then be carried out again, followed by step 3. If necessary, the bag with sodium hydroxide solution or citrate solution must be replaced, respectively.

Variant D—Sodium Hydroxide Solution and NaCl Solution

At the same time, the adsorber (4") is now rinsed with 0.9% NaCl (30 ml/min-40 ml/min) via the regeneration line (14) and the bypass line sections (12' and 12"). The volume required for this is calculated from the AV and the volume of the bypass line sections (12' and 12"). The plasma contained in the bypass line sections (12' and 12") and the adsorber is also returned to the patient up to a volume consisting of the AV and 75% of the volume of the plasma line (8A and 8B). Subsequently, P4/P6 is switched to direct the solutions into the second waste bag.

In the next step, it is pre-rinsed with 2 MV (60 ml) 0.9% NaCl and then regenerated with 5 MV 0.1 M NaOH (pH 12.9; flow rate of 80 ml/min). The sodium hydroxide is then displaced with 6 MV 0.9% NaCl (flow rate of 80 ml/min).

Step 2 (loading) can then be performed again, followed by step 3. If necessary, the bag with sodium hydroxide solution must be replaced.

4. After the last loading, a final regeneration is performed. At the same time, the arterial line (5) is closed. Via the connection line (11), the blood is displaced from the plasma centrifuge (7) via the cell line (9) using 0.9% NaCl (30 ml/min) and returned to the patient. The volume required for this is composed of the volume of the plasma centrifuge (7) and the volume of the cell line (9) and the arterial line (6). The patient can then be separated from the apheresis device.

5. Preservation

Variant A

If desired, the sodium chloride solution bag can now be replaced by a bag with preservation solution (e.g. PBS with Na-azide). The adsorber is rinsed with 10 MV preservation solution via the regeneration line (into the second waste bag). The adsorber is then removed, sealed and stored. The tubing system is removed from the apheresis device and is disposed.

Variant B

The adsorber is rinsed with 10 MV sodium hydroxide solution as preservation solution via the regeneration line (into the second waste bag). The adsorber is then removed, sealed and stored. The tubing system is removed from the apheresis device and is disposed.

Results:

For the regeneration according to variant A with glycine/HCl solution, the formation of a protein layer around the matrix particles (agarose particles) was observed. This is probably due to acidic protein precipitation because of the very low pH of pH 2-3. If the patient's blood to be purified contained a high concentration of cell-free DNA/RNA, this led to an enhancement of the effect. The formation of the protein layer in the apheresis column was shown to mask binding sites and reduce the performance of the apheresis material. The original state could not be restored by known measures such as further regeneration attempts with a glycine/HCl solution. As the damage to the apheresis column progresses, the treatment time for the patient increases, and so does the suffering time of the patient. In addition, the damaged apheresis columns were often no longer usable for further use, so that the treatment costs increased considerably. Furthermore, the protein layer or protein-DNA as well as protein-RNA layer can cause clogging of the fine pores, which increases the system pressure while the flow rate remains constant. A further increase in the flow rate is accompanied by a further increase in pressure. This may lead to discontinuation of the treatment. These apheresis columns were also no longer suitable for further use.

For the regeneration according to variants B, C and D with sodium hydroxide solution, it could be shown that, on the one hand, basic regeneration with sodium hydroxide solution can also regenerate an already damaged adsorber matrix. Surprisingly, it could be shown that when only sodium hydroxide solution is used as the regeneration agent, no acidic protein precipitation occurs and thus the disadvantages of regeneration with glycine/HCl solution described above do not occur. PBS solution (variant B), citrate solution (variant C) or sodium chloride solution (variant D) were used as neutralization solution. The advantages of using a citrate solution over a PBS solution are the reduced neutralization time and the reduced rinsing volume required.

Example 4

After use on patients (repeated loading and regeneration), some adsorbers have shown reduced depletion performance. This is due to the fact that the binding sites are partially masked by precipitated (denatured) proteins, caused by the acidic regeneration (pH 2.8 glycine/HCl) of the matrix. Regeneration with NaOH leads to a reduction of these denatured protein complexes and thus to an improved depletion performance.

The matrix was taken from an adsorber previously used on the patient. A part of the matrix was rinsed with PBS only (control), and other samples were regenerated once with NaOH at different concentrations. The matrix treated in this way was boiled and the supernatant was applied to a gel. FIG. 11 shows the proteins in the gel (Coomassie staining).

FIG. 11 shows that even with a single regeneration with the lowest NaOH concentration, significantly less protein adheres to the matrix. As a result, fewer binding sites are masked and the depletion efficiency increases again. The following table shows the depletion performance. As an additional control, the matrix was regenerated once with the standard glycine/HCl solution. SDS-PAGE analysis of two matrices after regeneration. M=molecular weight marker; K=control (rinsing with PBS); 1.0 to 0.05=concentrations of NaOH with which the agarose was rinsed.

TABLE 1

Depletion performance of three studied matrices after different regenerations. The data include the mean values of the measured depleted total CRP from 3 ELISA measurements.

| Regeneration | Matrix I | Matrix II | Matrix III |
|---|---|---|---|
| Control DF | **1.7 mg** | **0.9 mg** | **1.5 mg** |
| 1.0M NaOH | 2.1 mg | 2.2 mg | 2.1 mg |
| 0.2M NaOH | 2.0 mg | 2.2 mg | 1.8 mg |
| 0.1M NaOH | 1.9 mg | 2.2 mg | 1.8 mg |
| 0.05M NaOH | 1.9 mg | 2.1 mg | 1.8 mg |
| 0.02M NaOH | 1.8 mg | n.t. | n.t |
| Glycine/HCl | **1.6 mg** | n.t. | n.t. |

Bold highlighted entries indicate depletion below the expected value (1.7 mg).
Control was treated with PBS only.
DF = flow through;
n.t. = not treated.

The data presented in Table 1 clearly show that an increase in the depletion efficiency can already be achieved with a low concentration of NaOH. The standard solution glycine/HCl does not achieve any improvement in the depletion performance.

Figure 1:
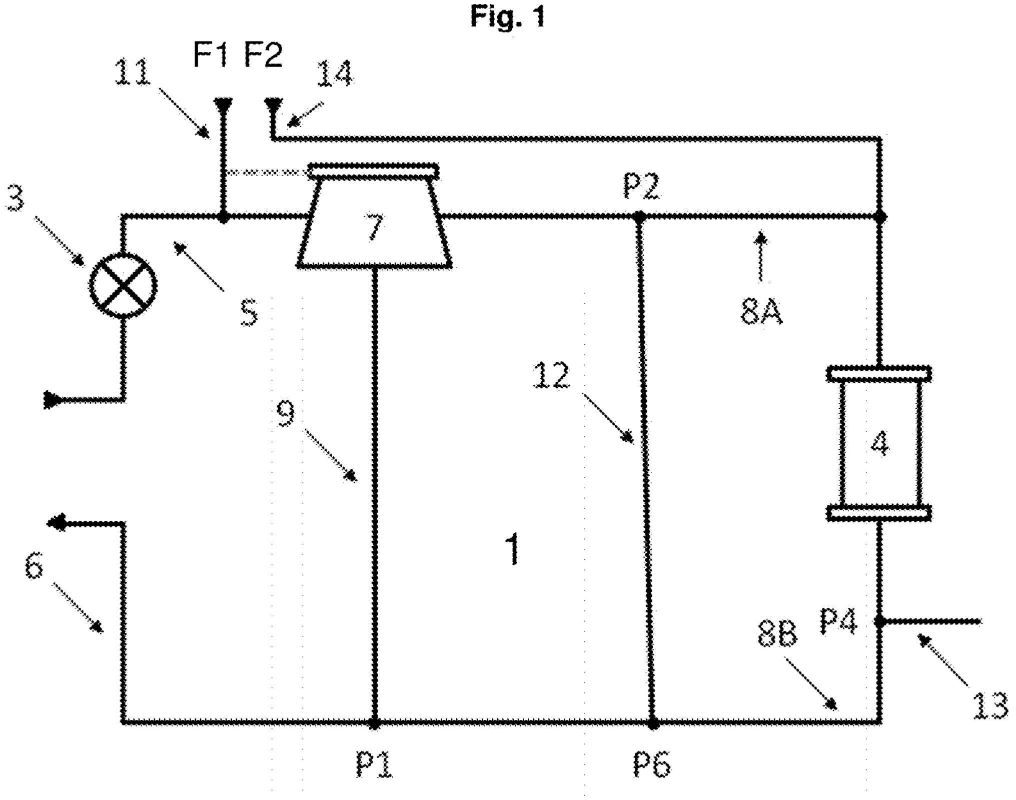
FIG. 1: Schematic drawing of an embodiment of the apheresis device (1) for extracorporeal removal of CRP from blood according to the invention. The arterial line (5), in which there is a means (3) for generation and regulation of a flow of blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) for the connection of a liquid container (F1), which runs into the arterial line (5) or alternatively leads directly into the cell separator (7) (dashed line). The bypass line (12) branches off from the plasma line (8A) at the nodal point (P2) and runs into the plasma line (8B) at the nodal point (P6). The waste line (13) branches off from the plasma line (8B) at the nodal point (P4). In addition, the regeneration line (14) for connection of a liquid container (F2) runs into the plasma line (8A) in a region between the nodal point (P2) and the apheresis column (4). Alternatively, the regeneration line (14) can also lead directly into the apheresis column (4) (not shown).
Figure 2:
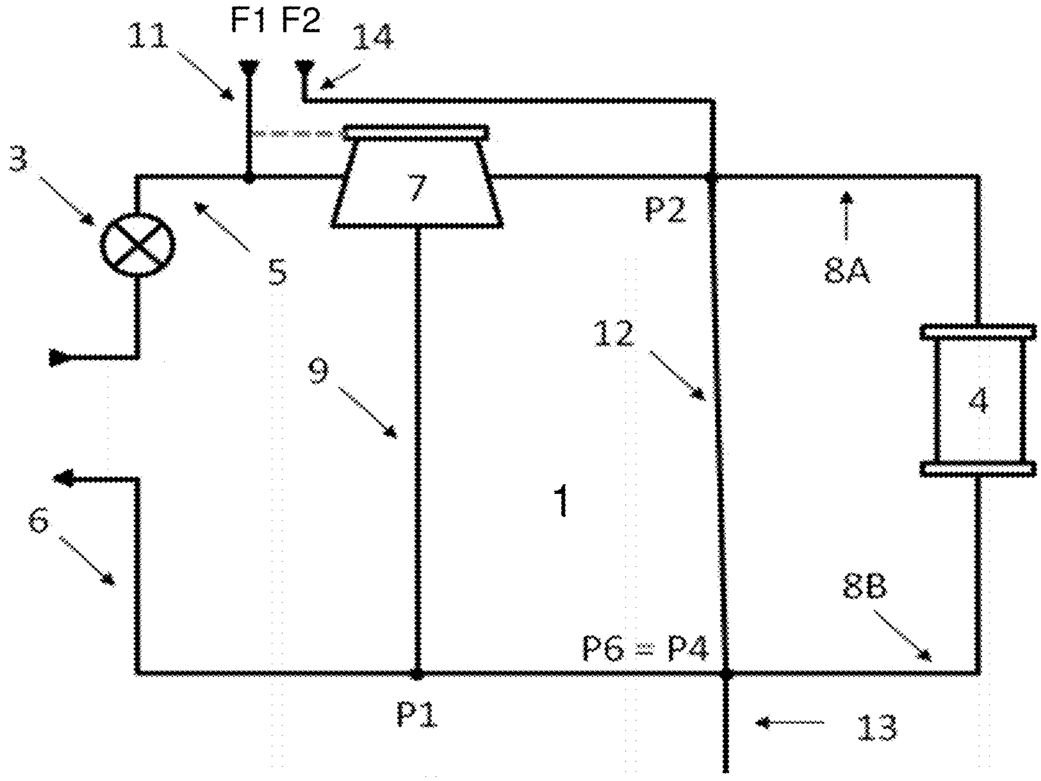
FIG. 2: Schematic drawing of an embodiment of the apheresis device for extracorporeal removal of CRP from blood according to the invention. The arterial line (5), in which there is a means (3) for generation and regulation of a flow of blood (e.g. a peristaltic pump), leads the blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) that runs into the arterial line (5) or alternatively leads directly into the cell separator (7) (dashed line). The bypass line (12) branches off from the plasma line (8A) at the nodal point (P2) and runs into the plasma line (8B) at the nodal point (P6). The waste line (13) branches off from the plasma line (8B) at the nodal point (P6). In addition, the regeneration line (14) runs into the plasma line (8A) at the nodal point (P2).
Figure 3:
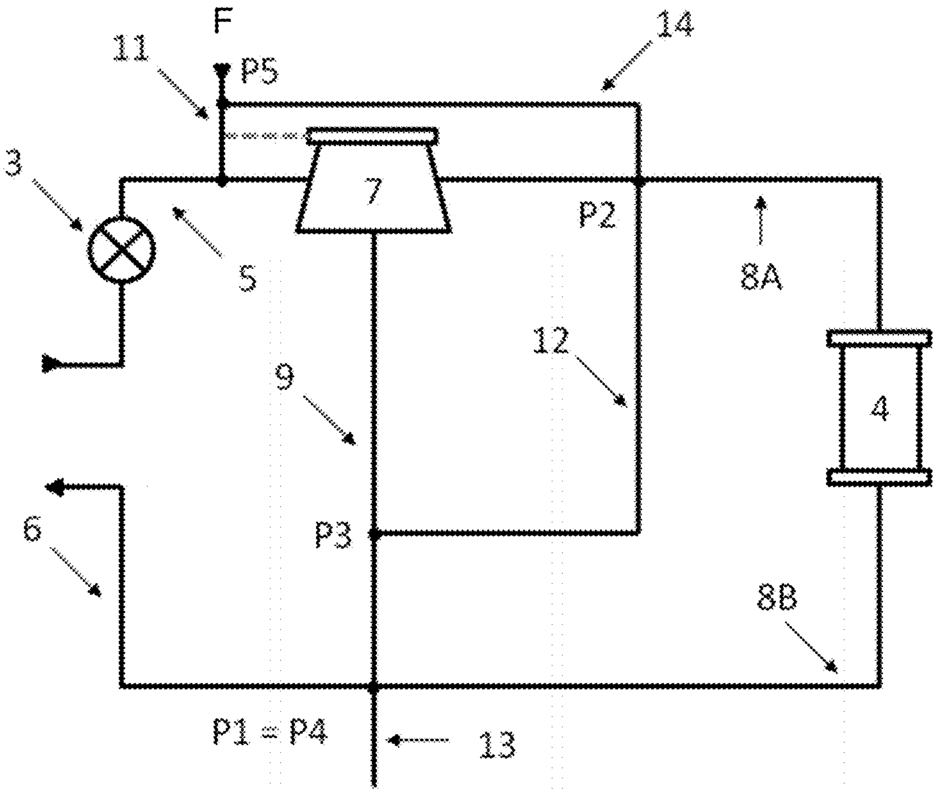
FIG. 3: Schematic drawing of an embodiment of the apheresis device for extracorporeal removal of CRP from blood according to the invention. The arterial line (5), in which there is a means (3) for generation and regulation of a flow of blood (e.g. a peristaltic pump), leads the blood of a patient to the cell separator (7, e.g. a centrifugal cell separator). From this, the plasma line (8A) leads to the apheresis column (4) for affinity chromatographic removal of CRP from blood. From this, the plasma line (8B) leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) that runs into the arterial line (5) or alternatively leads directly into the cell separator (7) (dashed line). The bypass line (12) branches off from the plasma line (8A) at the nodal point (P2) and runs into the cell line (9) at the nodal point (P3). The waste line (13) branches off from the plasma line (8B) at the nodal point (P1). In addition, the regeneration line (14), which branches off from the connection line (11) at the point (P5), runs into the plasma line (8A) at the nodal point (P2).
Figure 4:
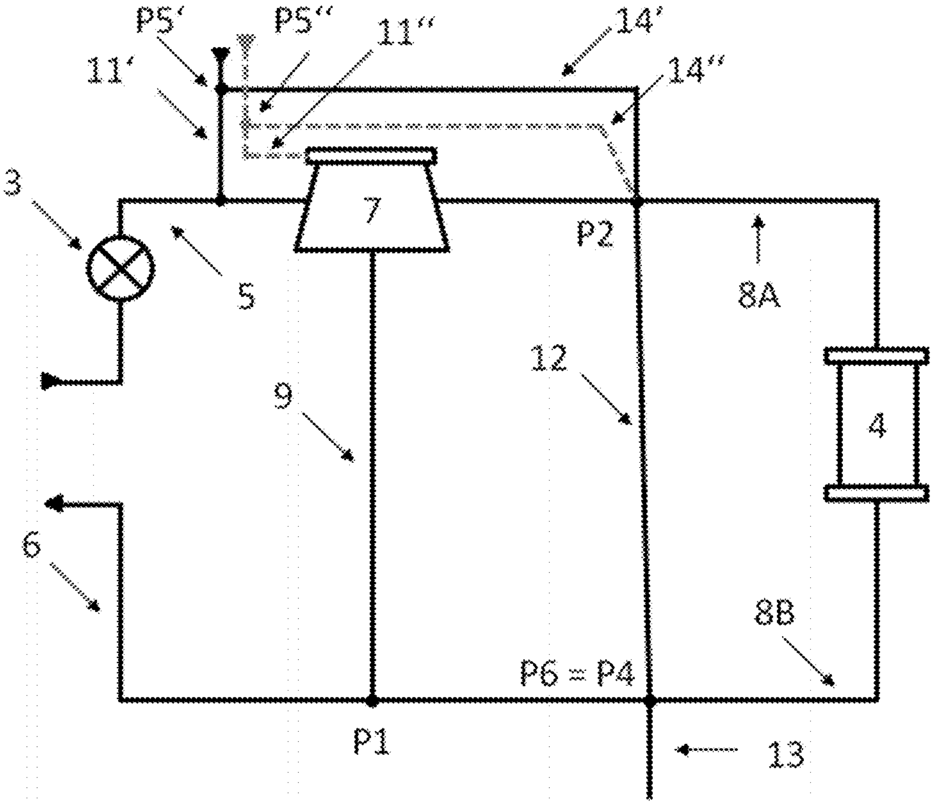
FIG. 4: Schematic drawing of an embodiment of the apheresis device for extracorporeal removal of CRP from blood according to the invention. The arterial line (5), in which there is a means (3) for generation and regulation of a flow of blood (e.g. a peristaltic pump), leads blood of a patient to the cell separator (7, e.g. a centrifugal cell separator). From this, the plasma line (8A) leads to the apheresis column (4) for affinity chromatographic removal of CRP from blood. From this, the plasma line (8B) leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11') that runs into the arterial line (5) but could also run directly into the cell separator (7), as well as a connection line (11") that runs into the cell separator (7) but could also run into the arterial line (5). The bypass line (12) branches off from the plasma line (8A) at the nodal point (P2) and runs into the plasma line (8B) at the nodal point (P6). The waste line (13) branches off from the plasma line (8B) at the nodal point (P6). In addition, both a first regeneration line (14'), which branches off from the connection line (11') at the point (P5'), and a second regeneration line (14"), which branches off from the connection line (11") at the point (P5"), run into the plasma line (8A) at the nodal point (P2).
Figure 5:
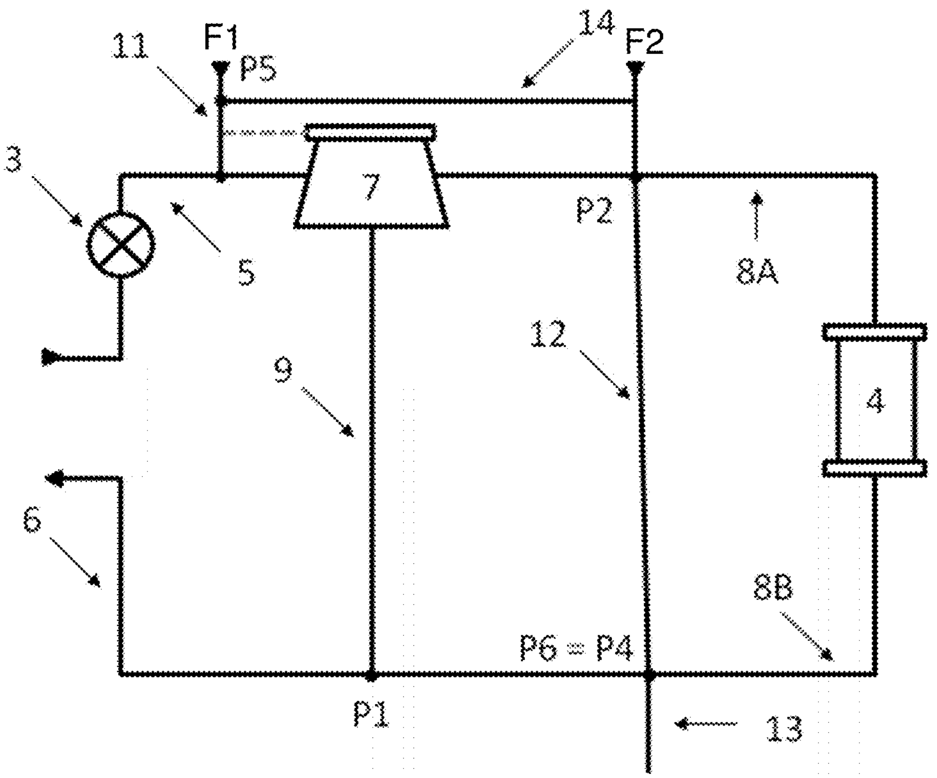
FIG. 5: Schematic drawing of an embodiment of the apheresis device for extracorporeal removal of CRP from blood according to the invention. The arterial line (5), in which there is a means (3) for generation and regulation of a flow of blood (e.g. a peristaltic pump), leads blood of a patient to the cell separator (7, e.g. a centrifugal cell separator). From this, the plasma line (8A) leads to the apheresis column (4) for affinity chromatographic removal of CRP from the blood. From this, the plasma line (8B) leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) for the connection of a liquid container (F1), which runs into the arterial line (5) or alternatively leads directly into the cell separator (7) (dashed line). The bypass line (12) branches off from the plasma line (8A) at the nodal point (P2) and runs into the plasma line (8B) at the nodal point (P6). The waste line (13) branches off from the plasma line (8B) at the nodal point (P6). In addition, the regeneration line (14), which branches off from the connection line (11) at the point (P5), runs into the plasma line (8A) at the nodal point (P2). For better clarity, a central processing unit belonging to the apheresis device according to the invention is not shown. The regeneration line (14) has an additional connection for a liquid container (F2), wherein this connection is located after the cell separator (7) in the direction of flow, so that liquid from this additional liquid container (F2) cannot be fed into the cell separator (7) and cannot be fed into the arterial line (5) before the cell separator (7), but only into the plasma line (8A) in the direction of flow after the cell separator (7) or directly into the apheresis column (4).
Figure 6:
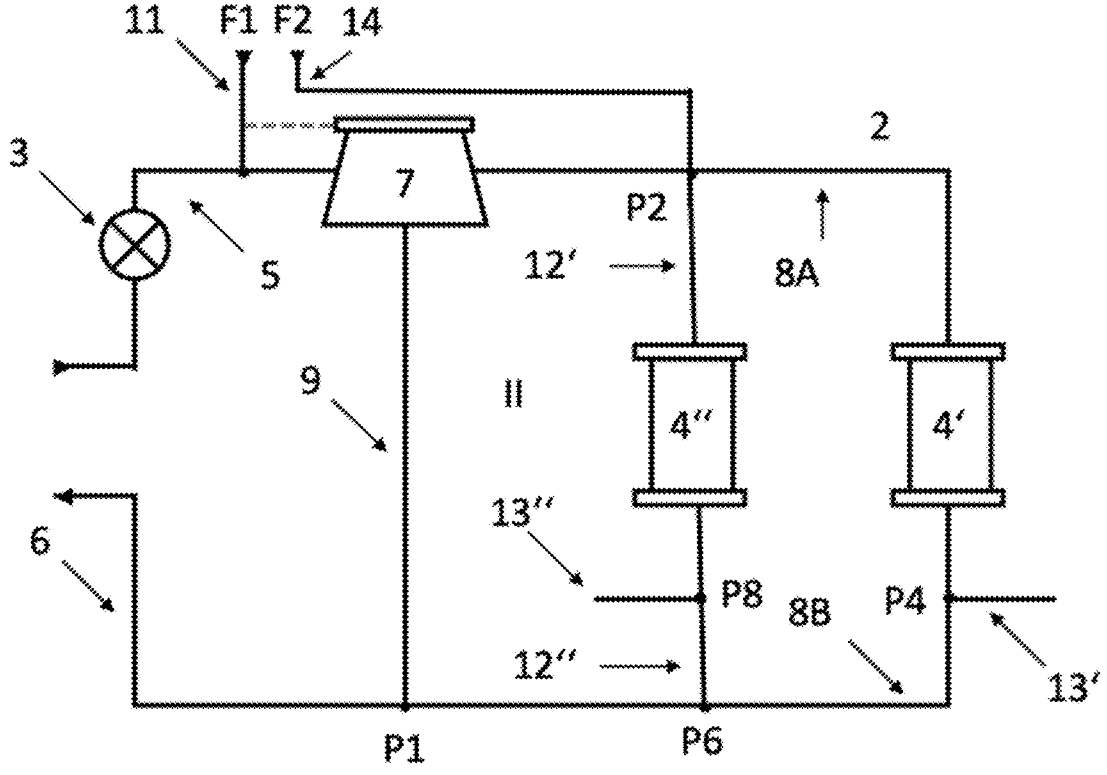
FIG. 6: Schematic drawing of an embodiment of the apheresis device for extracorporeal removal of CRP from blood according to the invention. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branching off from the plasma line (8A) leads to the apheresis column (4") for affinity chromatographic removal of CRP from the blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) for the connection of a liquid container (F1), which runs into the arterial line (5) or alternatively leads directly into the cell separator (7) (dashed line). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13") branches off from the bypass line section (12') of the bypass line (12) at the nodal point (P8), and the waste line (13') branches off from the plasma line (8B) at the nodal point (P4). In addition, the regeneration line (14) for connection of a liquid container (F2) runs into the extracorporeal circulation system (2) at the nodal point (P2).
Figure 7:
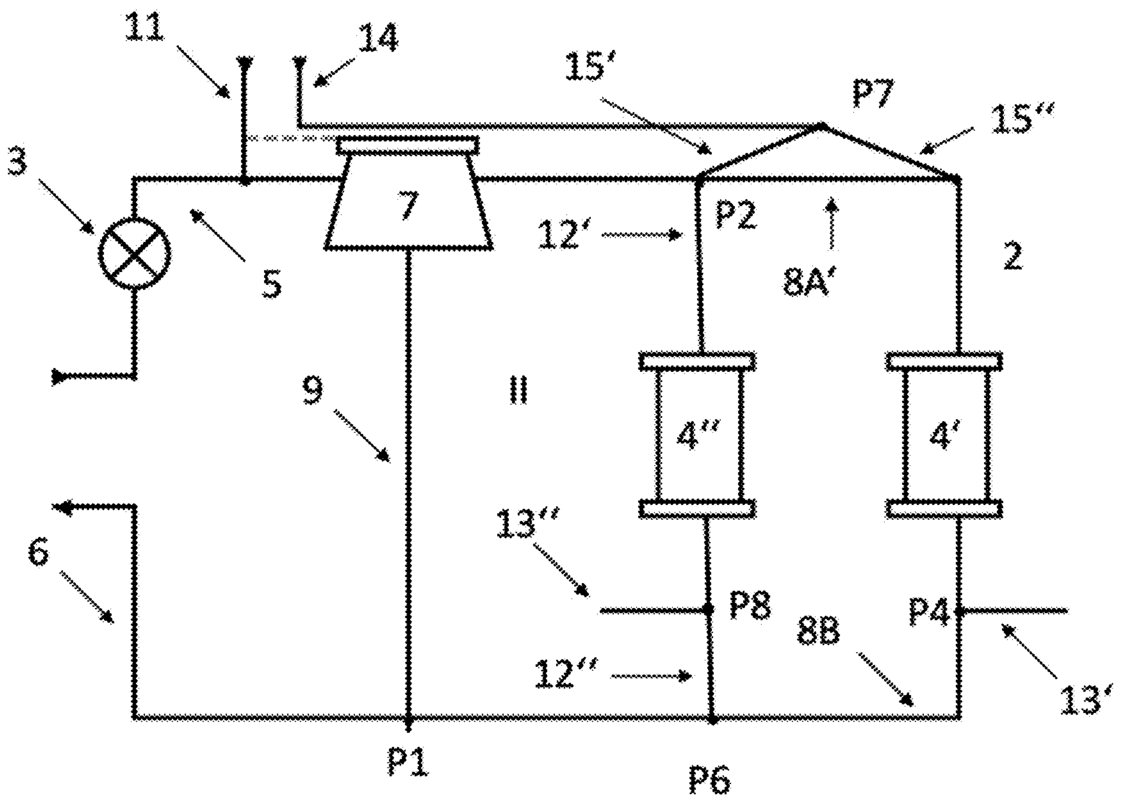
FIG. 7: Schematic drawing of an embodiment of the apheresis for extracorporeal removal of CRP from blood device according to the invention. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branching off from the plasma line (8A) leads to the apheresis column (4") for affinity chromatographic removal of CRP from the blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) for the connection of a liquid container (F1), which runs into the arterial line (5) or alternatively leads directly into the cell separator (7) (dashed line). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13") branches off from the bypass line section (12") of the bypass line (12) at the nodal point (P8), and the waste line (13') branches off from the plasma line (8B) at the nodal point (P4). In addition, the regeneration line (14) leads to the nodal point (P7) for the connection of a liquid container (F2). Two lines (15', 15") branch off at the nodal point (P7). The line (15') runs into the extracorporeal circulation system (2) at the nodal point (P2) and the line (15") runs into the area between the nodal point (P2) and the apheresis column (4").
Figure 8:
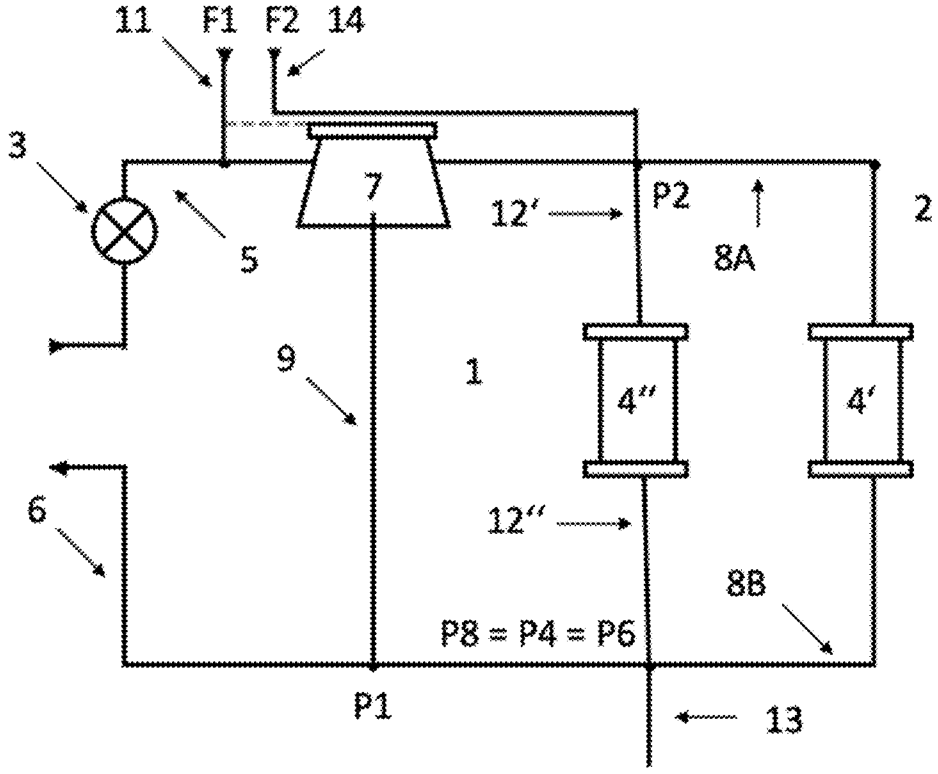
FIG. 8: Schematic drawing of an embodiment of the apheresis device for extracorporeal removal of CRP from blood according to the invention. The arterial line (5), in which there is a means (3) for generating and regulating a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branching off from the plasma line (8A) leads to the apheresis column (4") for affinity chromatographic removal of CRP from blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which returns the treated blood to the patient, also leads from the nodal point (P1). In addition, there is a connection line (11) for the connection of a liquid container (F1), which runs into the arterial line (5) or alternatively leads directly into the cell separator (7) (dashed line). The bypass line section (12') of the bypass line (12) and the plasma line (8A") diverge at the nodal point (P2) and at the nodal point (P6) the bypass line section (12") of the bypass line (12) and the plasma line (8B") converge. The waste line (13) branches off from the extracorporeal circulation system (2) at the nodal point (P6). In addition, the regeneration line (14) for the connection of a liquid container (F2) runs into the extracorporeal circulation system (2) at the nodal point (P2).
Figure 9:
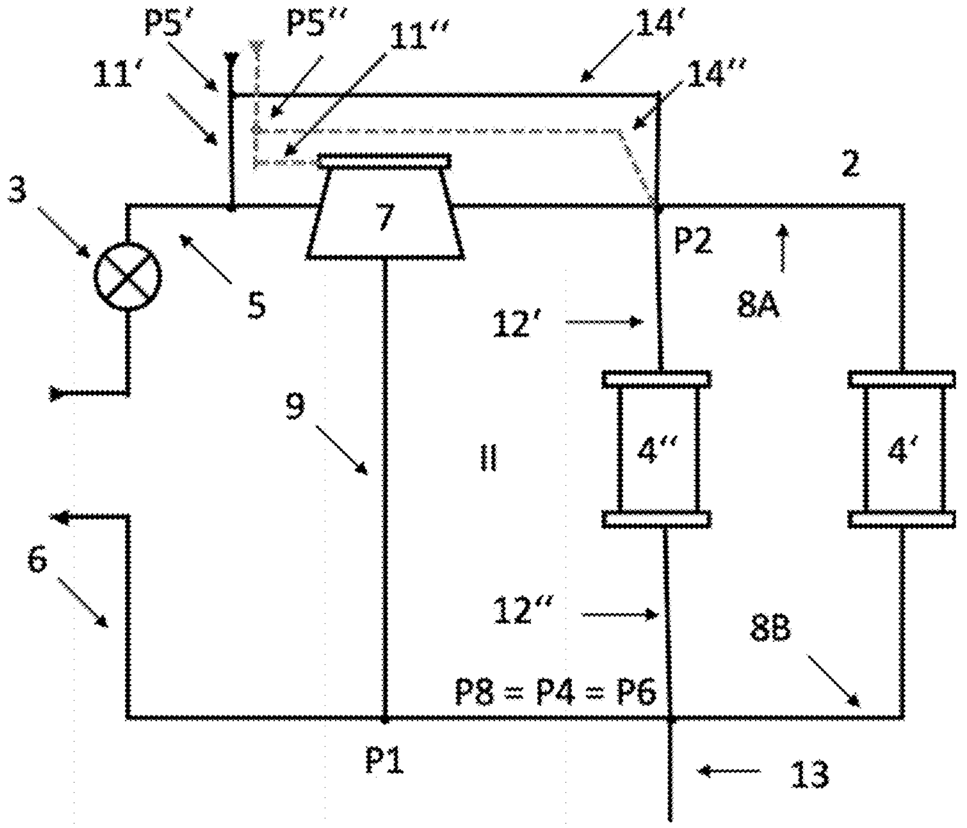
FIG. 9: Schematic drawing of an embodiment of the apheresis device for extracorporeal removal of CRP from blood according to the invention. The arterial line (5), in which there is a means (3) for generation and regulation of a flow of blood (e.g. peristaltic pump), leads the blood of a patient to the cell separator (7, e.g. a centrifugal cell separator). From this, the plasma line (8A) leads to the apheresis column (4') for affinity chromatographic removal of CRP. The bypass line section (12') of the bypass line (12) branching off from the plasma line (8A) leads to the apheresis column (4") for affinity chromatographic removal of CRP from the blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) for the connection of a liquid container (F1), which runs into the arterial line (5) or alternatively leads directly into the cell separator (7) (dashed line). The bypass line section (12') of the bypass line (12) and the plasma line (8A") diverge at the nodal point (P2) and at the nodal point (P6) the bypass line section (12") of the bypass line (12) and the plasma line (8B") converge. The waste line (13) branches off from the extracorporeal circulation system (2) at the nodal point (P6). In addition, the regeneration line (14) for connection of a liquid container (F2) runs into the extracorporeal circulation system (2) at the nodal point (P2).
Figure 10:
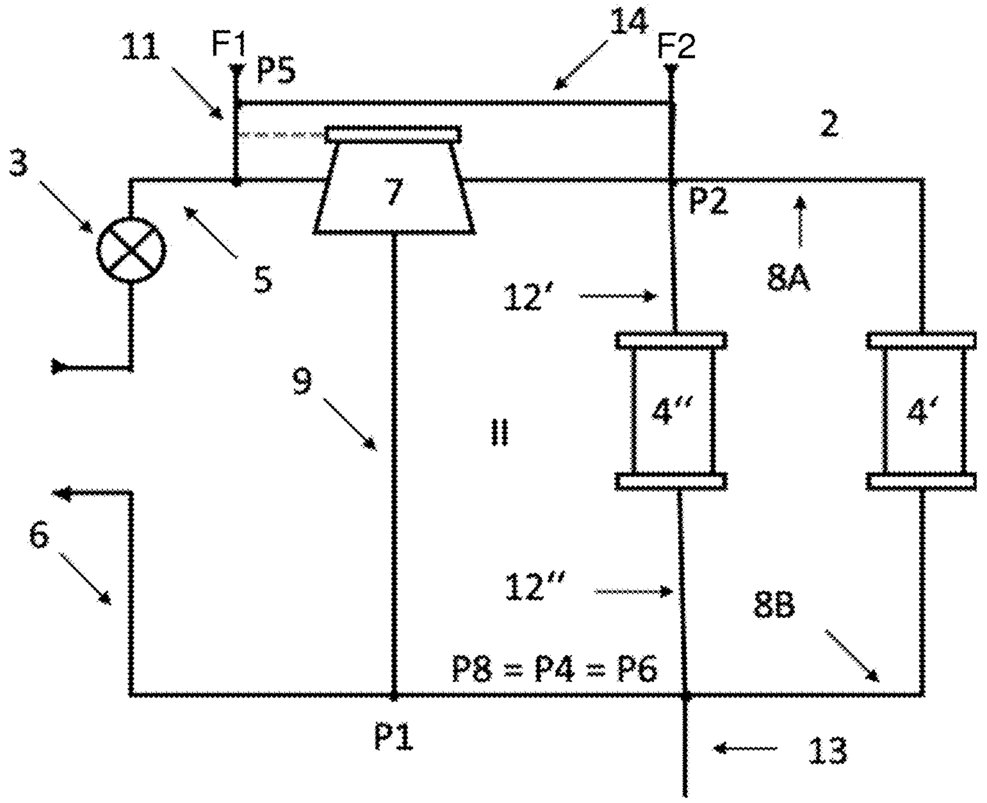
FIG. 10: Schematic drawing of an embodiment of the apheresis device for extracorporeal removal of CRP from blood according to the invention. The arterial line (5), in which there is a means (3) for generation and regulation of a flow of blood (e.g. peristaltic pump), leads the blood of a patient to the cell separator (7, e.g. a centrifugal cell separator. From this the plasma line (8A) leads to the apheresis column (4') for affinity chromatographic removal of CRP. The bypass line section (12') of the bypass line (12) branching off from the plasma line (8A) leads to the apheresis column (4") for affinity chromatographic removal of CRP from the blood. From the apheresis column (4"), the bypass line section (12") of the bypass line (12) for CRP-depleted blood plasma leads to the nodal point (P1), and from the apheresis column (4'), the plasma line (8B) for CRP-depleted blood plasma leads to the nodal point (P1). Another line, the cell line (9), leads from the cell separator (7) to the nodal point (P1). The venous line (6), which returns the treated blood to the patient, also goes off from the nodal point (P1). In addition, there is a connection line (11) for the connection of a liquid container (F1), which runs into the arterial line (5) or alternatively leads directly into the cell separator (7) (dashed line). The bypass line section (12') of the bypass line (12) and the plasma line (8A) diverge at the nodal point (P2) and at the nodal point (P6) the bypass line section (12") of the bypass line (12) and the plasma line (8B) converge. The waste line (13) branches off from the extracorporeal circulation system (2) at the nodal point (P6). In addition, the regeneration line (14), which branches off from the connection line (11) at the point (P5), runs into the extracorporeal circulation system (2) at the nodal point (P2). The feeding line has an additional connection for a liquid container (F2), wherein this connection is located after the cell separator (7) in the direction of flow, so that liquid from this additional liquid container cannot be fed into the cell separator (7) and cannot be fed into the arterial line (5) before the cell separator (7) but only into the bypass line section (12') of the bypass line (12) or into the plasma line (8A) in the direction of flow after the cell separator (7) or directly into the apheresis column (4') or directly into the apheresis column (4").
Figure 11:
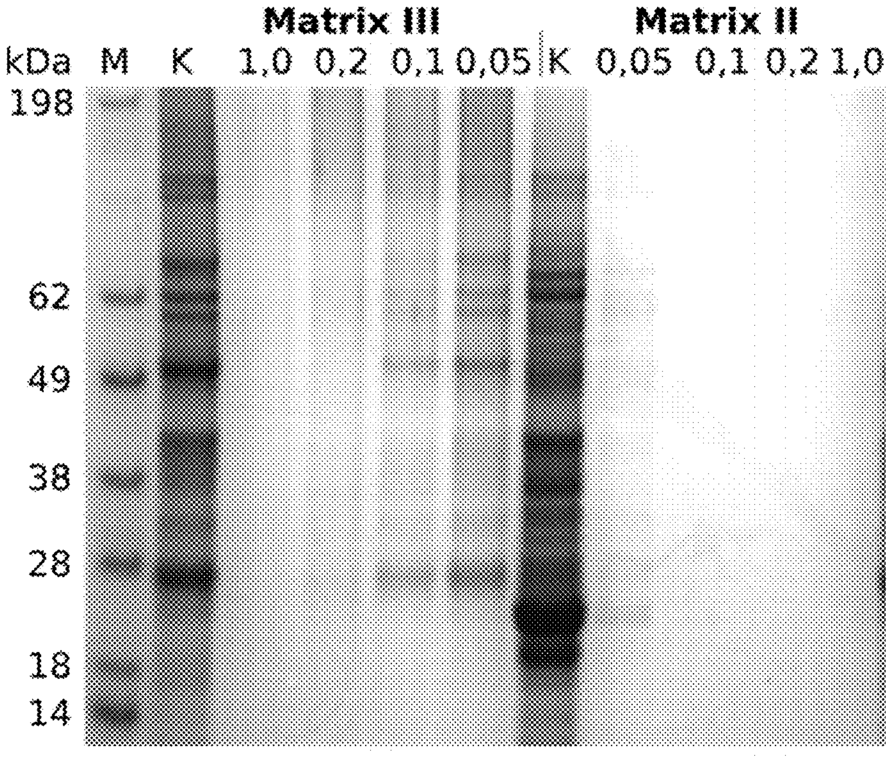
FIG. 11: SDS-PAGE analysis of two matrices after regeneration.

M=molecular weight marker; K=control (rinsing with PBS);

1.0 to 0.05=concentrations of NaOH with which the agarose was rinsed.

LIST OF REFERENCES

1—apheresis device
2—extracorporeal circulation system
3—means for generation and regulation of a flow of blood (or blood plasma) in the extracorporeal circulation system (pump)
4—apheresis column for affinity chromatographic removal of CRP
4'—apheresis column for affinity chromatographic removal of CRP
4"—apheresis column for affinity chromatographic removal of CRP
5 arterial line
6—venous line
7—cell separator
8A—plasma line (before the apheresis column)
8B—plasma line (after the apheresis column)
9—cell line
11—connection line
12—bypass line
12'—bypass line section of the bypass line
12"—bypass line section of the bypass line
13—waste line
13'—waste line
13"—waste line
14—regeneration line
14'—regeneration line
14"—regeneration line
F—liquid container
F1—liquid container 1
F2—liquid container 2
P1—nodal point at which the plasma line (8B) merges into the venous line (6) or nodal point at which the bypass line section (12") of the bypass line (12) or (8B) and the cell line (9) converge and merge into the venous line (6)
P2—nodal point at which the bypass line (12) branches off from the plasma line (8A) or nodal point at which the bypass line section (12') of the bypass line and the plasma line (8B) diverge
P3—nodal point at which the bypass line (12) runs into the cell line (9)
P4—nodal point at which the waste line (13) branches off from the plasma line (8B) or nodal point at which the waste line (13') branches off from the plasma line (8B)
P5—nodal point at which the regeneration line (14) branches off from the connection line (11)
P5, P5'—nodal point at which the regeneration line (14) branches off from the connection line (11) or (11'), respectively.
P6—nodal point at which the bypass line (12) runs into the plasma line (8B) or nodal point at which the bypass line section (12") of the bypass line (12) and the plasma line (8B) converge and together as the bypass line section (12") of the bypass line (12) or (8B) run to the point P1.
P7—nodal point in the regeneration line (14) from which the regeneration line (14) divides the lines (15') and (15").
P8—nodal point at which the waste line (13") branches off from the bypass line section (12") of the bypass line.

What is claimed is:

1. A method of using an alkali hydroxide solution for regeneration of an apheresis column, wherein the apheresis column is an apheresis column for the affinity chromatographic selective removal of human C-reactive protein (CRP) from blood or blood plasma, wherein the apheresis column contains a matrix for affinity chromatographic removal of human CRP, the matrix comprising a matrix substrate material to which ligands are bound which have the property of specifically binding CRP, the ligands bound to the matrix substrate material being selected from phosphocholine or phosphoethanolamine, or wherein the matrix comprises a matrix substrate material functionalized with at least one ω-phosphonooxyalkylammonium group and/or at least one ω-ammoniumalkoxy-hydroxyphosphoryloxy group; and wherein CRP binds to the matrix in the apheresis column with higher affinity than other substances present in the blood, the method being performed after blood or blood plasma of a patient has been passed through the apheresis column to remove CRP during a therapeutic apheresis treatment of the patient, wherein the apheresis column contains bound CRP, the method comprising:

(a) introducing a rinsing solution into the apheresis column to remove blood or blood plasma from the column, wherein the rinsing solution is a sodium chloride solution or a phosphate-buffered saline solution; and (b) introducing the alkali hydroxide solution into the apheresis column for regeneration of the apheresis column, wherein bound CRP is eluted and the apheresis column is simultaneously restored to a therapeutically usable state, and wherein the concentration of the alkali hydroxide in the alkali hydroxide solution is in a range of 0.04 mol/l to 0.4 mol/l.

2. The method of using an alkali hydroxide solution according to claim 1, wherein the alkali hydroxide solution is a lithium hydroxide solution, a sodium hydroxide solution, a potassium hydroxide solution, or a mixture of the aforementioned solutions.

3. The method of using an alkali hydroxide solution according to claim 1, wherein the concentration of the alkali hydroxide in the alkali hydroxide solution is in a range of 0.08 mol/l to 0.1 mol/l.

4. The method of using an alkali hydroxide solution according to claim 1, wherein the concentration of the alkali hydroxide in the alkali hydroxide solution is 0.084 mol/l.

5. The method of using an alkali hydroxide solution according to claim 1, wherein the alkali hydroxide solution has a pH in a range of 12 to 14.

6. The method of using an alkali hydroxide solution according to claim 1, wherein the alkali hydroxide solution has a pH in a range of 12-13.7.

7. The method of using an alkali hydroxide solution according to claim 1, wherein the regeneration occurs during an apheresis treatment for extracorporeal removal of CRP from blood or blood plasma, wherein the apheresis column is not connected to the extracorporeal circulation system during the regeneration.

8. The method of using an alkali hydroxide solution according to claim 1, wherein the apheresis column is saturated with CRP.

9. The method of using an alkali hydroxide solution according to claim 1, wherein the apheresis column comprises a matrix substrate material functionalized with at least one ω-phosphonooxyalkylammonium group and/or at least one ω-ammoniumalkoxy-hydroxyphosphoryloxy group.

10. The method of using an alkali hydroxide solution according to claim 9, wherein the at least one ω-phosphonooxyalkylammonium group corresponds to a group represented by the following general formula (I)

(I)

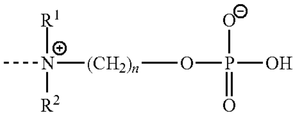

wherein n is selected from 2 and 3;

$R^1$ and $R^2$ are independently of each other selected from: —H, —$CH_3$, —$C_2H_5$, —$C_3H_7$, —$C_4H_9$, —$C_5H_{11}$, —$C_6H_{13}$, or $R^1$ and $R^2$ together with the nitrogen atom to which they are bound can form a heterocycle selected from:

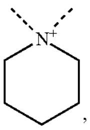, 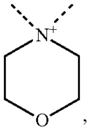, and 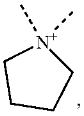, wherein one or more hydrogen atom(s) may be replaced by (a) fluorine atom(s).

11. The method of using an alkali hydroxide solution according to claim 9, wherein the at least one ω-ammoniumalkoxy-hydroxyphosphoryloxy group corresponds to a group of the following general formula (II)

(II)

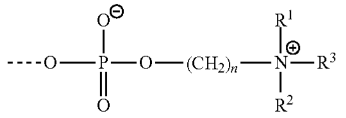

wherein n is selected from 2 and 3;

$R^1$, $R^2$ and $R^3$ are independently of each other selected from: —H, —$CH_3$, —$C_2H_5$, —$C_3H_7$, —$C_4H_9$, —$C_5H_{11}$, —$C_6H_{13}$, or $R^1$ and $R^2$ together with the nitrogen atom to which they are bound can form a heterocycle selected from:

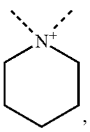, 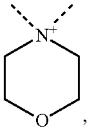, and 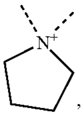, and $R^3$ is selected from: —H, —$CH_3$, —$C_2H_5$, —$C_3H_7$, —$C_4H_9$, —$C_5H_{11}$, —$C_6H_{13}$, and preferably-H;

wherein one or more hydrogen atom(s) may be replaced by (a) fluorine atom(s).

12. The method of using an alkali hydroxide solution according to claim 1, wherein the apheresis column contains agarose.

13. The method of using an alkali hydroxide solution according to claim 1, wherein the apheresis column contains DNA and/or RNA.

14. A method for regeneration of an apheresis column for affinity chromatographic selective removal of C-reactive protein (CRP) from blood or blood plasma, the method being performed after blood or blood plasma of a patient has been passed through the apheresis column to remove CRP during a therapeutic apheresis treatment of the patient, wherein the apheresis column contains bound CRP, the method comprising the steps:

(I') introducing a rinsing solution into an apheresis column preferably containing blood plasma; wherein the rinsing solution is a sodium chloride solution or a phosphate buffered saline solution;

(I) introducing an alkali hydroxide solution, preferably a sodium hydroxide solution, into an apheresis column for regeneration of the apheresis column, wherein the apheresis column contains a matrix for affinity chromatographic removal of CRP, the matrix comprising a matrix substrate material to which ligands are bound which have the property of specifically binding CRP, the ligands bound to the matrix substrate material being selected from phosphocholine or phosphoethanolamine, or wherein the matrix comprises a matrix substrate material functionalized with at least one ω-phosphonooxyalkylammonium group and/or at least one ω-ammoniumalkoxy-hydroxyphosphoryloxy group; and wherein CRP binds to the matrix in the apheresis column with higher affinity than other substances present in the blood, wherein the concentration of the alkali hydroxide in the alkali hydroxide solution is in a range of 0.04 mol/l to 0.4 mol/l.

15. The method for regeneration of an apheresis column for affinity chromatographic selective removal of CRP from blood or blood plasma according to claim 14 comprising the steps:

(I') introducing a rinsing solution into an apheresis column preferably containing blood plasma; wherein the rinsing solution is a sodium chloride solution or a phosphate buffered saline solution;

(I) introducing an alkali hydroxide solution, preferably a sodium hydroxide solution, into an apheresis column for regeneration of the apheresis column; and (II) introducing a neutralization solution.

16. The method for regeneration of an apheresis column for affinity chromatographic selective removal of CRP from blood or blood plasma according to claim 14 comprising the steps:

(I') introducing a rinsing solution into an apheresis column preferably containing blood plasma;

(I) introducing an alkali hydroxide solution, preferably a sodium hydroxide solution, into the apheresis column for regeneration of the apheresis column;

(II") stopping the introduction of the alkali hydroxide solution, preferably the sodium hydroxide solution, after step (I); and (II) introducing a neutralization solution.

17. A method for regeneration of an apheresis column for affinity chromatographic selective removal of C-reactive protein (CRP) from blood or blood plasma in an apheresis device comprising:

an extracorporeal circulation system for blood, means for generation and regulation of a flow of the blood in the extracorporeal circulation system, a cell separator for separation of the blood into blood plasma and cellular components, at least one apheresis column for affinity chromatographic removal of CRP from the blood, wherein the extracorporeal circulation system comprises an arterial line to the cell separator, a plasma line from the cell separator to the apheresis column, a plasma line for CRP-depleted blood plasma from the apheresis column to a point, a cell line for separated cellular components from the cell separator to the point, and a venous line starting from the point, at least one connection line for connection of at least one liquid container to the arterial line or the cell separator, a bypass line branching off from the plasma line and running into the plasma line, a waste line branching off directly from the apheresis column or from the plasma line in the direction of flow before the junction of the bypass line, and at least one regeneration line leading in the direction of flow at or after the branch of the bypass line to the plasma line or running directly into the apheresis column, the apheresis device being configured to be resistant to an alkali hydroxide solution, the method enabling regeneration during operation and being performed after blood or blood plasma of a patient has been passed through the apheresis column to remove CRP during a therapeutic apheresis treatment of the patient, wherein the apheresis column contains bound CRP, the method being characterized by the following steps:

(A) starting the redirection of the separated plasma from the plasma line into the bypass line, thereby stopping the introduction of the separated plasma from the plasma line into the apheresis column, (B) starting the introduction of a rinsing solution via the at least one regeneration line into the plasma line or directly into the apheresis column, wherein the rinsing solution is a sodium chloride solution or a phosphate buffered saline solution;

(C) starting the redirection of the liquid flow exiting the apheresis column from the plasma line into the waste line, (D) stopping the introduction of the rinsing solution and transition to the introduction of a regeneration solution via the at least one regeneration line into the plasma line or directly into the apheresis column, wherein the regeneration solution is an alkali hydroxide solution, (E) starting the redirection of the liquid flow exiting the apheresis column from the plasma line to the waste line, (F) stopping the introduction of regeneration solution, (G) starting the introduction of neutralization solution, (H) stopping the introduction of neutralization solution and stopping the redirection of the separated plasma from the plasma line into the bypass line, thereby introduction of the separated plasma from the plasma line into the apheresis column, (I) closing the waste line, wherein the apheresis column contains a matrix for affinity chromatographic removal of CRP, the matrix comprising a matrix substrate material to which ligands are bound which have the property of specifically binding CRP, the ligands bound to the matrix substrate material being selected from phosphocholine or phosphoethanolamine, or wherein the matrix comprises a matrix substrate material functionalized with at least one ω-phosphonooxyalkylammonium group and/or at least one ω-ammoniumalkoxy-hydroxyphosphoryloxy group; and wherein CRP binds to the matrix in the apheresis column with higher affinity than other substances present in the blood, wherein the concentration of the alkali hydroxide in the alkali hydroxide solution is in a range of 0.04 mol/l to 0.4 mol/l.

18. The method according to claim 17 for regeneration of an apheresis column for affinity chromatographic removal, the method characterized by the following steps:

(A) starting the redirection of the separated plasma from the plasma line into the bypass line, thereby stopping the introduction of the separated plasma from the plasma line into the apheresis column, (B) starting the introduction of a rinsing solution via the at least one regeneration line into the plasma line or directly into the apheresis column, (C) starting the redirection of the liquid flow exiting the apheresis column from the plasma line into the waste line, (D) stopping the introduction of the rinsing solution and transition to the introduction of a regeneration solution via the at least one regeneration line into the plasma line or directly into the apheresis column, wherein the regeneration solution is an alkali hydroxide solution, (E) stopping the introduction of the regeneration solution and transition to the introduction of the neutralization solution via the at least one regeneration line into the plasma line or directly into the apheresis column, (F) stopping the introduction of the neutralization solution and transition to the introduction of the rinsing solution via the at least one regeneration line into the plasma line or directly into the apheresis column, (G) stopping the introduction of the rinsing solution and stopping the redirection of the separated plasma from the plasma line into the bypass line, thereby direction of the separated plasma from the plasma line into the apheresis column;

(H) closing the waste line.

* * * * *